US008211907B2

(12) United States Patent
Hayashibe et al.

(10) Patent No.: US 8,211,907 B2
(45) Date of Patent: Jul. 3, 2012

(54) FUSED INDANE COMPOUND

(75) Inventors: Satoshi Hayashibe, Tokyo (JP); Shingo Yamasaki, Tokyo (JP); Nobuyuki Shiraishi, Tokyo (JP); Hiroaki Hoshii, Tokyo (JP); Takahiko Tobe, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 116 days.

(21) Appl. No.: 12/741,307

(22) PCT Filed: Nov. 26, 2008

(86) PCT No.: PCT/JP2008/071370
§ 371 (c)(1),
(2), (4) Date: May 4, 2010

(87) PCT Pub. No.: WO2009/069610
PCT Pub. Date: Jun. 4, 2009

(65) Prior Publication Data
US 2010/0267695 A1    Oct. 21, 2010

(30) Foreign Application Priority Data
Nov. 28, 2007  (JP) ................................ 2007-307753

(51) Int. Cl.
*A61K 31/44* (2006.01)
*C07D 221/06* (2006.01)
(52) U.S. Cl. ........................................ 514/290; 546/79
(58) Field of Classification Search .................. 514/290; 546/79
See application file for complete search history.

(56) References Cited

U.S. PATENT DOCUMENTS

| 5,574,060 A * | 11/1996 | Rothman et al. ............. 514/411 |
| 2007/0197594 A1 | 8/2007 | Hayashibe et al. |
| 2009/0118267 A1 | 5/2009 | Finsinger et al. |

FOREIGN PATENT DOCUMENTS

| JP | 9-504514 | 5/1997 |
| RU | 2 279 880 | 7/2006 |
| WO | 00/11952 | 3/2000 |
| WO | 2006/033318 | 3/2006 |
| WO | 2006/094602 | 9/2006 |

OTHER PUBLICATIONS

Finsinger et al. CAS: 145:292878, 2006.*
Bhattacharya, et al., "Synthesis and Stereochemical Studies on the Reduction of Some Pyrrole Derivatives", J. Chem. Soc., Perkin Trans. 1 (1984) 5-13.
DeWit, et al., "cis-Fused hexahydro-4aH-indenol[1,2-b]pyridines: transformation of bridgehead ester group and conversion to tricyclic analogues or NK-1 and dopamine receptor ligands", Tetrahedron Letters, vol. 42, No. 29 (2001) 4919-22.
Froimowitz, "Conformational Analysis of Cocaine, the Potent Analog 2β-Carbomethoxy-3β-(4-Fluorophenyl) Tropane (CFT), and Other Dopamine Reuptake Blockers", Journal of Computational Chemistry, vol. 14, No. 8 (1993) 934-43.
Mach, et al., "Development of Novel 1,2,3,4-Tetrahydroisoquinoline Derivatives and Closely Related Compounds as Potent and Selective Dopamine D3 Receptor Ligands", ChemBioChem, vol. 5, No. 4 (2004) 508-18.
Maiti, et al., "Role of Remote Heteroatoms and Nature of the Reducing Agents on the Stereochemical Course of Reductions of the Carbon-Nitrogen π-Bond of a New Class of Tetrohydropyridines", J. Chem. Soc., Perkin Trans. 1 (1988) 611-21.
Parcell, et al., "The Preparation of Tetrahydropyridines from Enamines and Imines", J. Org. Chem., vol. 28, No. 12 (1963) 3468-73.
Terada, et al., "Comprehensive Analysis of Quantitative Structure-Activity Relationships of Catecholamine-Uptake Inhibitors", Quant. Struc. Act. Relat., vol. 10, No. 2 (1991) 118-25.
Van Emelen, et al., "Synthesis of cis-fused hexahydro-4aH-indeno[1,2-b]pyridines via intramolecular Ritter reaction and their conversion into tricyclic analogues of NK-1 and dopamine receptor ligands", Tetrahedron, vol. 58, No. 21 (2002) 4225-36.

* cited by examiner

*Primary Examiner* — Rei-tsang Shiao
(74) *Attorney, Agent, or Firm* — Fitzpatrick, Cella, Harper & Scinto

(57) ABSTRACT

To provide a compound which is useful as an NMDA receptor antagonist. The present inventors have studied a compound having an NMDA receptor antagonistic action, and confirmed that the fused indane compound of the present invention has an excellent NMDA receptor antagonistic action, thereby completed the present invention. The fused indane compound of the present invention has an excellent NMDA receptor antagonistic action and can be used as a prophylactic and/or therapeutic agent for Alzheimer's disease, cerebrovascular dementia, Parkinson's disease, intractable depression, attention deficit hyperactivity disorder, migraines, or the like.

17 Claims, No Drawings

FUSED INDANE COMPOUND

This application is a 371 of PCT Application No. PCT/JH2008/071370 filed Nov. 26, 2008.

TECHNICAL FIELD

The present invention relates to a pharmaceutical, particularly a fused indane compound which is useful as an NMDA receptor antagonist.

BACKGROUND ART

Glutamic acid acts as a neurotransmitter in the central nervous system of mammals, and controls the activity of neurocytes or the release of neurotransmitters via a glutamate receptor existing in synapses. At present, a glutamate receptor is classified into an ionotropic receptor and a metabotropic receptor from many pharmacological and physiological studies (Hollmann M. and Heinemann S., Annu. Rev. Neurosci., 17 (1994) 31-108). An NMDA (N-methyl-D-aspartic acid) receptor is an ionotropic glutamate receptor specifically sensitive to the NMDA as an agonist (Moriyoshi K., Nature, 354 (1991) 31-37; Meguro H., Nature, 357 (1992) 70-74); and has high $Ca^{2+}$ ion permeability (Iino M., J. Physiol., 424 (1990) 151-165). The NMDA receptor is expressed with a specific pattern in the central nervous system (Ozawa S., Prog. Neurobiol., 54 (1998) 581-618).

From many pharmacological and biological studies, it is believed that an NMDA receptor is involved in higher nerve activities such as memory, learning, and the like (Morris R. G., Nature, 319 (1986) 774-776; Tsien J. Z., Cell, 87 (1996) 1327-1338). On the other hand, it is suggested that the acute or chronic enhancement or inhibition of the NMDA receptor activity relates to various nervous system diseases, for example, ischemic apoplexy, hemorrhagic brain disorder, traumatic brain disorder, neurodegenerative disorders (Alzheimer's disease, cerebrovascular dementia, Parkinson's disease, Huntington's disease, amyotrophic lateral sclerosis, and the like), glaucoma, AIDS encephalopathy, dependence, schizophrenia, depression, mania, stress-related diseases, epilepsy, pain, and the like (Beal M. F., FASEB J., 6 (1992) 3338-3344; Heresco-Levy U. and Javitt D. C., Euro. Neuropsychopharmacol., 8 (1998) 141-152; Hewitt D. J., Clin. J. Pain, 16 (2000) S73-79). Accordingly, it is thought that drugs capable of controlling the activity of an NMDA receptor would be extremely useful in clinical application.

As drugs capable of controlling the activity of an NMDA receptor, a large number of non-competitive NMDA receptor antagonists are reported, but many of them have not been used in clinical application because of their side effects based on the NMDA receptor-antagonizing effect thereof, for example, mental aberrations such as hallucinations and confusion, giddiness and the like. It has been tried to apply some of the conventional NMDA receptor antagonists, for example, ketamine and dextromethorphan, against pain or the like in clinical application (Fisher K., J. Pain Symptom Manage., 20 (2000) 358-373). However, their safety margin in treatments is narrow, and their clinical use is limited (Fide P. K., Pain, 58 (1994) 347-354). Also, memantine is known as a non-competitive NMDA receptor antagonist that has comparatively few side effects (Parsons C. G., Neuropharmacol., 38 (1999) 735-767); and recently, it has been reported that it is effective for Alzheimer's disease (Reisberg B., N. Engl. J. Med., 348 (2003) 1333-1341). However, the safety margin of memantine as a medicine is still not satisfactory, and development of an NMDA receptor antagonist having a broader safety margin is desired (Ditzler K., Arzneimittelforschung, 41 (1991) 773-780; Maier C., Pain, 103 (2003) 277-283; Riederer P., Lancet, 338 (1991) 1022-1023). It is expected that creation of such an NMDA receptor antagonist superior in terms of a broader safety margin may bring about new clinical usefulness of the NMDA receptor antagonist.

It is known that a cyclic amine derivative represented by the following formula has an NMDA receptor antagonistic action and is useful for treating and preventing Alzheimer's disease, cerebrovascular dementia, Parkinson's disease, ischemic apoplexy, or pain (Patent Document 1). However, this document neither discloses nor suggests the fused indane compound according to the present invention.

[Chem. 1]

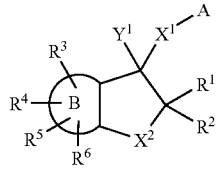

(For the symbols in the formula, refer to this document).

Further, it is known that a compound represented by the following formula has anticancer activities (Patent Document 2). However, there is neither disclosure nor suggestion on its NMDA receptor antagonistic action, nor its usefulness for treating Alzheimer's disease, cerebrovascular dementia, Parkinson's disease, ischemic apoplexy, pain, or the like according to the present invention.

[Chem. 2]

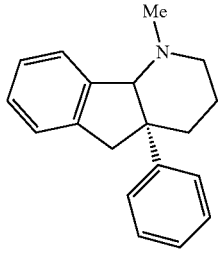

Furthermore, it is suggested that a compound represented by the following formula is a ligand for a dopamine D3 receptor and relates to the diseases regarding central nerves (Non-Patent Document 1). However, this document neither discloses nor suggests the fused indane compound according to the present invention.

[Chem. 3]

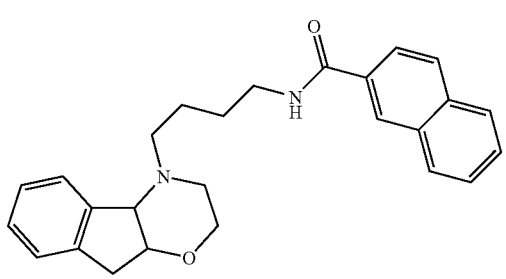

Further, an indeno[1,2-b]pyridine compound in which a phenyl group is substituted at the 9b-position is known as a ligand for NK-1 and dopamine receptors (Non-Patent Document 2 and Non-Patent Document 3). However, this document neither discloses nor suggests the fused indane compound according to the present invention.

In addition, an indeno[1,2-b]pyridine compound in which a phenyl group is substituted at the 5-position is known (Non-Patent Document 4). However, this document neither discloses nor suggests the fused indane compound according to the present invention.

Also, it is suggested that a compound represented by the following formula has a catecholamine uptake inhibitory action and can be used as an anti-depressant or an anti-Parkinson's disease drug (Non-Patent Document 5). However, this document neither discloses nor suggests the fused indane compound according to the present invention.

[Chem. 4]

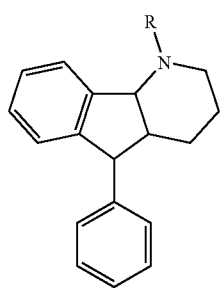

(In the formula, R represents —H or methyl).

Furthermore, two compounds below are known on the database as CAS registry numbers 1220-39-9 and 97555-62-9.

[Chem. 5]

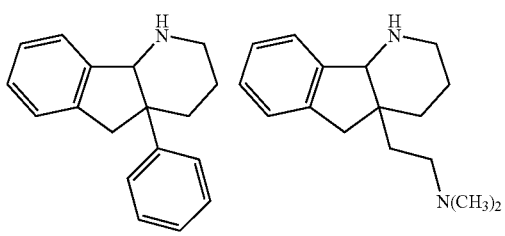

[Patent Document 1] Pamphlet of International Patent Publication WO 2006/033318
[Patent Document 2] Pamphlet of International Patent Publication WO 2006/094602
[Non-Patent Document 1] ChemBioChem, 2004, Vol. 5, No. 4, pp. 508-518
[Non-Patent Document 2] Tetrahedron, 2002, Vol. 58, No. 21, pp. 4225-4236
[Non-Patent Document 3] Tetrahedron Letters, 2001, Vol. 42, No. 29, pp. 4919-4922
[Non-Patent Document 4] Journal of Computational Chemistry, 1993, Vol. 14, No. 8, pp. 934-943
[Non-Patent Document 5] Quantitative Structure-Activity Relationships, 1991, Vol. 10, No. 2, pp. 118-125

DISCLOSURE OF INVENTION

Problem that the Invention is to Solve

A pharmaceutical having an NMDA receptor antagonistic action, in particular, a compound which is useful as a prophylactic and/or therapeutic agent for Alzheimer's disease, cerebrovascular dementia, Parkinson's disease, ischemic apoplexy, pain, intractable depression, attention deficit hyperactivity disorder, migraines, schizophrenia, generalized anxiety disorder, obsessive-compulsive disorder, autism, bulimia, drug addiction, or the like, is provided.

Means for Solving the Problem

The present inventors have studied a compound having an NMDA receptor antagonistic action, and found that the fused indane compound of the present invention has an NMDA receptor antagonistic action, thereby completed the present invention.

That is, the following is provided by the present invention.
(1) A compound of the formula (I) or a pharmaceutically acceptable salt thereof:

[Chem. 6]

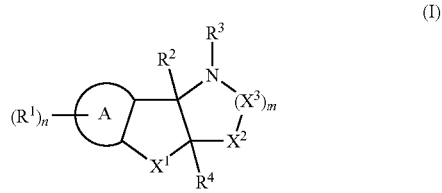

(wherein,
Ring A represents a benzene ring or a thiophene ring,
$R^1$ represents $C_{1-6}$ alkyl which may be substituted with one or more groups selected from the group consisting of —OH, —O—$C_{1-6}$ alkyl, amino which may be substituted with one or two $C_{1-6}$ alkyl, and oxo; —O—$C_{1-6}$ alkyl; halogen; cyano; or cyclic amino,
n represents an integer of 0 to 4 in the case where Ring A represents a benzene ring, and represents an integer of 0 to 2 in the case where Ring A represents a thiophene ring,
$R^2$ represents —H or $C_{1-6}$ alkyl,
$R^3$ represents $C_{1-6}$ alkyl which may be substituted with phenyl, cycloalkyl, or —H,
$R^4$ represents $C_{1-6}$ alkyl which may be substituted with one or more groups selected from the group consisting of —OH, —O—$C_{1-6}$ alkyl, amino which may be substituted with one or two $C_{1-6}$ alkyl, oxo, and cyclic amino; cycloalkyl; aryl; or —OH,
$X^1$ represents —$CH_2$—, —$(CH_2)_2$—, —O—, —S—, or —CH($R^0$)—,
$X^2$ represents —C($R^A$)($R^B$)— or —O—,
$X^3$ represents —C($R^C$)($R^D$)—,
m represents an integer of 1 to 3,
$R^0$ represents —H, or $R^0$ is combined with $R^4$ to represent $C_{3-5}$ alkylene, and,
$R^A$, $R^B$, $R^C$, and $R^D$ are the same as or different from each other, and represent —H or $C_{1-6}$ alkyl,
wherein, in the case where m represents 2 or 3, each of $R^C$ and $R^D$ may be the same as or different from each other,
provided that 1-methyl-4a-phenyl-2,3,4,4a,5,9b-hexahydro-1H-indeno[1,2-b]pyridine, 4a-phenyl-2,3,4,4a,5,9b- hexahydro-1H-indeno[1,2-b]pyridine, and 2-(1,2,3,4,5,9b-hexahydro-4aH-indeno[1,2-b]pyridin-4a-yl)-N,N-dimethylethaneamine are excluded.

The same shall apply hereinafter.)

(2) The compound or a pharmaceutically acceptable salt thereof of (1), wherein Ring A is a benzene ring.

(3) The compound or a pharmaceutically acceptable salt thereof of (1), wherein Ring A is a thiophene ring.

(4) The compound or a pharmaceutically acceptable salt thereof described in either of (2) or (3), wherein $X^1$ is —CH$_2$—, $X^2$ is —CH$_2$—, $X^3$ is —CH$_2$—, and m is 2.

(5) The compound or a pharmaceutically acceptable salt thereof of (4), wherein $R^4$ is $C_{1-6}$ alkyl which may be substituted with one or more groups selected from the group consisting of —OH, —O—$C_{1-6}$ alkyl, amino which may be substituted with one or two $C_{1-6}$ alkyl, oxo, and cyclic amino.

(6) The compound or a pharmaceutically acceptable salt thereof of (5), wherein $R^4$ is methyl, ethyl, isopropyl, methoxymethyl, or ethoxymethyl.

(7) The compound or a pharmaceutically acceptable salt thereof of (6), wherein $R^3$ is —H, methyl, or ethyl.

(8) The compound or a pharmaceutically acceptable salt thereof of (7), wherein $R^2$ is —H or methyl.

(9) The compound or a pharmaceutically acceptable salt thereof of (8), wherein n is 0.

(10) The compound or a pharmaceutically acceptable salt thereof of (1), which is (4aRS,9bRS)-4a-methyl-2,3,4,4a,5,9b-hexahydro-1H-indeno[1,2-b]pyridine, (4aRS,9bRS)-1,4a-dimethyl-2,3,4,4a,5,9b-hexahydro-1H-indeno[1,2-b]pyridine, (4aRS,9bRS)-4a-ethyl-2,3,4,4a,5,9b-hexahydro-1H-indeno[1,2-b]pyridine, (4aR,9bR)-4a-methyl-2,3,4,4a,5,9b-hexahydro-1H-indeno[1,2-b]pyridine, (4aS,9bS)-4a-methyl-2,3,4,4a,5,9b-hexahydro-1H-indeno[1,2-b]pyridine, (4aRS,9bSR)-4a-isopropyl-2,3,4,4a,5,9b-hexahydro-1H-indeno[1,2-b]pyridine, (4aR,9bR)-4a-ethyl-2,3,4,4a,5,9b-hexahydro-1H-indeno[1,2-b]pyridine, (4aS,9bS)-4a-ethyl-2,3,4,4a,5,9b-hexahydro-1H-indeno[1,2-b]pyridine, (4aRS,9bRS)-8-methoxy-1,4a-dimethyl-2,3,4,4a,5,9b-hexahydro-1H-indeno[1,2-b]pyridine, (4aRS,9bRS)-4a,9b-dimethyl-2,3,4,4a,5,9b-hexahydro-1H-indeno[1,2-b]pyridine, (4aRS,9bRS)-4a-(ethoxymethyl)-2,3,4,4a,5,9b-hexahydro-1H-indeno[1,2-b]pyridine, (3bRS,7aRS)-2,7a-dimethyl-4,5,6,7,7a,8-hexahydro-3bH-thieno[2',3':4,5]cyclopenta[1,2-b]pyridine, (4aRS,9bRS)-4a-(methoxymethyl)-9b-methyl-2,3,4,4a,5,9b-hexahydro-1H-indeno[1,2-b]pyridine, (4aRS,10bSR)-4a-methyl-1,2,3,4,4a,5,6,10b-octahydrobenzo[h]quinoline, (5aRS,10bSR)-5a-methyl-1,2,3,4,5,5a,6,10b-octahydroindeno[1,2-b]azepine, [(4aRS,9bRS)-4a-ethyl-2,3,4,4a,5,9b-hexahydro-1H-indeno[1,2-b]pyridin-8-yl]methanol, (4aRS,9bRS)-4a-methyl-1,2,3,4,4a,9b-hexahydro[1]benzothieno[3,2-b]pyridine, (4aR,9bR)-4a,9b-dimethyl-2,3,4,4a,5,9b-hexahydro-1H-indeno[1,2-b]pyridine, or (4aS,9bS)-4a,9b-dimethyl-2,3,4,4a,5,9b-hexahydro-1H-indeno[1,2-b]pyridine, or a pharmaceutically acceptable salt thereof.

(11) The compound or a pharmaceutically acceptable salt thereof of (1), which is (4aRS,9bRS)-4a-methyl-2,3,4,4a,5,9b-hexahydro-1H-indeno[1,2-b]pyridine, (4aR,9bR)-4a-methyl-2,3,4,4a,5,9b-hexahydro-1H-indeno[1,2-b]pyridine, (4aS,9bS)-4a-methyl-2,3,4,4a,5,9b-hexahydro-1H-indeno[1,2-b]pyridine, (4aRS,9bRS)-4a-ethyl-2,3,4,4a,5,9b-hexahydro-1H-indeno[1,2-b]pyridine, (4aR,9bR)-4a-ethyl-2,3,4,4a,5,9b-hexahydro-1H-indeno[1,2-b]pyridine, (4aS,9bS)-4a-ethyl-2,3,4,4a,5,9b-hexahydro-1H-indeno[1,2-b]pyridine, (4aRS,9bRS)-4a,9b-dimethyl-2,3,4,4a,5,9b-hexahydro-1H-indeno[1,2-b]pyridine, (4aR,9bR)-4a,9b-dimethyl-2,3,4,4a,5,9b-hexahydro-1H-indeno[1,2-b] pyridine, or (4aS,9bS)-4a,9b-dimethyl-2,3,4,4a,5,9b-hexahydro-1H-indeno[1,2-b]pyridine, or a pharmaceutically acceptable salt thereof.

(12) A pharmaceutical composition comprising the compound or a pharmaceutically acceptable salt thereof of (1), and a pharmaceutically acceptable excipient.

(13) A pharmaceutical composition for treating Alzheimer's disease, cerebrovascular dementia, Parkinson's disease, ischemic apoplexy, pain, intractable depression, attention deficit hyperactivity disorder, migraines, schizophrenia, generalized anxiety disorder, obsessive-compulsive disorder, autism, bulimia, or drug addiction, which comprises the compound or a pharmaceutically acceptable salt thereof of (1), or 4a-phenyl-2,3,4,4a,5,9b-hexahydro-1H-indeno[1,2-b]pyridine or a pharmaceutically acceptable salt thereof, and a pharmaceutically acceptable excipient.

(14) The pharmaceutical composition of (13), which is a pharmaceutical composition for treating Alzheimer's disease, cerebrovascular dementia, Parkinson's disease, intractable depression, attention deficit hyperactivity disorder, or migraines.

(15) Use of the compound or a pharmaceutically acceptable salt thereof of (1), or 4a-phenyl-2,3,4,4a,5,9b-hexahydro-1H-indeno[1,2-b]pyridine or a pharmaceutically acceptable salt thereof, for the manufacture of a pharmaceutical composition for treating Alzheimer's disease, cerebrovascular dementia, Parkinson's disease, ischemic apoplexy, pain, intractable depression, attention deficit hyperactivity disorder, migraines, schizophrenia, generalized anxiety disorder, obsessive-compulsive disorder, autism, bulimia, or drug addiction.

(16) The use of (15), wherein the pharmaceutical composition for treating Alzheimer's disease, cerebrovascular dementia, Parkinson's disease, ischemic apoplexy, pain, intractable depression, attention deficit hyperactivity disorder, migraines, schizophrenia, generalized anxiety disorder, obsessive-compulsive disorder, autism, bulimia, or drug addiction is a pharmaceutical composition for treating Alzheimer's disease, cerebrovascular dementia, Parkinson's disease, intractable depression, attention deficit hyperactivity disorder, or migraines.

(17) A method for treating Alzheimer's disease, cerebrovascular dementia, Parkinson's disease, ischemic apoplexy, pain, intractable depression, attention deficit hyperactivity disorder, migraines, schizophrenia, generalized anxiety disorder, obsessive-compulsive disorder, autism, bulimia, or drug addiction, comprising administering to a patient an effective amount of the compound or a pharmaceutically acceptable salt thereof of (1), or 4a-phenyl-2,3,4,4a,5,9b-hexahydro-1H-indeno[1,2-b]pyridine or a pharmaceutically acceptable salt thereof.

(18) The method for treating of (17), which is a method for treating Alzheimer's disease, cerebrovascular dementia, Parkinson's disease, intractable depression, attention deficit hyperactivity disorder, or migraines.

Further, the present invention relates to a pharmaceutical composition for treating Alzheimer's disease, cerebrovascular dementia, Parkinson's disease, ischemic apoplexy, pain, intractable depression, attention deficit hyperactivity disorder, migraines, schizophrenia, generalized anxiety disorder, obsessive-compulsive disorder, autism, bulimia, drug addiction, or the like, which contains the compound of the formula (I) or a pharmaceutically acceptable salt thereof, 1-methyl-4a-phenyl-2,3,4,4a,5,9b-hexahydro-1H-indeno[1,2-b]pyridine or a pharmaceutically acceptable salt thereof, 4a-phenyl-2,3,4,4a,5,9b-hexahydro-1H-indeno[1,2-b]pyridine or a pharmaceutically acceptable salt thereof, or 2-(1,2,3,4,5,9b- hexahydro-4aH-indeno[1,2-b]pyridin-4a-yl)-N,N-dimethyl ethane amine or a pharmaceutically acceptable salt thereof. Further, this pharmaceutical composition includes a therapeutic agent for Alzheimer's disease, cerebrovascular dementia, Parkinson's disease, ischemic apoplexy, pain, intractable depression, attention deficit hyperactivity disorder, migraines, schizophrenia, generalized anxiety disorder, obsessive-compulsive disorder, autism, bulimia, drug addiction, or the like, which contains the compound of the formula (I) or a pharmaceutically acceptable salt thereof, 1-methyl-4a-phenyl-2,3,4,4a,5,9b-hexahydro-1H-indeno[1,2-b]pyridine or a pharmaceutically acceptable salt thereof, 4a-phenyl-2,3,4,4a,5,9b-hexahydro-1H-indeno[1,2-b]pyridine or a pharmaceutically acceptable salt thereof, or 2-(1,2,3,4,5,9b-hexahydro-4aH-indeno[1,2-b]pyridin-4a-yl)-N,N-dimethyl ethane amine or a pharmaceutically acceptable salt thereof.

Further, the present invention relates to use of the compound of the formula (I) or a pharmaceutically acceptable salt thereof, 1-methyl-4a-phenyl-2,3,4,4a,5,9b-hexahydro-1H-indeno[1,2-b]pyridine or a pharmaceutically acceptable salt thereof, 4a-phenyl-2,3,4,4a,5,9b-hexahydro-1H-indeno[1,2-b]pyridine or a pharmaceutically acceptable salt thereof, or 2-(1,2,3,4,5,9b-hexahydro-4aH-indeno[1,2-b]pyridin-4a-yl)-N,N-dimethyl ethane amine or a pharmaceutically acceptable salt thereof for the manufacture of a therapeutic agent for Alzheimer's disease, cerebrovascular dementia, Parkinson's disease, ischemic apoplexy, pain, intractable depression, attention deficit hyperactivity disorder, migraines, schizophrenia, generalized anxiety disorder, obsessive-compulsive disorder, autism, bulimia, drug addiction, or the like, and a method for treating Alzheimer's disease, cerebrovascular dementia, Parkinson's disease, ischemic apoplexy, pain, intractable depression, attention deficit hyperactivity disorder, migraines, schizophrenia, generalized anxiety disorder, obsessive-compulsive disorder, autism, bulimia, drug addiction, or the like, comprising administering to a patient an effective amount of the compound of the formula (I) or a pharmaceutically acceptable salt thereof, 1-methyl-4a-phenyl-2,3,4,4a,5,9b-hexahydro-1H-indeno[1,2-b]pyridine or a pharmaceutically acceptable salt thereof, 4a-phenyl-2,3,4,4a,5,9b-hexahydro-1H-indeno[1,2-b]pyridine or a pharmaceutically acceptable salt thereof, or 2-(1,2,3,4,5,9b-hexahydro-4aH-indeno[1,2-b]pyridin-4a-yl)-N,N-dimethyl ethane amine or a pharmaceutically acceptable salt thereof.

Effects of the Invention

The compound of the formula (I) or a pharmaceutically acceptable salt thereof, or 4a-phenyl-2,3,4,4a,5,9b-hexahydro-1H-indeno[1,2-b]pyridine or a pharmaceutically acceptable salt thereof (which may be hereinafter referred to as "the compound according to the present invention" in some cases) has an NMDA receptor antagonistic action and thus can be used as a prophylactic and/or therapeutic agent for Alzheimer's disease, cerebrovascular dementia, Parkinson's disease, ischemic apoplexy, pain, intractable depression, attention deficit hyperactivity disorder, migraines, schizophrenia, generalized anxiety disorder, obsessive-compulsive disorder, autism, bulimia, drug addiction, or the like.

BEST MODE FOR CARRYING OUT THE INVENTION

Hereinafter, the present invention will be described in more detail.

In the present specification, the "$C_{1-6}$ alkyl" refers to a linear or branched alkyl having 1 to 6 carbon atoms, for example, methyl, ethyl, n-propyl, isopropyl, n-butyl, isobutyl, sec-butyl, tert-butyl, n-pentyl, n-hexyl, and the like. In another embodiment, it is $C_{1-3}$ alkyl, in a further embodiment, methyl or ethyl, and in an even further embodiment, methyl.

The "$C_{3-5}$ alkylene" refers to a linear or branched alkylene having 3 to 5 carbon atoms, for example, trimethylene, tetramethylene, pentamethylene, 1-methylpropylene, 2-methylpropylene, 1-methylbutylene, 2-methylbutylene, 1,1-dimethylpropylene, 1,2-dimethylpropylene, 1,3-dimethylpropylene, 1-ethylpropylene, and the like. In another embodiment, it is trimethylene, tetramethylene or pentamethylene, and in a further embodiment, tetramethylene.

The "cycloalkyl" refers to a $C_{3-8}$ saturated hydrocarbon ring group, for example, cyclopropyl, cyclobutyl, cyclopentyl, cyclohexyl, cycloheptyl, cyclooctyl, and the like. In another embodiment, it is $C_{5-7}$ cycloalkyl, in a further embodiment, cyclohexyl.

The "aryl" is a $C_{6-14}$ mono- to tricyclic aromatic hydrocarbon ring group, for example, phenyl, naphthyl, and the like. In another embodiment, it is phenyl.

The "halogen" means —F, —Cl, —Br, or —I.

The "cyclic amino" is a monovalent group having at least one nitrogen as a ring-constituting atom, wherein the nitrogen has a binding arm, or a monovalent group of 3- to 10-membered cyclic amine, which may further have at least one ring-constituting atom selected from nitrogen, oxygen, and sulfur, for example, 1-azetidinyl, 1-pyrrolidinyl, 1-piperidinyl, 1-azepanyl, morpholino, thiomorpholino, 1-piperazinyl, or the like. In another embodiment, it is 1-pyrrolidinyl or 1-piperidinyl.

In the present specification, the "which may be substituted" represents unsubstituted or having 1 to 5 substituents. Further, if it has a plurality of substituents, the substituents may be the same as or different from each other.

Certain embodiments regarding the compound according to the present invention will be described below.

(1) The compound in which Ring A is a benzene ring. Or in another embodiment, the compound in which Ring A is a thiophene ring.

(2) The compound in which n is 0. Or in another embodiment, the compound in which n is 1, and $R^1$ is $C_{1-6}$ alkyl or —O—$C_{1-6}$ alkyl.

(3) The compound in which $R^2$ is —H or methyl. Or in another embodiment, the compound in which $R^2$ is —H. Or in a further embodiment, the compound in which $R^2$ is methyl.

(4) The compound in which $R^3$ is —H, methyl, or ethyl. Or in another embodiment, the compound in which $R^3$ is —H or methyl. Or in a further embodiment, the compound in which $R^3$ is —H. Or in an even further embodiment, the compound in which $R^3$ is methyl.

(5) The compound in which $R^4$ is $C_{1-6}$ alkyl which may be substituted with —O—$C_{1-6}$ alkyl. Or in another embodiment, the compound in which $R^4$ is $C_{1-3}$ alkyl which may be substituted with —O—$C_{1-2}$ alkyl. Or in a further embodiment, the compound in which $R^4$ is methyl. Or in an even further embodiment, the compound in which $R^4$ is ethyl. Or in a still further embodiment, the compound in which $R^4$ is isopropyl. Or in an still even further embodiment, the compound in which $R^4$ is methoxymethyl or ethoxymethyl.

(6) The compound in which $X^1$ is —$CH_2$—.

(7) The compound in which $X^2$ is —$C(R^A)(R^B)$—, and $R^A$ and $R^B$ are both —H.

(8) The compound in which $X^3$ is —$C(R^C)(R^D)$—, and $R^C$ and $R^D$ are both —H, and m is 2.

(9) The compound which is a combination of at least two groups as described in (1) to (8) above.

Specific examples of the compound included in the present invention include the following compounds:

(4aRS,9bRS)-4a-methyl-2,3,4,4a,5,9b-hexahydro-1H-indeno[1,2-b]pyridine, (4aRS,9bRS)-1,4a-dimethyl-2,3,4,4a,5,9b-hexahydro-1H-indeno[1,2-b]pyridine, (4aRS,9bRS)-4a-ethyl-2,3,4,4a,5,9b-hexahydro-1H-indeno[1,2-b]pyridine, (4aR,9bR)-4a-methyl-2,3,4,4a,5,9b-hexahydro-1H-indeno[1,2-b]pyridine, (4aS,9bS)-4a-methyl-2,3,4,4a,5,9b-hexahydro-1H-indeno[1,2-b]pyridine, (4aRS,9bSR)-4a-isopropyl-2,3,4,4a,5,9b-hexahydro-1H-indeno[1,2-b]pyridine, (4aR,9bR)-4a-ethyl-2,3,4,4a,5,9b-hexahydro-1H-indeno[1,2-b]pyridine, (4aS,9bS)-4a-ethyl-2,3,4,4a,5,9b-hexahydro-1H-indeno[1,2-b]pyridine, (4aRS,9bRS)-8-methoxy-1,4a-dimethyl-2,3,4,4a,5,9b-hexahydro-1H-indeno[1,2-b]pyridine, (4aRS,9bRS)-4a,9b-dimethyl-2,3,4,4a,5,9b-hexahydro-1H-indeno[1,2-b]pyridine, (4aRS,9bRS)-4a-(ethoxymethyl)-2,3,4,4a,5,9b-hexahydro-1H-indeno[1,2-b]pyridine, (3bRS,7aRS)-2,7a-dimethyl-4,5,6,7,7a,8-hexahydro-3bH-thieno[2',3':4,5]cyclopenta[1,2-b]pyridine, (4aRS,9bRS)-4a-(methoxymethyl)-9b-methyl-2,3,4,4a,5,9b-hexahydro-1H-indeno[1,2-b]pyridine, (4aRS,10bSR)-4a-methyl-1,2,3,4,4a,5,6,10b-octahydrobenzo[h]quinoline, (5aRS,10bSR)-5a-methyl-1,2,3,4,5,5a,6,10b-octahydroindeno[1,2-b]azepine,[(4aRS,9bRS)-4a-ethyl-2,3,4,4a,5,9b-hexahydro-1H-indeno[1,2-b]pyridin-8-yl]methanol, (4aRS,9bRS)-4a-methyl-1,2,3,4,4a,9b-hexahydro[1]benzothieno[3,2-b]pyridine, (4aR,9bR)-4a,9b-dimethyl-2,3,4,4a,5,9b-hexahydro-1H-indeno[1,2-b]pyridine, and (4aS,9bS)-4a,9b-dimethyl-2,3,4,4a,5,9b-hexahydro-1H-indeno[1,2-b]pyridine, and pharmaceutically acceptable salts of these compounds.

The compound according to the present invention may in some cases exist in tautomers or geometrical isomers, depending on the kinds of the substituents. In the present specification, the compound according to the present invention may be described in only one form of isomers, but the present invention includes other isomers, isolated forms of the isomers, or a mixture thereof.

Furthermore, the compound according to the present invention may have asymmetric carbon atoms or asymmetries in some cases, and correspondingly, it may exist in the isolated forms of optical isomers. The present invention includes the isolated form of the optical isomer of the compound according to the present invention or a mixture thereof.

In addition, in the stereochemical expressions of a chemical structure, the compound denoted as a racemic compound includes, in addition to the racemic compound itself, isolated forms of each optical isomer. For example, if it is denoted as (4aRS,9bRS), in addition to the racemic having a relative configuration of (4aRS,9bRS), each of the optical active products, a (4aR,9bR)-form and a (4aS,9bS)-form, and a mixture thereof are included.

Additionally, the pharmaceutically acceptable prodrugs of the compound according to the present invention are also included in the present invention. The pharmaceutically acceptable prodrug refers to a compound having a group which can be converted into an amino group, a hydroxyl group, a carboxyl group, or the like, by solvolysis or under a physiological condition. Examples of the groups for forming a prodrug include those as described in Prog. Med., 5, 2157-2161 (1985) or "Pharmaceutical Research and Development" (Hirokawa Publishing Company, 1990), vol. 7, Drug Design, 163-198.

Furthermore, the compound according to the present invention may form an acid addition salt or a salt with a base, depending on the kind of the substituents, and these salts are included in the present invention, as long as they are pharmaceutically acceptable salts. Specifically, examples thereof include acid addition salts with inorganic acids such as hydrochloric acid, hydrobromic acid, hydroiodic acid, sulfuric acid, nitric acid, phosphoric acid, and the like, and with organic acids such as formic acid, acetic acid, propionic acid, oxalic acid, malonic acid, succinic acid, fumaric acid, maleic acid, lactic acid, malic acid, mandelic acid, tartaric acid, dibenzoyl tartaric acid, ditolyl tartaric acid, citric acid, methanesulfonic acid, ethanesulfonic acid, benzenesulfonic acid, p-toluenesulfonic acid, aspartic acid, glutamic acid, and the like, and salts with inorganic bases such as sodium, potassium, magnesium, calcium, aluminum, and the like, and organic bases such as methylamine, ethylamine, ethanolamine, lysine, ornithine, and the like, salts with various amino acids, ammonium salts, and others.

Additionally, the present invention also includes various hydrates or solvates, and polymorphism of the compound according to the present invention and a pharmaceutically acceptable salt thereof. Furthermore, the present invention also includes the compounds labeled with various radioactive isotopes or non-radioactive isotopes.

(Production Processes)

The compound according to the present invention and a pharmaceutically acceptable salt thereof can be prepared by applying various known synthetic methods, using the characteristics based on their basic skeletons or the kinds of the substituents. At this time, depending on the types of the functional groups, it is in some cases effective from the viewpoint of the preparation techniques to substitute the functional group with an appropriate protecting group (a group which is capable of being easily converted into the functional group), during the steps from starting materials to intermediates. Examples of the protecting group include the protective groups as described in "Protective Groups in Organic Synthesis (3rd edition, 1999)", edited by Greene and Wuts, and the like, which may be appropriately selected and used depending on the reaction conditions. In these methods, a desired compound can be obtained by introducing the protecting group to carry out the reaction, and then, if desired, removing the protecting group.

Furthermore, another compound according to the present invention can also be prepared by further carrying out a method well-known to a person skilled in the art, such as common N-alkylation, reduction, oxidation, hydrolysis, and the like for the compound according to the present invention. For example, another compound according to the present invention can also be prepared by carrying out a reaction which can be employed for introduction of a group represented by —$R^3$ other than —H onto nitrogen by a person skilled in the art, such as common N-alkylation reactions, reductive amination reactions, and the like, for the compound (1c) or (1e) obtained in the first production process, the compound (2d) obtained in the second production process, the compound (3c) obtained in third production process, or the compound (4d) obtained in fourth production process. Further, the introduction of a group represented by —$R^3$ other than —H onto nitrogen can be conducted at a step during preparation of intermediates, or specifically, for example, the introduction can also be conducted at a step of the compound (3b) or the compound (4c).

Additionally, the prodrug of the compound according to the present invention can be prepared by introducing a specific group during the steps from starting materials to intermediates, in the same manner as for the above protecting groups, or by carrying out the reaction using the obtained compound according to the present invention. The reaction can be carried out by applying a method known by a person skilled in the art, such as general N-alkylation, esterification, amidation, dehydration, and the like.

Hereinbelow, typical production processes of the compound according to the present invention will be described. Each of the production processes can also be carried out with reference to the documents appended to the description herein. Further, the production process of the present invention is not limited to the examples as shown below. In addition, the compound according to the present invention having a skeleton not included in the typical production processes can be prepared based on the description in Preparative Examples and Examples as described later, or using a method in accordance with the description, or by a modified method thereof.

(First Production Process)

be used herein is not particularly limited, but examples thereof include alcohols such as methanol, ethanol, 2-propanol, and the like; water; aprotic polar solvents such as N,N-dimethyl formamide, N,N-dimethylacetamide, N-methylpyrrolidone, dimethylsulfoxide, and the like; and a mixed solvent thereof. The reaction is carried out at a hydrogen atmosphere of 1 atm to 5 atm.

(Step 2-1)

The present step is a step for preparing the compound according to the present invention in which $R^2$ is —H by cyclizing the compound (1b) obtained in the step 1 by a reductive amination reaction.

The reductive amination reaction is carried out by usually stirring for 0.1 hour to 5 hours in a solvent inert to the reaction at −45° C. to heating under reflux, preferably at 0° C. to room temperature, in the presence of a reducing agent. The solvent to be used herein is not particularly limited, but examples

[Chem. 7]

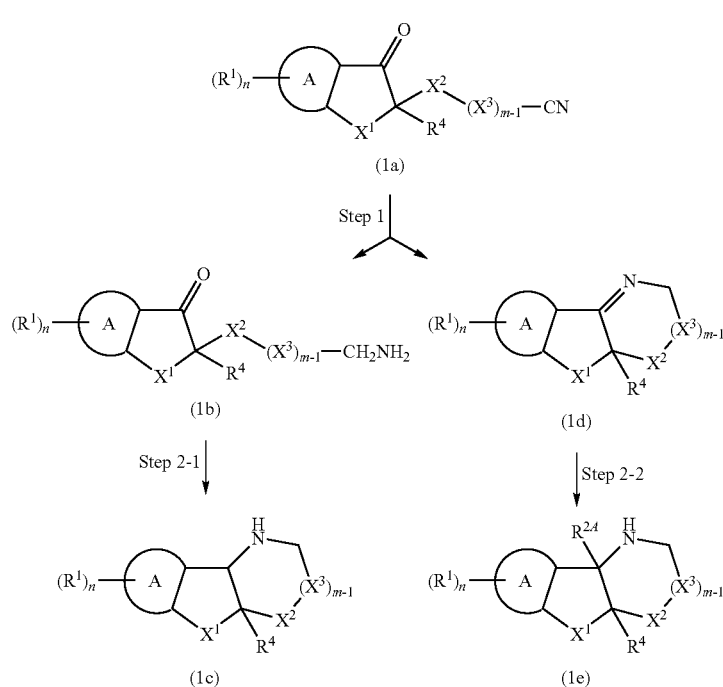

(The symbols in the formula represent the meanings as described above and $R^{2A}$ represents $C_{1-6}$ alkyl. The same shall apply hereinafter.)

The present production process is a method for preparing a compound (1c) or a compound (1e) by reducing a compound (1a) and carrying out a reductive amination or alkyl addition reaction for the obtained compound (1b) or compound (1d), respectively.

(Step 1)

The present step is a step for subjecting the compound (1a) to a reduction reaction, and either or both of two kinds of product, that is, the compound (1b) and the compound (1d) may be obtained in some cases. As a typical example of the reduction reaction of the present step, a reduction reaction by hydrogenation with a Raney Nickel catalyst can be exemplified.

The present reduction reaction is usually carried out by stirring for 1 hour to 120 hours in a solvent inert to the reaction from 0° C. to under heating, and preferably at 0° C. to room temperature, in the presence of a Raney nickel. The solvent to thereof include alcohols; ethers such as diethyl ether, tetrahydrofuran, dioxane, dimethoxy ethane, diglyme, and the like; halogenated hydrocarbons such as dichloromethane, chloroform, carbon tetrachloride, dichloroethane, and the like; or acetic acid; and a mixture thereof. Examples of the reducing agent include sodium cyanoborohydride, sodium triacetoxyborohydride, sodium borohydride, and the like. It is preferable in some cases to carry out the reaction in the presence of a dehydrating agent such as molecular sieves, and the like or an acid such as acetic acid, hydrochloric acid, a titanium (IV) isopropoxide complex, and the like. Depending on the reaction, the compound may be isolated as an imine intermediate, that is, as the compound (1d) in some cases, and the compound (1d) may be directly obtained in the step 1 in some cases. In such a case, an imine product can be reduced by a reducing agent such as sodium borohydride, lithium aluminum hydride, and the like to obtain a desired compound (1c). Further, instead of the treatment with a reducing agent, reduction in accordance with the step 1 of the first production process, or a reduction reaction using palladium-supported carbon instead of Raney nickel can be employed in a solvent such as alcohols, ethyl acetate, and the like in the presence or absence of an acid such as acetic acid, hydrochloric acid and the like.

(Step 2-2)

The present step is a step for preparing the compound according to the present invention in which $R^2$ is $C_{1-6}$ alkyl by subjecting the compound (1d) obtained as an intermediate of the step 1 or the step 2-1 to an alkyl addition reaction.

The alkyl addition reaction is carried out by allowing an alkyl additive to undergo a reaction and usually stirring for 0.1 hour to 5 hours in a solvent inert to the reaction from −78° C. to room temperature, preferably at −50° C. to 0° C., and if necessary, in the presence of a Lewis acid. The solvent to be used herein is not particularly limited, but examples thereof include ethers; saturated hydrocarbons such as hexane, pentane, heptane, and the like; aromatic hydrocarbons such as benzene, toluene, xylene, and the like; and a mixture thereof. Examples of the alkylating agent include alkyl lithium reagents such as methyl lithium, butyl lithium, and the like; Grignard reagents such as methyl magnesium bromide, ethyl magnesium chloride, and the like, and examples of the Lewis acid include a boron trifluoride diethyl ether complex, cerium chloride, magnesium bromide, and the like.

(Second Production Process)

[Chem. 8]

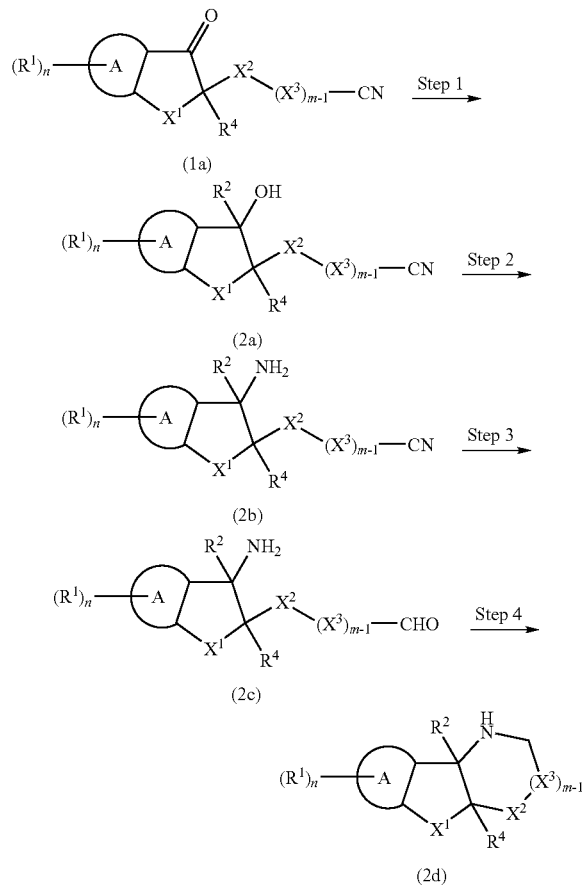

(The symbols in the formula represent the meanings as described above. The same shall apply hereinafter.)

The present production process is a method for preparing a compound (2d) by carrying out a reduction reaction or alkyl addition reaction of ketone for the compound (1a), converting the hydroxyl group of the obtained compound (2a) into an amino group, reducing the cyano group of the obtained compound (2b), and carrying out a reductive amination reaction for the obtained compound (2c).

(Step 1)

The present step is a step for carrying out a reduction reaction or alkyl addition reaction for the compound (1a).

The reduction reaction is carried out by allowing a reducing agent to undergo a reaction and usually stirring for 0.1 hour to 5 hours in a solvent inert to the reaction from −78° C. to under heating, preferably at 0° C. to room temperature. Examples of the solvent to be used herein include alcohols; ethers; aromatic hydrocarbons; and a mixed solvent thereof. Examples of the reducing agent include sodium borohydride, lithium borohydride, lithium aluminum hydride, and the like.

The alkyl addition reaction can be carried out in the same manner as in the step 2-2 of the first production process.

(Step 2)

The present step is a step for converting the hydroxyl group of the compound (2a) obtained in the step 1 into an amino group. Specifically, for example, an azidation reaction can be carried out, and subsequently a reduction reaction can be carried out for the compound (2a).

The azidation reaction is carried out by allowing an azidating agent to undergo a reaction and usually stirring for 0.1 hour to 5 hours in a solvent inert to the reaction, in the presence of an acid catalyst if necessary, and using an acid as a solvent as occasion demands, from −45° C. to heating under reflux, preferably at 0° C. to room temperature. The solvent to be used herein is not particularly limited, but examples thereof include halogenated hydrocarbons; aprotic polar solvent; ethers; aromatic hydrocarbons; and a mixture thereof. Examples of the acid catalyst include trichloroacetic acid, trifluoroacetic acid, a boron trifluoride diethyl ether complex, and the like, and examples of the azidating agent include sodium azide, lithium azide, trimethylsilyl azide, and the like.

Subsequently, the reduction reaction is carried out by allowing a phosphine compound to undergo a reaction and usually stirring for 1 hour to 24 hours in a solvent inert to the reaction, from 0° C. to heating under reflux, preferably at room temperature. The solvent to be used herein is not particularly limited, but examples thereof include alcohols; ethers; and a mixed solvent thereof with water, and the like. Examples of the phosphine compound include triphenyl phosphine and tributyl phosphine. Further, this reduction reaction can also be carried out by usually stirring for 1 hour to 24 hours in an inert solvent from 0° C. to heating under reflux, preferably at room temperature, in the presence of a catalytic reduction catalyst and a hydrogen source. The solvent to be used herein is not particularly limited, but examples thereof include alcohols; ethers; ethyl acetate, a mixed solvent thereof with water, and the like. Examples of the catalytic reduction catalyst include palladium-supported carbon, Raney nickel, platinum oxide, and the like, and examples of the hydrogen source include hydrogen, ammonium formate, and the like, under ambient pressure to under pressure. Furthermore, this reduction reaction can also be carried out by allowing a reducing agent such as lithium aluminum hydride, and the like to undergo a reaction in ethers; aromatic hydrocarbons as a solvent, from 0° C. to heating under reflux, preferably from room temperature to under warming.

(Step 3)

The present step is a step for subjecting the compound (2b) obtained in the step 2 to a reduction reaction.

The reduction reaction is carried out by allowing a reducing agent to undergo a reaction and usually stirring for 0.1 hour to 5 hours in a solvent inert to the reaction from −78° C. to room temperature, preferably at −50° C. to 0° C. The solvent to be used herein is not particularly limited, but examples thereof include ethers; aromatic hydrocarbons; and a mixed solvent thereof. As the reducing agent, diisobutyla-luminum hydride is suitably used.

(Step 4)

The present step is a step for preparing the compound according to the present invention by cyclizing the compound (2c) obtained in the step 3 by a reductive amination reaction.

The reductive amination reaction can be carried out in the same manner as in the step 2-1 of the first production process.

(Third Production Process)

[Chem. 9]

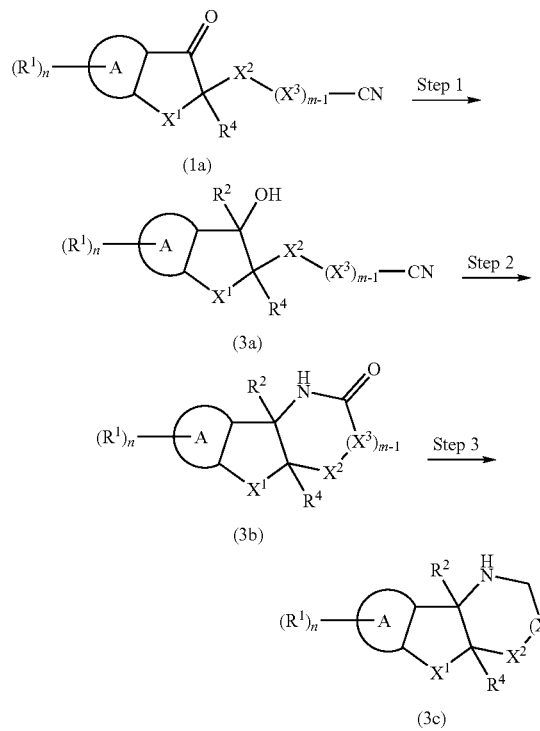

(The symbols in the formula represent the meanings as described above. The same shall apply hereinafter.)

The present production process is a method for preparing a compound (3c) by reducing the compound (1a), carrying out a cyclization reaction under an acidic condition for the obtained compound (3a), and reducing the obtained compound (3b).

(Step 1)

The present step is a step for subjecting the compound (1a) to a reduction reaction or an alkyl addition reaction.

The reduction reaction or the alkyl addition reaction can be carried out in the same manner as in the step 1 of the second production process.

(Step 2)

The present step is a step for carrying out a cyclization reaction under an acidic condition for the compound (3a) obtained in the step 1. Specifically, a Ritter reaction can be carried out for the compound (3a).

The Ritter reaction is carried out by usually stirring for 0.1 hour to 5 hours without a solvent or in a solvent inert to the reaction from −45° C. to heating under reflux, preferably from 0° C. to heating under reflux in the presence of an acid. The solvent to be used herein is not particularly limited, but examples thereof include acetic acid; acetic anhydride; ethers; aliphatic hydrocarbons; halogenated hydrocarbons; nitro benzene; and a mixture thereof. Examples of the acid to be used include sulfonic acids or hydrates thereof such as methanesulfonic acid, p-toluenesulfonic acid, trifluoromethanesulfonic acid, and the like; sulfuric acid; trifluoroacetic acid; perchloric acid; phosphoric acid; polyphosphoric acid; formic acid; and Lewis acids such as a boron trifluoride diethyl ether complex, trimethylsilyl triflate, and the like.

(Step 3)

The present step is a step for preparing the compound according to the present invention by subjecting the compound (3b) obtained in the step 2 to a reduction reaction.

The reduction reaction is carried out by allowing a reducing agent to undergo a reaction and usually stirring for 0.1 hour to 5 hours in a solvent inert to the reaction from −20° C. to heating under reflux, preferably from 0° C. to under heating. The solvent to be used herein is not particularly limited, but examples thereof include ethers; aromatic hydrocarbons; and a mixed solvent thereof. Examples of the reducing agent include lithium aluminum hydride, a borane/tetrahydrofuran complex, sodium bis(2-methoxyethoxy)aluminum hydride, and the like.

(Fourth Production Process)

[Chem. 10]

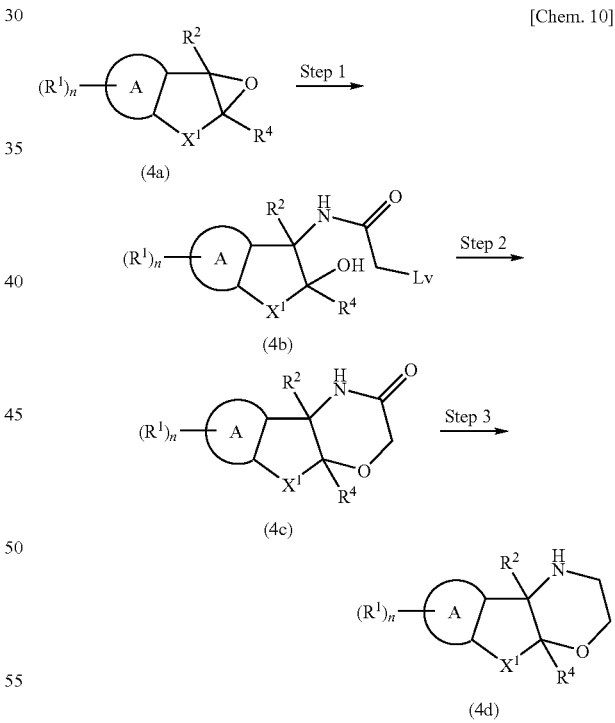

(The symbols in the formula represent the meanings as described above, and -Lv represents a leaving group. The same shall apply hereinafter.)

The present production process is a method for preparing the compound according to the present invention, in which $X^2$ is —O—, m is 2, $X^3$ is —C($R^C$)($R^D$)—, and $R^C$ and $R^D$ are both —H, that is a compound (4d), by carrying out a coupling reaction with a nitrile compound under an acidic condition for the compound (4a), subjecting the obtained compound (4b) to a ring-closure reaction, and subjecting the obtained compound (4c) to a reduction reaction.

Further, examples of the leaving group include chloro, bromo, hydroxy, methanesulfonyloxy, p-toluenesulfonyloxy, trifluoromethanesulfonyloxy, and the like.

(Step 1)

The present step is a step for carrying out a coupling reaction with a nitrile compound under an acidic condition for the compound (4a). Specifically, a Ritter reaction can be carried out for the compound (4a).

The Ritter reaction can be carried out in the same manner as in the step 2 of the third production process.

Further, examples of the nitrile compound used herein include chloroacetonitrile, bromoacetonitrile, and hydroxyacetonitrile.

(Step 2)

The present step is a step for subjecting the compound (4b) obtained in the step 1 to a ring-closure reaction.

Further, in the case of using hydroxyacetonitrile in the step 1, according to the reaction to be carried out in the present step, the hydroxyl group of the compound (4b) may be converted into methanesulfonyloxy, p-toluenesulfonyloxy, trifluoromethanesulfonyloxy, or the like, and then subjected to the reaction of the present step.

If the leaving group is chloro, bromo, methanesulfonyloxy, p-toluenesulfonyloxy, trifluoromethanesulfonyloxy, or the like, specifically, for example, an O-alkylation reaction can be employed, whereas if the leaving group is hydroxy, specifically, for example, a Mitsunobu reaction can be employed.

The O-alkylation reaction is carried out by usually stirring for 0.1 hour to 5 hours in a solvent inert to the reaction, from −20° C. to heating under reflux, preferably at 0° C. to room temperature in the presence of a base. The solvent to be used herein is not particularly limited, but examples thereof include ethers; aromatic hydrocarbons; aprotic polar solvents; alcohols and a mixed solvent thereof. Examples of the base include sodium methoxide, potassium t-butoxide, sodium hydride, potassium hydroxide, cesium carbonate, and the like.

The Mitsunobu reaction is carried out by usually stirring for 0.1 hour to 5 hours in a solvent inert to the reaction from 0° C. to heating under reflux, preferably at 0° C. to room temperature in the presence of a phosphorus compound and an azodicarbonyl compound. The solvent to be used herein is not particularly limited, but examples thereof include halogenated hydrocarbons; ethers; aromatic hydrocarbons; and a mixed solvent thereof. Examples of the phosphorus compound include tributyl phosphine, triphenyl phosphine, and the like, and examples of the azodicarbonyl compound include diethyl azodicarboxylate, 1,1'-(azodicarbonyl)dipiperidine, and the like. Instead of using an activator prepared from the phosphorus compound and the azodicarbonyl compound, a reagent such as cyanomethylenetributylphosphorane, and the like can also be used.

(Step 3)

The present step is a step for preparing the compound according to the present invention in which $X^2$ is —O—, m is 2, $X^3$ is —C($R^C$)($R^D$)—, and $R^C$ and $R^D$ are both —H by subjecting the compound (4c) obtained in the step 2 to a reduction reaction.

The reduction reaction can be carried out in the same manner as in the step 3 of the third production process.

(Production Process 1 for Intermediate)

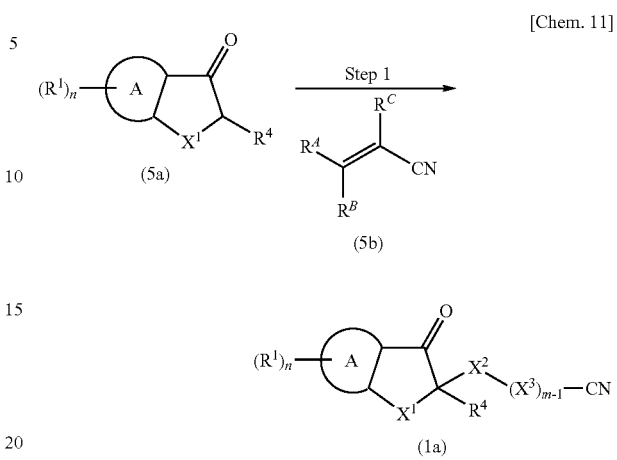

[Chem. 11]

(The symbols in the formula represent the meanings as described above. The same shall apply hereinafter.)

The present production process is a method for preparing the compound (1a) in which m is 1 and $X^2$ is —C($R^A$)($R^B$)— by allowing the compound (5a) to undergo a reaction with a base, and subjecting the compound (5b) to an addition reaction. Further, in order to introduce $R^D$ which is other than —H, the compound according to the present invention can be derived by reducing the carbonyl of the compound (1a), for example, by substituting with methoxy by methylation and then introducing by alkylation into the α-position of nitrile, subjecting the product to a Ritter reaction according to the step 2 of the third production process, and following the step 3 of the third production process.

(Step 1)

The present step is a step for allowing the compound (5a) to undergo a reaction with a base and subjecting the compound (5b) to an addition reaction. Specifically, a Michael addition reaction can be carried out.

The Michael addition reaction is carried out by usually stirring with acrylonitriles for 0.1 hour to 5 hours in a solvent inert to the reaction from −20° C. to heating under reflux, preferably at 0° C. to room temperature in the presence of a base. The solvent to be used herein is not particularly limited, but examples thereof include ethers; aromatic hydrocarbons; aprotic polar solvents; alcohols and a mixed solvent thereof. Examples of the base include sodium methoxide, potassium t-butoxide, sodium hydride, potassium hydroxide, and the like.

(Production Process 2 for Intermediate)

[Chem. 12]

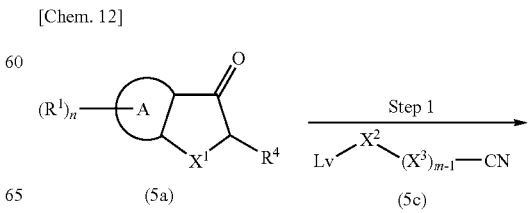

-continued

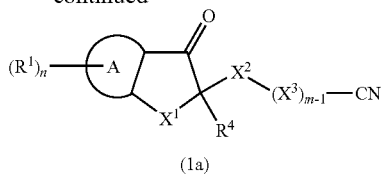

(1a)

(The symbols in the formula represent the meanings as described above. The same shall apply hereinafter.)

The present production process is a method for preparing the compound (1a) in which $X^2$ is —$C(R^A)(R^B)$— by allowing the compound (5a) to undergo a reaction with a base and subjecting the compound (5c) to an addition reaction.

(Step 1)

The present step is a step for allowing the compound (5a) to undergo a reaction with a base and subjecting the compound (5c) to an addition reaction.

The addition reaction is carried out by usually stirring with halogenated alkyls having a cyano group or sulfonyloxyalkyls for 0.1 hour to 5 hours in a solvent inert to the reaction from −78° C. to heating under reflux, preferably from −78° C. to room temperature in the presence of a base. The solvent to be used herein is not particularly limited, but examples thereof include ethers; aromatic hydrocarbons; aprotic polar solvents; alcohols and a mixed solvent thereof. Examples of the base include sodium methoxide, potassium t-butoxide, sodium hydride, potassium hydroxide, lithium diisopropyl amide, lithium hexamethyldisilazide, and the like.

The compound according to the present invention is isolated and purified as a free compound, pharmaceutically acceptable salts thereof, hydrates, solvates, or polymorphism thereof. The pharmaceutically acceptable salt of the compound according to the present invention can also be prepared in accordance with a conventional method for a salt formation reaction.

Isolation and purification are carried out by employing general chemical operations such as extraction, fractional crystallization, various types of fractional chromatography, and the like.

Various isomers can be separated by selecting an appropriate starting compound or by making use of the difference in the physicochemical properties between isomers. For example, the optical isomer can be obtained by general optical resolution methods of racemic compounds (for example, fractional crystallization for inducing diastereomer salts with optically active bases or acids, chromatography using a chiral column and the like, and others) and can also be prepared from an appropriate optically active starting compound.

The pharmacological activity of the compound according to the present invention was confirmed by the following test.

Text Example 1

MK-801 Binding Test

1) Preparation of Specimens of Rat Meninges

The whole brain was taken out from 30 10-week SD rats (Nippon SLC), and the cerebellum was removed. A 0.32 M aqueous sucrose solution was added to the part containing the cerebrum, followed by cutting by a mixer and homogenizing with a Teflon (registered trademark) homogenizer. After centrifugation at 2800 rpm at 4° C. for 15 minutes, the resulting supernatant was again centrifuged at 15000 g at 4° C. for 20 minutes. The pellets were suspended in 50 mM Tris-HCL (pH 7.5) containing 0.08% Triton X-100, and kept statically on ice for 30 minutes, then centrifuged at 15000 g at 4° C. for 20 minutes. The pellets were suspended in 50 mM Tris-HCl (pH 7.5) added thereto, and centrifuged at 15000 g at 4° C. for 20 minutes. 50 mM Tris-HCl (pH 7.5) was again added to the pellets, and centrifuged in the same manner as before. The pellets were resuspended in 20 ml of 50 mM Tris-HCl (pH 7.5) added thereto, and homogenized with the Teflon (registered trademark) homogenizer. The membrane specimen was dispensed portionwise into tubes and stored in a deep freezer (−80° C.). For use, this was washed twice with 5 mM Tris-HCl (pH 7.5) of five times the volume of the membrane specimen. After controlling the concentration at 1 mg protein/ml with 5 mM Tris-HCl (pH 7.5), it was used for assay.

2) [$^3$H] MK-801 Binding Assay

50 µl of the rat membrane specimen (1 mg protein/ml) was added to a solution of a test compound dissolved in 1 µl of dimethylsulfoxide. Then, 50 µl of a ligand solution (600 nM glutamate, 600 nM glycine, 8 nM [$^3$H] MK-801 (Perkin-Elmer) was added thereto and well stirred, followed by the reaction at room temperature for 45 minutes. Using Uni Filter Plate GF/B 96 (Perkin-Elmer) previously coated with 0.2% polyethyleneimine, the membrane specimen was collected, and the filter was well washed with 5 mM Tris-HCl (pH 7.5). 30 µl of Microscinti 20 (Perkin-Elmer) was added to the filter, and the radioactivity trapped on the filter was measured by a microplate scintillation counter (TopCount™; Beckman). Based on the MK-801 (final 1 µM) inhibition, 100%, of a control case of dimethylsulfoxide alone, the concentration of the compound for 50% inhibition, $IC_{50}$ was computed. Inhibition rate of MK-801 (final concentration: 1 µM) relative to the case in which dimethylsulfoxide alone was added was set to 100%, the concentration in which the test compound showed 50% inhibition rate was calculated as $IC_{50}$. The [$^3$H] MK-801 binding affinity for the rat membrane specimen was calculated to be Kd=1.6 nM through Scatchard analysis. The Ki value of the compound was computed according to the calculation equation: $Ki=IC_{50}/(1+$radioligand concentration (4 nM) in assay)/Kd value (1.6 nM)).

As a result, some of the compounds according to the present invention exhibited binding affinity for an NMDA receptor with 10 µM or less of a Ki value in the test above. The results of some of Example compounds in the present test are shown in Table 1.

TABLE 1

| Example No. | Ki/µM |
|---|---|
| 1 | 0.9 |
| 3 | 1.2 |
| 13 | 2.0 |
| 15 | 8.5 |
| 17 | 2.0 |
| 22 | 5.1 |
| 32 | 6.8 |
| 38-1 | 0.5 |
| 38-2 | 6.3 |
| 42 | 1.3 |
| 56 | 1.5 |
| 63 | 0.8 |
| 68 | 0.6 |
| 69 | 1.3 |
| 73 | 7.1 |
| 77 | 4.0 |
| 81 | 2.0 |
| 82 | 6.7 |
| 83-1 | 0.6 |
| 83-2 | 2.7 |
| 84-1 | 0.5 |
| 84-2 | 1.1 |
| Compound A | 38 |
| Compound B | 23 |
| Compound C | 20 |
| Compound F | 3.4 |

Further, in Table 1 and Text Examples below, Compound A, Compound B, Compound C, and Compound F each represent (4aRS,9bRS)-2,3,4,4a,5,9b-hexahydro-1H-indeno[1,2-b]pyridine, (4aRS,5RS,9bRS)-5-phenyl-2,3,4,4a,5,9b-hexahydro-1H-indeno[1,2-b]pyridine, (4aRS,5SR,9bRS)-5-phenyl-2,3,4,4a,5,9b-hexahydro-1H-indeno[1,2-b]pyridine, and (4aRS,9bRS)-1-methyl-4a-phenyl-2,3,4,4a,5,9b-hexahydro-1H-indeno[1,2-b]pyridine, each of which is a known compound having the following chemical structure.

[Chem. 13]

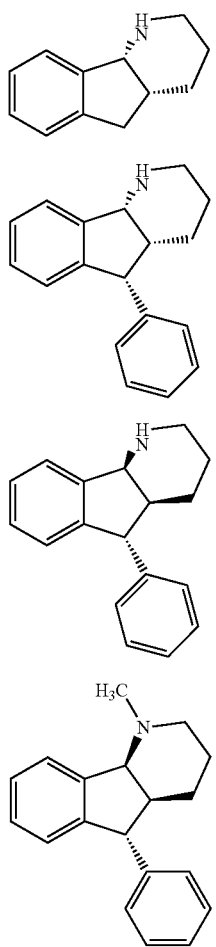

Compound A

Compound B

Compound C

Compound F

Text Example 2

Intracellular Calcium Concentration Determination Test by FLIPR (Fluorometric Imaging Plate Reader)

1) Preparation of Rat First-Generation Neurocytes

Anesthetized with ether, Wistar rats (Nippon SLC) at the 19th day of pregnancy were let die from blood loss by breast incision. The abdomen was cut open, and the womb was extracted, and the fetus was removed. The whole brain was removed, the hemicerebrum was then isolated in Neurobasal medium (Glu, Asp-free; Gibco), and the meninx was removed. The hemicerebrum was recovered by centrifugation, and suspended in a cell-dispersing solution (0.36 mg/ml papain, 150 U/ml DNase 1, 0.02% L-cysteine monohydrochloride monohydrate, 0.02% bovine serum albumin, 0.5% glucose, $Ca^{2+}$, $Mg^{2+}$-free PBS), and treated at 37° C. for 15 minutes. This was centrifuged at 400 g for 5 minutes, and the supernatant was removed by suction. This was suspended in a neurocyte culture medium (Sumitomo Bakelite), and the cell masses were removed using a filter. The number of the living cells was counted, and 100,000 cells/well were incubated on a 96-well plate (Biocoat PDL96W black/clear (Nippon Becton Dickinson)) (37° C., 5% $CO_2$).

2) Intracellular Calcium Concentration Determination by FLIPR (Fluorometric Imaging Plate Reader)

The culture medium of rat first-generation neurocytes (DIV7-9) was removed by suction, and the cells were washed once with a 100 μl assay buffer (Hank's Balanced Salt Solution ($Ca^{2+}$, $Mg^{2+}$-free), 20 mM Hepes-NaOH (pH 7.4), 1 mM $CaCl_2$). 100 μl of the assay buffer containing Fluo3 (Dojin Chemical) was added thereto, and incubated for 1 hour (37° C., 5% $CO_2$). The cells were washed three times with 100 μl of the assay buffer, and then a compound solution dissolved in 1 μl of dimethylsulfoxide, and 100 μl of the assay buffer containing 2.5 μM (final concentration) tetrodotoxin were added thereto and incubated for 30 minutes (37° C., 5% $CO_2$). The fluorescent intensity was measured at intervals of two seconds, and ten seconds after the measurement start, 50 μl of a ligand solution (Hank's Balanced Salt Solution ($Ca^{2+}$, $Mg^{2+}$-free), 20 mM Hepes-NaOH (pH 7.4), 1 mM $CaCl_2$, 9 μM NMDA, 30 μM glycine) containing the compound solution dissolved in 0.5 μl of dimethylsulfoxide was added thereto, and the fluorescent intensity was measured for 120 seconds from the start of the measurement. The data measured for total of 120 seconds (60 times in total) were averaged. Inhibition rate of 10 μM MK-801 relative to the case in which dimethylsulfoxide alone was added was set to 100%, the concentration in which the compound showed 50% inhibition rate was calculated as $IC_{50}$.

As a result, some of the compounds according to the present invention exhibited an NMDA receptor antagonistic action with 100 μM or less of $IC_{50}$ values in the test above. The results of some of Example compounds in the present test are shown in Table 2.

TABLE 2

| Example No. | $IC_{50}$/μM |
|---|---|
| 1 | 5.1 |
| 3 | 6.8 |
| 22 | 34 |
| 63 | 3.0 |
| 81 | 21 |
| 82 | 94 |
| 83-1 | 3.1 |
| 83-2 | 12 |
| 84-1 | 1.8 |
| 84-2 | 6.1 |

Text Example 3

MES (Maximal Electroshock Seizure) Inhibitory Action

A test compound was orally administered to a male ddy mouse, an inhibitory action on the seizures caused by an electroshock applied at 30 minutes later (Interval 10 ms, Duration 0.9 ms, Amplitude 50 mA, Gate 0.2 s) was evaluated, and an NMDA receptor inhibitory action in vivo was measured (Palmer G C, Harris E W, Ray R, Stagnitto M L, Schmiesing R J. Arch Int Pharmacodyn Ther. 1992 May-June; 317: 16-34).

As a result, some of the compounds according to the present invention exhibited an anti-seizure action with an $ED_{50}$ value of 50 mg/kg or less in the test above. The results of some of the Example compounds in the present test are shown in Table 3. Further, known compounds Compound A and Compound F did not exhibit an anti-seizure action even at 80 mg/kg and 100 mg/kg, respectively.

TABLE 3

| Example No. | $ED_{50}$ mg/kg, po |
|---|---|
| 1 | 6.8 |
| 3 | 39 |
| 13 | 14 |
| 15 | 38 |
| 17 | 4.2 |
| 22 | 11 |
| 32 | 26 |
| 42 | 31 |
| 63 | 5.8 |
| 68 | 26 |
| 81 | 9.1 |
| 82 | 19 |
| 83-1 | 6.2 |
| 84-1 | 4.2 |
| 84-2 | 28 |
| Compound A | >80 |
| Compound F | >100 |

Text Example 4

Y-Maze Test Using Magnesium-Deficient Mouse

A learning disorder improvement action of a test compound on a learning disorder caused by magnesium deficiency (Bardgett M E, Schultheis P J, McGill D L, Richmond R E, Wagge J R. Magnesium deficiency impairs fear conditioning in mice. Brain Res 2005; 1038:100-6.) can be evaluated by a Y-maze test (Maurice T, Privat A. SA4503, a novel cognitive enhancer with al receptor agonist properties, facilitates NMDA receptor-dependent learning in mice. Eur J Pharmacol 1997; 328:9-18).

As a result of the tests as described above, it was confirmed that the compound according to the present invention or a pharmaceutically acceptable salt thereof has an NMDA receptor inhibitory action and thus can be used as a prophylactic and/or therapeutic agent for Alzheimer's disease, cerebrovascular dementia, Parkinson's disease, ischemic apoplexy, pain, intractable depression, attention deficit hyperactivity disorder, migraines, schizophrenia, generalized anxiety disorder, obsessive-compulsive disorder, autism, bulimia, drug addiction, or the like.

A pharmaceutical composition containing one or two or more kinds of the compound according to the present invention as an active ingredient can be prepared in accordance with a generally used method, using a pharmaceutical excipient, a pharmaceutical carrier, or the like, that is usually used in the art.

The administration can be carried out in any form of oral administration via tablets, pills, capsules, granules, powders, liquid preparations, or the like; or parenteral administration via injections such as intraarticular, intravenous, or intramuscular injections, suppositories, eye drops, eye ointments, percutaneous liquid preparations, ointments, percutaneous patches, transmucosal liquid preparations, transmucosal patches, inhalations, and the like.

As the solid composition for oral administration, tablets, powders, granules, or the like are used. In such a solid composition, one or two or more kinds of active ingredients are mixed with at least one inert excipient such as lactose, mannitol, glucose, hydroxypropylcellulose, microcrystalline cellulose, starch, polyvinyl pyrrolidone, and/or magnesium aluminometasilicate. According to a conventional method, the composition may contain inert additives such as a lubricant such as magnesium stearate, a disintegrator such as carboxymethylstarch sodium, a stabilizing agent, and a solubilizing agent. As occasion demands, the tablets or the pills may be coated with a sugar coating, or a film of a gastric or enteric material.

The liquid composition for oral administration includes pharmaceutically acceptable emulsions, solutions, suspensions, syrups, elixirs, or the like, and contains a generally used inert diluent such as purified water or ethanol. In addition to the inert diluent, this liquid composition may contain an auxiliary agent such as a solubilizing agent, a moistening agent, and a suspending agent, a sweetener, a flavor, an aroma, and an antiseptic.

The injections for parenteral administration include sterile aqueous or non-aqueous liquid preparations, suspensions and emulsions. The aqueous solvent includes, for example, distilled water for injection and physiological saline. Examples of the non-aqueous solvent include propylene glycol, polyethylene glycol, plant oils such as olive oil, alcohols such as ethanol, Polysorbate 80 (Japanese Pharmacopeia), and the like. Such a composition may further contain a tonicity agent, an antiseptic, a moistening agent, an emulsifying agent, a dispersing agent, a stabilizing agent, or a solubilizing agent. These are sterilized, for example, by filtration through a bacteria retaining filter, blending of a bactericide, or irradiation. Additionally, these can also be used by preparing a sterile solid composition, and dissolving or suspending it in sterile water or a sterile solvent for injection prior to its use.

The agent for external use includes ointments, plasters, creams, jellies, cataplasms, sprays, lotions, eye drops, eye ointments, and the like. The agents contain generally used ointment bases, lotion bases, aqueous or non-aqueous liquid preparations, suspensions, emulsions, and the like. Examples of the ointment bases or the lotion bases include polyethylene glycol, propylene glycol, white vaseline, bleached bee wax, polyoxyethylene hydrogenated castor oil, glyceryl monostearate, stearyl alcohol, cetyl alcohol, lauromacrogol, sorbitan sesquioleate, and the like.

As the transmucosal agents such as an inhalation, a transnasal agent, and the like, those in the form of a solid, liquid, or semi-solid state are used, and can be prepared in accordance with a conventionally known method. For example, a known excipient, and also a pH adjusting agent, an antiseptic, a surfactant, a lubricant, a stabilizing agent, a thickening agent, or the like may be appropriately added thereto. For their administration, an appropriate device for inhalation or blowing can be used. For example, a compound may be administered alone or as a powder of formulated mixture, or as a solution or suspension in combination with a pharmaceutically acceptable carrier, using a conventionally known device or sprayer, such as a measured administration inhalation device, and the like. A dry powder inhaler or the like may be for single or multiple administration use, and a dry powder or a powder-containing capsule may be used. Alternatively, this may be in a form such as a pressurized aerosol spray which uses an appropriate propellant, for example, a suitable gas such as chlorofluoroalkane, hydrofluoroalkane, carbon dioxide, and the like, or other forms.

In oral administration, the daily dose is generally from about 0.001 to 100 mg/kg, preferably from 0.1 to 30 mg/kg, and more preferably 0.1 to 10 mg/kg, per body weight, administered in one portion or in 2 to 4 divided portions. In the case of intravenous administration, the daily dose is suitably administered from about 0.0001 to 10 mg/kg per body weight, once a day or two or more times a day. Additionally, a transmucosal agent is administered at a dose from about 0.001 to 100 mg/kg per body weight, once a day or two or more times a day. The dose is appropriately decided in response to the individual case by taking the symptoms, the age, and the gender, and the like into consideration.

The compound according to the present invention can be used in combination with various agents for treating or preventing the diseases for which the compound according to the present invention is considered to be effective. The combined preparation may be administered simultaneously, or separately and continuously or at a desired time interval. The preparations to be co-administered may be a blend, or may be prepared individually.

EXAMPLES

Hereinbelow, the production processes for compounds according to the present invention will be described in more detail with reference to Examples. Further, the present invention is not limited to the compounds described in the Examples below. Furthermore, the production processes for the starting compounds will be described in Preparative Examples. Further, the production processes for the compound according to the present invention are not limited to the production processes of the specific Examples as below, but the compound according to the present invention can also be prepared by a combination of the production processes or the methods that are apparent to a person skilled in the art.

In addition, the following abbreviations may be used sometimes in Examples, Preparative Examples, and Tables to be described later.

Px: Preparative Example number, Ex: Example number, STRUCTURE: Chemical structural formula (also, among the compounds shown in stereochemistry, one denoted by "chiral" represents a compound having such a steric configuration, and the other compounds represent racemic), Sal: salt (representing the compound was isolated as the following salts. CL: hydrochloride, BR: bromohydride, MS: methanesulfonate, OX: oxalate, FM: fumarate. Further, a blank or no description means that the compound was isolated as a free form.), Syn: production process (the numeral shows that the compound was prepared in the same production process as in the compound having its number as the Preparative Example number or Example number in the section), Data: physical data (which represents the analyzer data below of the compound. CI+: CI[M+H]$^+$, EI+: EI[M]$^+$, FAB+: FAB-MS[M+H]$^+$, ESI+: ESI-MS[M+H]$^+$, APCI+: APCI-MS[M+H]$^+$, NMR-DMSOd6: δ (ppm) of the peaks in $^1$H-NMR in dimethylsulfoxide-$d_6$, NMR-CDCl3: δ (ppm) of the peaks in $^1$H-NMR in CDCl$_3$, NMR-CD3OD: δ (ppm) of the peaks in $^1$H-NMR in CD$_3$OD. In addition, for some compounds, characteristic peaks only are described).

Further, in Tables, for Example 79-1 and Example 79-2, Example 80-1 and Example 80-2, Example 83-1 and Example 83-2, and Example 84-1 and Example 84-2, absolute arrangement is not determined, respectively, but each represents either different compounds.

Preparative Example 1

To a solution of 2-methylindan-1-one (100 g) in 2-propanol (1 L) was added potassium tert-butoxide (15.4 g) under ice-cooling, followed by stirring for 30 minutes, and acrylonitrile (36.5 g) was then added dropwise thereto over 30 minutes. The reaction liquid was further stirred for 30 minutes under ice-cooling, and a saturated aqueous ammonium chloride solution was then added thereto. The mixture was extracted with ethyl acetate, the organic layer was washed with water and saturated brine, and dried over anhydrous magnesium sulfate, and the solvent was then evaporated under reduced pressure to obtain the compound of Preparative Example 1 (132 g) as a pale yellow oily substance.

Preparative Example 2

2-Ethylindan-1-one (1.6 g) and potassium tert-butoxide (560 mg) were dissolved in tert-butanol (20 ml), and acrylonitrile (663 mg) was added thereto at room temperature. After stirring at the same temperature for 2 hours, 1 M hydrochloric acid was added thereto, followed by extraction with ethyl acetate. The organic layer was washed with saturated brine and dried over anhydrous magnesium sulfate, and the solvent was then evaporated under reduced pressure. The residue was purified by silica gel column chromatography (eluent; n-hexane:ethyl acetate=4:1) to obtain the compound of Preparative Example 2 (1.92 g) as a pale yellow oily substance.

Preparative Example 3

The compound of Preparative Example 109 (3.04 g) was dissolved in tetrahydrofuran (30 ml) and tert-butanol (15 ml), and potassium tert-butoxide (300 mg) and acrylonitrile (1.5 ml) were added thereto under ice-cooling, followed by stirring at the same temperature for 1 hour and further at room temperature for 15 hours. To the reaction liquid was added a saturated aqueous ammonium chloride solution, followed by extraction with ethyl acetate, the organic layer was washed with water and saturated brine, dried over magnesium sulfate, and the solvent was then evaporated under reduced pressure. The residue was purified by silica gel column chromatography (eluent; n-hexane:ethyl acetate=4:1) to obtain the compound of Preparative Example 3 (1.45 g) as an oily substance.

Preparative Example 19

To a solution of the compound of Preparative Example 1 (132 g) in methanol (700 ml) was added portionwise sodium borohydride (12.6 g) under ice-cooling. After stirring at the same temperature for 1 hour, acetone was added thereto, followed by stirring for 1 hour further. The solvent was evaporated under reduced pressure, and a saturated aqueous ammonium chloride solution was then added thereto, followed by extraction with ethyl acetate. The organic layer was subsequently washed with a saturated aqueous ammonium chloride solution (400 ml), twice with water (400 ml), and with saturated brine (200 ml). After drying over anhydrous magnesium sulfate, the solvent was evaporated under reduced pressure to obtain the compound of Preparative Example 19 (131 g) as a colorless amorphous.

Preparative Example 20

To a solution of the compound of Preparative Example 2 (1.92 g) in methanol (30 ml) was added sodium borohydride (340 mg), followed by stirring at room temperature for 1 hour. Acetone was added thereto, the reaction solution was concentrated under reduced pressure, and a saturated aqueous ammonium chloride solution was then added thereto, followed by extraction with ethyl acetate. The organic layer was washed with saturated brine and dried over anhydrous magnesium sulfate, and the solvent was then evaporated under reduced pressure and concentrated under reduced pressure to obtain the compound of Preparative Example 20 (1.93 g) as a colorless oily substance.

Preparative Example 21

The compound of Preparative Example 3 (258 mg) was dissolved in tetrahydrofuran (2.0 ml) and methanol (2.0 ml), and sodium borohydride (40 mg) was added thereto under ice-cooling, followed by stirring at the same temperature for 2 hours. To the reaction solution were added water and a saturated aqueous ammonium chloride solution, followed by extraction with ethyl acetate, and the organic layer was washed with saturated brine and then dried over anhydrous magnesium sulfate. The solvent was evaporated under reduced pressure to obtain the compound of Preparative Example 21 (260 mg) as a yellow oily substance.

Preparative Example 38

A solution of methanesulfonic acid (23.5 g) in 1,2-dichloroethane (640 ml) was warmed to 80° C., followed by stirring, and a solution of the compound of Preparative Example 19 (32.8 g) in 1,2-dichloroethane (180 ml) was added dropwise thereto over 30 minutes. After stirring at the same temperature for further 1 hour, the reaction solution was ice-cooled, and ice water (200 ml), a 1 M aqueous sodium hydroxide solution (200 ml), and a saturated aqueous sodium hydrogen carbonate solution were subsequently added thereto, followed by extraction with chloroform. The organic layer was dried over anhydrous magnesium sulfate, the solvent was evaporated under reduced pressure, and the residue was then solidified by adding diisopropyl ether to obtain the compound of Preparative Example 38 (18.3 g) as a colorless powder.

Preparative Example 39

To a solution of the compound of Preparative Example 20 (1.93 g) in 1,2-dichloroethane (120 ml) was added methanesulfonic acid (870 mg), followed by stirring at 80° C. for 2 hours. After ice-cooling, a 1 M aqueous sodium hydroxide solution was added thereto for neutralization, followed by extraction with chloroform. The organic layer was dried over anhydrous magnesium sulfate, the solvent was evaporated under reduced pressure, and the residue was crystallized from diisopropyl ether to obtain the compound of Preparative Example 39 (879 mg) as a colorless powder.

Preparative Example 40

To a solution of methanesulfonic acid (0.1 ml) in 1,2-dichloroethane (15 ml) were added dropwise a solution of the compound of Preparative Example 21 (255 mg) in 1,2-dichloroethane (5.0 ml) at 80° C. over 20 minutes. After stirring at the same temperature for 3 hours, the reaction solution was neutralized by adding a 1 M aqueous sodium hydroxide solution under ice-cooling, and extracted with chloroform. The organic layer was washed with saturated brine and dried over anhydrous magnesium sulfate, the solvent was then evaporated under reduced pressure, and the residue was purified by silica gel column chromatography (eluent; chloroform/methanol) to obtain the compound of Preparative Example 40 (170 mg) as a colorless amorphous.

Preparative Example 56

To a solution of cis-1,2,3,4,4a,9a-hexahydro-9H-fluoren-9-one (1.4 g) and 2-bromoethylmethyl ether in tetrahydrofuran (20 ml) was added sodium iodide (1.1 g), and 55% oily sodium hydride (655 mg) was then added thereto, followed by stirring at room temperature for 5 days. Water was added thereto, followed by extraction with ethyl acetate, the organic layer was washed with saturated brine and washed with anhydrous magnesium sulfate, and the solvent was then evaporated under reduced pressure. The residue was purified by silica gel column chromatography (eluent; n-hexane:ethyl acetate=20:1) to obtain the compound of Preparative Example 56 (808 mg) as a pale yellow oily substance.

Preparative Example 59

To a solution of the compound of Preparative Example 56 (808 mg) in methylene chloride (10 ml) was added a solution of 1 M boron tribromide in methylene chloride (6.6 ml), followed by stirring at room temperature for 3 hours. Water was added thereto, followed by extraction with ethyl acetate, the organic layer was washed with water and saturated brine, and dried over anhydrous magnesium sulfate, and the solvent was then evaporated under reduced pressure. The residue was dissolved in N,N-dimethyl formamide (10 ml), and sodium azide (430 mg) was added thereto, followed by stirring at room temperature for 3 days. Water was added thereto, followed by extraction with ethyl acetate, the organic layer was washed with saturated brine and dried over anhydrous magnesium sulfate, and the solvent was then evaporated under reduced pressure. The residue was purified by silica gel column chromatography (eluent; n-hexane:ethyl acetate=20:1) to obtain the compound of Preparative Example 59 (844 mg) as a colorless oily substance.

Preparative Example 62-1 and Preparative Example 62-2

To a solution of the compound of Preparative Example 59 (600 mg) in diethyl ether (3.6 ml) was added tri-n-butyl phosphine (476 mg), followed by stirring at room temperature for 1 hour. Under ice-cooling, a solution of 1 M methyl lithium in diethyl ether (7.1 ml) and a solution of a boron trifluoride diethyl ether complex (0.60 ml) in diethyl ether (3.0 ml) were sequentially added thereto. After stirring at the same temperature for 3 hours, a saturated aqueous sodium hydrogen carbonate solution was added thereto, followed by extraction with chloroform. The organic layer was dried over anhydrous magnesium sulfate, the solvent was then evaporated under reduced pressure, and the residue was purified by silica gel column chromatography (eluent; chloroform:methanol:saturated aqueous ammonia=10:1:0.1) to obtain an oily substance (212 mg).

This was dissolved in pyridine (5 ml), and benzyl chloroformate (400 mg) was added thereto, followed by stirring at 50° C. overnight. The reaction solution was concentrated under reduced pressure and the residue was purified by silica gel column chromatography (eluent; n-hexane:ethyl acetate=4:1) to obtain the compound of Preparative Example 62-1 (40 mg) and the compound of Preparative Example 62-2 (30 mg), respectively, as a colorless oily substance.

Preparative Example 63-1 and Preparative Example 63-2

To a solution of the compound of Preparative Example 61 (630 mg) in diethyl ether (7 ml) was added tri-n-butyl phosphine, followed by stirring at room temperature for 1 hour. Then, a solution of 1 M methyl lithium in diethyl ether (6.8 ml) and a boron trifluoride diethyl ether complex (0.576 ml) were added thereto under ice-cooling, followed by stirring at the same temperature for 3 hours. After completion of the reaction, a saturated aqueous sodium hydrogen carbonate solution was added thereto, followed by extraction with chloroform, the organic layer was dried over anhydrous magnesium sulfate, and the solvent was evaporated under reduced pressure. The residue was purified by silica gel column chromatography (eluent; n-hexane:ethyl acetate=2:1, chloroform:methanol:saturated aqueous ammonia=10:1:0.1) to obtain the compound of Preparative Example 63-2 (135 mg) and an oily substance (306 mg).

Then, this oily substance was dissolved in pyridine (5 ml), and benzyl chloroformate (0.324 ml) was added thereto under ice-cooling, followed by warming to 80° C. and stirring for 3 days. The reaction solution was concentrated under reduced pressure and the residue was purified by silica gel column chromatography (eluent; n-hexane:ethyl acetate=4:1) to obtain the compound of Preparative Example 63-1 (95 mg) as a colorless oily substance.

Preparative Example 64

To a solution of 2-methylindan-1-one (4.5 g) in N,N-dimethyl formamide (25 ml) was added 55% oily sodium hydride (1.34 g) under ice-cooling, followed by stirring at the same temperature for 30 minutes. On the other hand, 4-bromobutanenitrile (6.15 g) and sodium iodide (6.22 g) was stirred in N,N-dimethyl formamide (25 ml) at room temperature for 30 minutes. This reaction mixture was added to the above-described reaction solution under ice-cooling, followed by stirring at the same temperature for 2 hours. To the reaction mixture was added a saturated aqueous ammonium chloride solution, followed by extraction with ethyl acetate, and the organic layer was washed with water and saturated brine. After drying over anhydrous magnesium sulfate, the solvent was evaporated under reduced pressure, and the residue was purified by silica gel column chromatography (eluent; n-hexane:ethyl acetate=4:1) to obtain the compound of Preparative Example 64 (3.31 g) as an oily substance.

Preparative Example 65

To a suspension of Raney nickel (440 mg) that had been sufficiently washed with water was added methanol (20 ml), and a solution of the compound of Preparative Example 64 (1.6 g) in methanol (20 ml) was then added thereto. The mixture was stirred at room temperature for 3 days at normal pressure under a hydrogen atmosphere. The reaction mixture was filtered through Celite, the filtrate was concentrated under reduced pressure, and the residue was purified by basic silica gel column chromatography (eluent; ethyl acetate) to obtain the compound of Preparative Example 65 (494 mg) as a colorless oily substance.

Preparative Example 66

To a mixed solution of the compound of Preparative Example 26 (1.12 g) and methyl iodide (0.48 ml) in N,N-dimethyl formamide (20 ml) was added 55% oily sodium hydride (269 mg) under ice-cooling, followed by stirring at the same temperature for 1 hour. To the reaction solution was added a saturated aqueous ammonium chloride solution, followed by extraction with ethyl acetate, the organic layer was washed with water and saturated brine, and dried over anhydrous magnesium sulfate, and the solvent was then evaporated under reduced pressure. The residue was purified by silica gel column chromatography (eluent; n-hexane:ethyl acetate=4:1) to obtain the compound of Preparative Example 66 (1.12 g) as a colorless oily substance.

Preparative Example 67

To a solution of diisopropyl amine (0.97 ml) in tetrahydrofuran (10 ml) was added a solution of 1.58 M n-butyl lithium in tetrahydrofuran (4.38 ml) at 0° C., followed by stirring at the same temperature for 30 minutes. Then, the compound of Preparative Example 66 (1.06 g) was added thereto, followed by stirring for further 2 hours. Methyl iodide (0.862 ml) was added thereto, followed by stirring at room temperature for further 2 hours. The reaction solution was added with a saturated aqueous ammonium chloride solution, extracted with ethyl acetate, and then washed with saturated brine. After drying over anhydrous magnesium sulfate, the solvent was evaporated under reduced pressure. Then, the residue was dissolved in 1,2-dichloroethane (100 ml), and methanesulfonic acid (0.30 ml) was added thereto under stirring under heating at 80° C. for 3 hours. The reaction solution was cooled, added with a 1 M aqueous sodium hydroxide solution, extracted with chloroform, and then dried over anhydrous magnesium sulfate, and the solvent was evaporated under reduced pressure. The residue was purified by silica gel column chromatography (eluent; chloroform:methanol=20:1) to obtain the compound of Preparative Example 67 (718 mg) as a yellow amorphous.

Preparative Example 68

To a solution of the compound of Preparative Example 1 (35.8 g) in tetrahydrofuran (200 ml) was added a solution of a 1 M methyl magnesium bromide in tetrahydrofuran (215 ml) at −78° C., followed by stirring over 4 hours, slowly warming to room temperature, and further stirring at room temperature overnight. A saturated ammonium chloride solution was added thereto, followed by extraction with ethyl acetate, the organic layer was washed with saturated brine and then dried over anhydrous magnesium sulfate, and the solvent was evaporated under reduced pressure. The residue was purified by silica gel column chromatography (eluent; n-hexane:ethyl acetate=4:1) to obtain the compound of Preparative Example 68 (29.0 g) as a yellow oily substance.

Preparative Example 69

To a suspension of the compound of Preparative Example 68 (9.3 g) and sodium azide (7.0 g) in chloroform (200 ml) was added trifluoroacetic acid (8.4 ml) under ice-cooling. After stirring at the same temperature for 1 hour, to the reaction solution was added a 10% aqueous ammonia solution, followed by extraction with ethyl acetate. The organic layer was washed with saturated brine and dried over anhydrous magnesium sulfate, and the solvent was then evaporated under reduced pressure. Then, the residue was dissolved in methanol (200 ml), and 10% palladium-supported carbon (700 mg) was added thereto, followed by stirring overnight at normal pressure under a hydrogen atmosphere. The reaction mixture was filtered through Celite and the filtrate was concentrated under reduced pressure. The residue was dissolved in ethyl acetate and extracted with 1 M hydrochloric acid (100 ml). The aqueous layer was alkalified by adding a 1 M aqueous sodium hydroxide solution and then extracted with chloroform. The organic layer was dried over anhydrous magnesium sulfate and then concentrated under reduced pressure. The residue was purified by silica gel column chromatography (eluent; chloroform:methanol:saturated aqueous ammonia=20:1:0.1) to obtain the compound of Preparative Example 69 (2.15 g) as a colorless oily substance.

Preparative Example 70-1 and Preparative Example 70-2

To a solution of the compound of Preparative Example 69 (6.45 g) in toluene (100 ml) was added a solution of 0.99 M diisobutylaluminum hydride in toluene (76 ml) at −78° C. The reaction liquid was slowly warmed to −35° C. over 3 hours, and methanol (10 ml) was then added thereto. In addition, a saturated aqueous ammonium chloride solution was added thereto under ice-cooling, followed by stirring at room temperature for 1 hour and filtering through Celite, the filtrate was concentrated under reduced pressure. The residue (6.0 g) was dissolved in 1,2-dichloroethane (600 ml), and titanium tetraisopropoxide (8.9 ml) was added thereto, followed by stirring at room temperature for 1 hour. Sodium triacetoxyborohydride (12.7 g) was added thereto, followed by stirring at room temperature overnight. The reaction liquid was poured into a 4 M aqueous sodium hydroxide solution added with ice, and then filtered through Celite, and the filtrate was extracted with chloroform. The organic layer was dried over anhydrous magnesium sulfate and the solvent was then evaporated under reduced pressure. The residue was dissolved in chloroform (100 ml), and a saturated aqueous sodium hydrogen carbonate solution was added thereto and then benzyl chloroformate (6.7 g) was added thereto, followed by stirring at room temperature for 3 hours. The reaction solution was extracted with chloroform, the organic layer was dried over anhydrous magnesium sulfate, and the solvent was then evaporated under reduced pressure. The residue was purified by silica gel column chromatography (eluent; n-hexane:ethyl acetate=20:1) to obtain the compound of Preparative Example 70-1 (1.97 g) and the compound of Preparative Example 70-2 (1.72 g), respectively, as a colorless oily substance.

Preparative Example 71

To a solution of 2-methylindan-1-one (1.02 g) in tetrahydrofuran (15 ml) was added a solution of 1 M lithium hexamethyl disilazide in tetrahydrofuran (8.4 ml) at −70° C., followed by stirring at the same temperature for 30 minutes. Subsequently, 2-(3-bromopropyl)-1H-isoindole-1,3(2H)-dione (2.23 g) was added thereto, followed by further stirring at the same temperature for 1 hour. The reaction solution was warmed to 0° C., and a saturated aqueous ammonium chloride solution was then added thereto, followed by extraction with ethyl acetate. The organic layer was washed with a saturated aqueous sodium hydrogen carbonate solution and saturated brine, and then, dried over anhydrous sodium sulfate, and the solvent was evaporated under reduced pressure. The residue was purified by silica gel column chromatography (eluent; n-hexane:ethyl acetate=10:1-1:1) to obtain the compound of Preparative Example 71 (422 mg) as a pale yellow solid.

Preparative Example 72-1 and Preparative Example 72-2

To a solution of 6a-methyl-6,6a-dihydro-1aH-indeno[1,2-b]oxirene (5.5 g) and chloroacetonitrile (20 ml) was added methanesulfonic acid (5.0 ml) under ice-cooling, followed by stirring at the same temperature for 1 hour and then stirring at room temperature for 6 hours. The reaction mixture was poured into ice water, followed by stirring for 30 minutes and extraction with ethyl acetate, and the organic layer was washed with a saturated aqueous sodium chloride solution, and then dried over magnesium sulfate. The solvent was evaporated under reduced pressure and the residue was purified by silica gel column chromatography (eluent; chloroform) to obtain the compound of Preparative Example 72-1 (2.73 g) as a colorless solid, and further the compound of Preparative Example 72-2 (0.49 g) as a pale brown solid, respectively.

Preparative Example 73

To a suspension of 55% oily sodium hydride (500 mg) in tetrahydrofuran (75 ml) was added dropwise a solution of the compound of Preparative Example 72-1 (500 mg) in tetrahydrofuran (75 ml) at 80° C. over 2 hours, followed by stirring at the same temperature for 1 hour. The reaction solution was cooled, water and a saturated aqueous ammonium chloride solution were added thereto, followed by extraction with ethyl acetate, and the organic layer was washed with a saturated aqueous sodium chloride solution. After drying over anhydrous magnesium sulfate, the solvent was evaporated under reduced pressure to obtain the compound of Preparative Example 73.

Preparative Example 75

To a solution of 3-(1-oxo-2,3-dihydro-1H-inden-2-yl)propanenitrile (724 mg) in methanol (10 ml) was added sodium borohydride (148 mg) under ice-cooling, followed by stirring at the same temperature for 1 hour. To the reaction solution was added a saturated aqueous ammonium chloride solution, followed by extraction with ethyl acetate. The organic layer was washed with saturated brine and dried over anhydrous magnesium sulfate, and the solvent was evaporated under reduced pressure. Then, the residue was dissolved in 1,4-dioxane (20 ml), and pyridinium p-toluenesulfonate (500 mg) was added thereto, followed by heating under stirring at 100° C. for 3 days. The reaction solution was cooled, and a saturated aqueous sodium hydrogen carbonate solution was then added thereto, followed by extraction with ethyl acetate. The organic layer was washed with 1 M hydrochloric acid and saturated brine. After drying over anhydrous magnesium sulfate, the solvent was evaporated under reduced pressure to obtain the compound of Preparative Example 75 (575 mg) as a colorless oily substance.

Preparative Example 76

To a solution of the compound of Preparative Example 75 (575 mg) in chloroform (20 ml) were added sodium hydrogen carbonate (856 mg) and 75% 3-chloroperbenzoic acid (928 mg) under ice-cooling, followed by stirring at room temperature for 3 hours. To the reaction mixture was added a 1 M aqueous sodium hydroxide solution, followed by extraction with chloroform. The organic layer was dried over anhydrous magnesium sulfate and the solvent was evaporated under reduced pressure to obtain the compound of Preparative Example 76 (629 mg) as a colorless oily substance.

Preparative Example 77

To a solution of the compound of Preparative Example 76 (625 mg) in 1,2-dichloroethane (100 ml) was added methanesulfonic acid (486 mg) under ice-cooling. After stirring at the same temperature for 6 hours, a 1 M aqueous sodium hydroxide solution was added thereto, followed by extraction with chloroform. The organic layer was dried over anhydrous magnesium sulfate, the solvent was then evaporated under reduced pressure, and the residue was purified by silica gel column chromatography (eluent; chloroform:methanol=10:1) to obtain the compound of Preparative Example 77 (100 mg) as a colorless amorphous.

Preparative Example 78

To a solution of a free from of the compound of Example 66 (668 mg) in tetrahydrofuran (15 ml) was added di-tert-butyl dicarbonate (645 mg), followed by stirring at room temperature for 3 hours. Water was added thereto, followed by extraction with ethyl acetate, washing with saturated brine, and then drying over anhydrous sodium sulfate, and the solvent was evaporated under reduced pressure. The residue was purified by silica gel chromatography (eluent; n-hexane:ethyl acetate=100:0-60:40) to obtain the compound of Preparative Example 78 (829 mg) as a colorless oily substance.

Preparative Example 79

To a solution of the compound of Preparative Example 78 (100 mg) in ethanol (3 ml) was added a 6 M aqueous sodium hydroxide solution, followed by heating under reflux for 5 hours. The reaction solution was concentrated under reduced pressure, and to the residue was added 1 M hydrochloric acid (30 ml), followed by extraction with ethyl acetate. The organic layer was washed with saturated brine and dried over anhydrous sodium sulfate, and the solvent was then evaporated under reduced pressure. The residue was dissolved in N,N-dimethyl formamide (5 ml), and methyl amine hydrochloride (103 mg), 1-hydroxybenzotriazole (83 mg), N-[3-(dimethylamino)propyl]-N'-ethylcarbodiimide hydrochloride (117 mg), and triethylamine (0.21 ml) were sequentially added, followed by stirring at room temperature overnight. The reaction mixture was added with a saturated aqueous sodium hydrogen carbonate solution, extracted with ethyl acetate, washed with saturated brine, and then dried over anhydrous sodium sulfate. The solvent was evaporated under reduced pressure and the residue was then purified by silica gel column chromatography (eluent; chloroform:methanol=100:0-90:10) to obtain the compound of Preparative Example 79 (104 mg) as a colorless oily substance.

Preparative Example 82

To a solution of the compound of Preparative Example 78 (113 mg) in toluene (1.5 ml) was slowly added a solution of 1 M diisobutylaluminum hydride in toluene (0.8 ml) at −70° C., followed by stirring at the same temperature for 2 hours. To the reaction solution was slowly added methanol, followed by stirring for 20 minutes, and the reaction solution was then poured into 1 M hydrochloric acid under ice-cooling. This was extracted with ethyl acetate, washed with saturated brine, and dried over anhydrous sodium sulfate, and the solvent was then evaporated under reduced pressure. Subsequently, the residue was dissolved in methanol, and sodium borohydride (14 mg) was added thereto under ice-cooling, followed by stirring for 30 minutes. A saturated aqueous ammonium chloride solution was added thereto, followed by extraction with ethyl acetate, washing with a saturated aqueous sodium hydrogen carbonate solution and saturated brine, and then drying over anhydrous sodium sulfate. The solvent was evaporated under reduced pressure and the residue was purified by silica gel column chromatography (eluent; chloroform:methanol=100:0-90:10) to obtain the compound of Preparative Example 82 (114 mg) as a colorless oily substance.

Preparative Example 83

To a solution of the compound of Preparative Example 82 (53 mg) in tetrahydrofuran (1 ml) were added 55% oily sodium hydride (8 mg) and methyl iodide (0.1 ml) under ice-cooling, followed by stirring at room temperature for 3 hours. A saturated aqueous ammonium chloride solution was added thereto, followed by extraction with ethyl acetate, washing with saturated brine, and then drying over anhydrous sodium sulfate, and the solvent was evaporated under reduced pressure. The residue was purified by silica gel column chromatography (eluent; n-hexane:ethyl acetate=100:0-80:20) to obtain the compound of Preparative Example 83 (40 mg) as a colorless oily substance.

Preparative Example 84

To a solution of a free from of the compound of Example 16 (1.17 g) in chloroform (20 ml) were added a saturated aqueous sodium hydrogen carbonate solution (20 ml) and benzyl chloroformate (0.8 ml), followed by stirring at room temperature for 17 hours. Chloroform and water were added thereto to carry out the liquid separation, and the organic layer was washed with saturated brine and then dried over anhydrous sodium sulfate. The solvent was evaporated under reduced pressure and the residue was purified by silica gel column chromatography (eluent; n-hexane:ethyl acetate=100:0-60:40) to obtain the compound of Preparative Example 84 (1.72 g) as a colorless solid.

Preparative Example 86

To a solution of the compound of Preparative Example 85 (250 mg) in N,N-dimethyl formamide (3 ml) was added 55% oily sodium hydride (39 mg) under ice-cooling, followed by stirring at the same temperature for 15 minutes. Methyl iodide (0.069 ml) was added thereto, followed by stirring at room temperature for 2 hours. A saturated aqueous ammonium chloride solution was added thereto, followed by extraction with chloroform and drying over anhydrous magnesium sulfate, and the solvent was then evaporated under reduced pressure. The residue was purified by silica gel column chromatography (eluent; n-hexane:ethyl acetate=3:1) to obtain the compound of Preparative Example 86 (219 mg) as a colorless oily substance.

Preparative Example 88

To a solution of the compound of Preparative Example 84 (1.14 g) in N-methyl pyrrolidone (20 ml) were added zinc cyanide (388 mg), calcium hydroxide (245 mg), and tetrakis (triphenylphosphine) palladium (0) (960 mg), followed by stirring at 100° C. for 3 hours. To the reaction solution were added chloroform and water, the insoluble materials were removed by filtration over Celite, and the liquid separation was carried out. The organic layer was washed with a 1 M aqueous sodium hydroxide solution and saturated brine, and dried over anhydrous sodium sulfate, and the solvent was then evaporated under reduced pressure. The residue was purified by silica gel column chromatography (eluent; n-hexane:ethyl acetate=60:40-30:70) to obtain the compound of Preparative Example 88 (988 mg) as a colorless oily substance.

Preparative Example 89

To a solution of the compound of Preparative Example 84 (283 mg) in toluene (5 ml) were sequentially added pyrrolidine (0.07 ml), sodium tert-butoxide (95 mg), tris(dibenzylideneacetone)dipalladium (0) (19 mg), and (2-biphenyl)dicyclohexylphosphine (29 mg), followed by stirring at 85° C. for 5 hours. To the reaction mixture were added ethyl acetate and water to carry out the liquid separation, the organic layer was washed with a saturated aqueous sodium chloride solution and dried over anhydrous sodium sulfate, and the solvent was evaporated under reduced pressure. The residue was purified by basic silica gel column chromatography (eluent; n-hexane:ethyl acetate=9:1) to obtain the compound of Preparative Example 89 (102 mg) as a colorless oily substance.

Preparative Example 90

To a mixture of methyl (4aRS,9bRS)-9b-methyl-2-oxo-1,2,3,4,5,9b-hexahydro-4-aH-indeno[1,2-b]pyridine-4a-carboxylate (770 mg) in toluene (10 ml) was added a solution of 70% sodium aluminum bis(2-methoxyethoxy)dihydride in toluene (4.2 ml), followed by stirring at 80° C. for 4 hours. To the reaction solution was added a 1 M aqueous sodium hydroxide solution under ice-cooling, followed by extraction with chloroform, the organic layer was dried over anhydrous magnesium sulfate, and the solvent was then evaporated under reduced pressure. The residue was dissolved in chloroform (10 ml), and benzyl chloroformate (1.5 g) and a saturated aqueous sodium hydrogen carbonate solution (10 ml) were added thereto, followed by stirring at room temperature for 1 hour. To the reaction solution was added saturated aqueous ammonia (4 ml), followed by extraction with chloroform, the organic layer was dried over anhydrous magnesium sulfate, and the solvent was then evaporated under reduced pressure. The residue was purified by silica gel column chromatography (eluent; n-hexane:ethyl acetate=1:1-0:1) to obtain the compound of Preparative Example 90 (361 mg) as a colorless oily substance.

Preparative Example 91

To a solution of the compound of Preparative Example 90 (180 mg) in N,N-dimethyl formamide (3 ml) was added 55% oily sodium hydride (45 mg) under ice-cooling, followed by stirring for 30 minutes under ice-cooling. Methyl iodide (0.06 ml) was added thereto, followed by stirring at the same temperature for further 1 hour, and a saturated aqueous ammonium chloride solution was then added thereto, followed by extraction with ethyl acetate. The organic layer was dried over anhydrous magnesium sulfate, the solvent was evaporated under reduced pressure and the residue was then purified by silica gel column chromatography (eluent; n-hexane:ethyl acetate=4:1) to obtain the compound of Preparative Example 91 (167 mg) as a colorless oily substance.

Preparative Example 93

To a solution of methyl (4aRS,9bRS)-2-oxo-1,2,3,4,5,9b-hexahydro-4aH-indeno[1,2-b]pyridine-4a-carboxylate (200 mg) in tetrahydrofuran (4 ml) was added a solution of 1 M methyl magnesium bromide in tetrahydrofuran (4 ml), followed by stirring at room temperature for 2 days. A saturated aqueous ammonium chloride solution was added thereto, followed by extraction with chloroform, the organic layer was dried over anhydrous magnesium sulfate, and the solvent was then evaporated under reduced pressure. The residue was purified by silica gel column chromatography (eluent; chloroform:methanol=10:1) to obtain the compound of Preparative Example 92 (102 mg) as a colorless amorphous.

Preparative Example 94

To a solution of methyl (4aRS,9bRS)-2-oxo-1,2,3,4,5,9b-hexahydro-4aH-indeno[1,2-b]pyridine-4a-carboxylate (2.0 g) in methanol (10 ml) was added a 5 M aqueous sodium hydroxide solution, followed by stirring at room temperature for 2 hours. Concentrated hydrochloric acid (12 ml) was added thereto under ice-cooling, and then followed by further stirring for 30 minutes, and the resulting precipitate was collected by filtration to obtain the compound of Preparative Example 94 (1.68 g) as an off-white powder.

Preparative Example 95

To a solution of the compound of Preparative Example 94 (400 mg) in N,N-dimethyl formamide (10 ml) were sequentially added N-[3-(dimethylamino)propyl]-N'-ethylcarbodiimide hydrochloride (497 mg), 1-hydroxybenzotriazole (233 mg), piperidine (295 mg), and triethylamine (350 mg). After stirring the reaction liquid at room temperature for 6 hours, a saturated aqueous sodium hydrogen carbonate solution was added thereto and the resulting precipitate was collected by filtration to obtain the compound of Preparative Example 95 (388 mg) as a colorless powder.

Preparative Example 99

To a solution of the compound of Preparative Example 38 (510 mg) and methyl iodide (0.24 ml) in N,N-dimethyl formamide (10 ml) was added 55% oily sodium hydride (133 mg), followed by stirring at room temperature for 1 hour. To the reaction solution was added a saturated aqueous ammonium chloride solution, followed by extraction with chloroform, the organic layer was dried over anhydrous magnesium sulfate, and the solvent was then evaporated under reduced pressure. The residue was purified by silica gel column chromatography (chloroform:methanol=30:1) to obtain the compound of Preparative Example 99 (536 mg) as a colorless viscous solid.

Preparative Example 100

To a solution of the compound of Preparative Example 40 (650 mg) and triethylamine (363 ml) in methanol (50 ml) was added 10% palladium-supported carbon having a water content of 50% (500 mg), followed by stirring at room temperature for 22 hours at normal pressure under a hydrogen atmosphere. The insoluble materials were removed by filtration through Celite, and the filtrate was subjected to liquid separation with water and ethyl acetate, and the organic layer was washed with saturated brine. After drying over anhydrous magnesium sulfate, the solvent was evaporated under reduced pressure to obtain the compound of Preparative Example 100 (395 mg) as a colorless solid.

Preparative Example 101

To a suspension of methyl 3-(2-methoxy phenyl)-3-oxopropanoate (5.08 g) and potassium carbonate (5.0 g) in tetrahydrofuran (50 ml) was added ethyl iodide (2.5 ml), followed by stirring at 80° C. for 13 hours. To the reaction mixture was added water, followed by extraction with ethyl acetate, and the organic layer was washed with saturated brine and then dried over anhydrous magnesium sulfate. The solvent was evaporated under reduced pressure and the residue was purified by silica gel column chromatography (eluent; n-hexane:ethyl acetate) to obtain the compound of Preparative Example 101 (4.51 g) as a pale yellow oily substance.

Preparative Example 102

To a mixed solution of the compound of Preparative Example 101 (4.51 g) in tetrahydrofuran (40 ml) and tert-butanol (20 ml) were added potassium tert-butoxide (500 mg) and acrylonitrile (1.8 ml) under ice-cooling, followed by stirring at the same temperature for 1 hour and further at room temperature for 5 hours. To the reaction solution was added a saturated aqueous ammonium chloride solution, followed by extraction with ethyl acetate, and the organic layer was washed with water and saturated brine, and then dried over anhydrous magnesium sulfate. The solvent was evaporated under reduced pressure and the residue was purified by silica gel column chromatography (eluent; n-hexane:ethyl acetate) to obtain the compound of Preparative Example 102 (4.37 g) as a colorless oily substance.

Preparative Example 103

A solution of the compound of Preparative Example 102 (4.36 g) in lithium chloride (2.0 g) in dimethylsulfoxide (40 ml) was stirred at 150° C. for 3 hours, and lithium chloride (2.0 g) was added thereto, followed by stirring at the same temperature for 3 hours. The reaction solution was cooled, 1 M hydrochloric acid was then added thereto, followed by stirring for a while and extraction with ethyl acetate, and the organic layer was washed with water and saturated brine. After drying over anhydrous magnesium sulfate, the solvent was then evaporated under reduced pressure, and the residue was purified by silica gel column chromatography (eluent; n-hexane:ethyl acetate) to obtain the compound of Preparative Example 103 (3.1 g) as a pale yellow oily substance.

Preparative Example 104

To a solution of the compound of Preparative Example 103 (3.1 g) in chloroform (50 ml) was added a solution of 1.0 M boron tribromide in dichloromethane (15 ml) under ice-cooling, followed by stirring at the same temperature for 1 hour. To the reaction solution were added water and a saturated aqueous ammonium chloride solution, followed by extraction with chloroform, and the organic layer was dried over anhydrous magnesium sulfate. The solvent was evaporated under reduced pressure and the residue was purified by silica gel column chromatography (eluent; n-hexane:ethyl acetate) to obtain the compound of Preparative Example 104 (1.52 g) as a pale yellow oily substance.

Preparative Example 105

To a solution of the compound of Preparative Example 104 (1.51 g) and pyridine (5 ml) in methylene chloride (30 ml) was added trifluoromethanesulfonic anhydride (0.15 ml) under ice-cooling, followed by stirring at the same temperature for 1 hour and further at room temperature for 19 hours. To the reaction solution were added water and 1 M hydrochloric acid under ice-cooling, followed by extraction with chloroform, and the organic layer was dried over anhydrous magnesium sulfate. The solvent was evaporated under reduced pressure and the residue was purified by silica gel column chromatography (eluent; n-hexane:ethyl acetate) to obtain the compound of Preparative Example 105 (2.37 g) as a colorless oily substance.

Preparative Example 106

To a solution of the compound of Preparative Example 105 (1.24 g) in N,N-dimethyl formamide (20 ml) was added 1,8-diazabicyclo[5.4.0]undecene (1.6 ml), followed by stirring at 80° C. for 2 hours. The reaction was cooled, and water and 1 M hydrochloric acid were then added thereto, followed by extraction with ethyl acetate, and the organic layer was washed with water and saturated brine. After drying over anhydrous magnesium sulfate, the solvent was evaporated under reduced pressure and the residue was purified by silica gel column chromatography (eluent; n-hexane:ethyl acetate) to obtain the compound of Preparative Example 106 (350 mg) as a pale yellow solid.

Preparative Example 107

To a solution of 4-bromobenzenethiol (5.0 g) and ethyl 2-bromopropionate (4.0 ml) in N,N-dimethyl formamide (50 ml) was added potassium carbonate (4.4 g), followed by heating and stirring at 60° C. for 4 hours. The reaction was cooled, water was then added thereto, followed by extraction with ethyl acetate, and the organic layer was washed with saturated brine. After drying over anhydrous magnesium sulfate, the solvent was evaporated under reduced pressure to obtain the compound of Preparative Example 107 (8.2 g) as a yellow oily substance.

Preparative Example 108

To a mixed solution of the compound of Preparative Example 107 (5.15 g) in ethanol (25 ml)-tetrahydrofuran (25 ml) was added a 1 M aqueous sodium hydroxide solution (70 ml), followed by stirring at room temperature for 3 days. To the reaction solution was added 1 M hydrochloric acid (100 ml), followed by extraction with ethyl acetate, and the organic layer was washed with saturated brine. After drying over anhydrous magnesium sulfate, the solvent was evaporated under reduced pressure to obtain the compound of Preparative Example 108 (4.24 g) as a colorless solid.

Preparative Example 109

To the compound of Preparative Example 108 (2.17 g) was added trifluoromethanesulfonic acid (50 g), followed by stirring at 80° C. for 30 minutes. The reaction was cooled and then poured into ice water, followed by extraction with chloroform. The organic layer was washed with a saturated aqueous sodium hydrogen carbonate solution and then dried over anhydrous magnesium sulfate. The solvent was evaporated under reduced pressure and the residue was purified by silica gel column chromatography (eluent; chloroform:methanol) to obtain the compound of Preparative Example 109 (715 mg) as a red-brown oily substance.

Example 1

To a solution of the compound of Preparative Example 39 (879 mg) in tetrahydrofuran (15 ml) was added lithium aluminum hydride (400 mg), followed by heating and stirring at 60° C. for 3 hours. After completion of the reaction, the solution was ice-cooled, and water (0.4 ml), a 15% aqueous sodium hydroxide solution (0.4 ml), and water (1.2 ml) were sequentially added thereto. The mixture was stirred at room temperature for 1 hour. Anhydrous magnesium sulfate was added thereto, followed by stirring and then filtering through Celite. The filtrate was concentrated under reduced pressure to obtain (4aRS,9bRS)-4a-ethyl-2,3,4,4a,5,9b-hexahydro-1H-indeno[1,2-b]pyridine (817 mg) as a colorless oily substance. This was made into a hydrochloride by a conventional method, washed with ethyl acetate, and collected by filtration to obtain (4aRS,9bRS)-4a-ethyl-2,3,4,4a,5,9b-hexahydro-1H-indeno[1,2-b]pyridine hydrochloride as a colorless powder.

Example 13

To a solution of the compound of Preparative Example 100 (472 mg) in tetrahydrofuran (10 ml) was added a solution of a 1.02 M borane tetrahydrofuran complex in tetrahydrofuran (6.6 ml), followed by stirring at 80° C. for 2 hours and then cooling to room temperature. To the reaction mixture was added piperidine (2.0 ml), followed by stirring at 60° C. for 2 hours. Then, water was added thereto, followed by extraction with ethyl acetate, and washing with a saturated aqueous sodium hydrogen carbonate solution, water, and saturated brine. After drying over anhydrous sodium sulfate, the solvent was evaporated under reduced pressure to obtain (4aRS,9bRS)-4a-methyl-1,2,3,4,4a,9b-hexahydro[1]benzothieno[3,2-b]pyridine (396 mg) as an oily substance. This was made into a hydrochloride by a conventional method, washed with ethyl acetate, and then collected by filtration to obtain (4aRS,9bRS)-4a-methyl-1,2,3,4,4a,9b-hexahydro[1]benzothieno[3,2-b]pyridine hydrochloride as a colorless powder.

Example 22

To a mixture of the compound of Preparative Example 38 (42.5 g) in toluene (600 ml) was slowly added dropwise a solution of a 70% sodium aluminum bis(2-methoxyethoxy) dihydride in toluene (182 g) under ice-cooling. After completion of the dropwise addition, the mixture was heated and stirred at 60° C. for 4 hours. After completion of the reaction, a 1 M aqueous sodium hydroxide solution was slowly added dropwise under ice-cooling. The mixture was extracted with chloroform, the organic layer was dried over anhydrous magnesium sulfate, and the solvent was then evaporated under reduced pressure. The residue was dissolved in ethyl acetate, followed by extraction twice with 2 M hydrochloric acid (150 ml). The aqueous layer was basified by sodium hydroxide, followed by extraction with toluene and drying over anhydrous magnesium sulfate, and the solvent was evaporated under reduced pressure to obtain (4aRS,9bRS)-4a-methyl-2,3,4,4a,5,9b-hexahydro-1H-indeno[1,2-b]pyridine (34 g) as an oily substance. This was made into a hydrochloride by a conventional method, washed with ethyl acetate, and collected by filtration to obtain (4aRS,9bRS)-4a-methyl-2,3,4,4a,5,9b-hexahydro-1H-indeno[1,2-b]pyridine hydrochloride as a colorless powder.

Example 26-1 and Example 26-2

The compound of Preparative Example 95 (388 mg) was suspended in tetrahydrofuran (5 ml), and a solution of a 1 M borane tetrahydrofuran complex in tetrahydrofuran (2 ml) was added thereto. After stirring at 60° C. for 5 hours, a solution of 10% hydrogen chloride in methanol was added thereto under ice-cooling, followed by stirring at 60° C. for further 1 hour. A 1 M aqueous sodium hydroxide solution was added thereto under ice-cooling, followed by extraction with chloroform. After drying over anhydrous magnesium sulfate, the solvent was evaporated under reduced pressure, and the residue was purified by basic silica gel column chromatography (eluent; n-hexane:ethyl acetate=10:1-4:1) to obtain (4aRS,9bSR)-4a-(piperidin-1-ylmethyl)-2,3,4,4a,5,9b-hexahydro-1H-indeno[1,2-b]pyridine (66 mg) and (4aRS,9bRS)-4a-(piperidin-1-ylcarbonyl)-2,3,4,4a,5,9b-hexahydro-1H-indeno[1,2-b]pyridine (182 mg), respectively. These were each made into a hydrochloride by a conventional method, washed with 2-propanol/ethyl acetate, and collected by filtration to obtain (4aRS,9bSR)-4a-(piperidin-1-ylmethyl)-2,3,4,4a,5,9b-hexahydro-1H-indeno[1,2-b]pyridine hydrochloride [Example 26-1] and (4aRS,9bRS)-4a-(piperidin-1-ylcarbonyl)-2,3,4,4a,5,9b-hexahydro-1H-indeno[1,2-b]pyridine hydrochloride [Example 26-2], respectively, as a colorless powder.

Example 30

To a solution of the compound of Preparative Example 63-2 (135 mg) in tetrahydrofuran (5 ml) was added lithium aluminum hydride (100 mg) under ice-cooling, followed by stirring at room temperature for 6 hours. To the reaction solution were sequentially added water (0.1 ml), a 15% aqueous sodium hydroxide solution (0.1 ml), and water (0.3 ml), and the mixture was stirred at room temperature for 3 days. Anhydrous magnesium sulfate was added thereto, followed by filtration through Celite, and the filtrate was concentrated under reduced pressure. The residue was purified by silica gel column chromatography (eluent; chloroform:methanol:saturated aqueous ammonia=20:1:0.1) to obtain a colorless oily substance (34 mg). This was made into a hydrochloride by a conventional method, washed with ethyl acetate, and collected by filtration to obtain (3aRS,8bSR)-3a-phenyl-1,2,3,3a,4,8b-hexahydroindeno[1,2-b]pyrrole hydrochloride (30 mg) as a colorless powder.

Example 31

To a mixed suspension of Raney nickel that had been sufficiently washed with water in water (20 ml)/methanol (45 ml) was added a solution of the compound of Preparative Example 2 (1.77 g) in methanol (45 ml), followed by stirring at room temperature overnight at normal pressure under a hydrogen atmosphere. The reaction suspension was filtered through Celite, the filtrate was concentrated under reduced pressure, and the residue was purified by silica gel column chromatography (eluent; chloroform:methanol:saturated aqueous ammonia=10:1:0.1) to obtain an oily substance (415 mg). This was dissolved in 1,2-dichloroethane (40 ml), and sodium triacetoxyborohydride (848 mg) was added thereto, followed by stirring at room temperature for 2 days. To the reaction mixture was added a 1 M aqueous sodium hydroxide solution, followed by extraction with chloroform and drying over anhydrous magnesium sulfate, and the solvent was then evaporated under reduced pressure. The residue was purified by silica gel column chromatography (eluent; chloroform:methanol:saturated aqueous ammonia=20:1:0.1-10:1:0.1) to obtain (4aRS,9bSR)-4a-ethyl-2,3,4,4a,5,9b-hexahydro-1H-indeno[1,2-b]pyridine (183 mg) as an oily substance. This was made into a hydrochloride by a conventional method, washed with ethyl acetate, and collected by filtration to obtain (4aRS,9bSR)-4a-ethyl-2,3,4,4a,5,9b-hexahydro-1H-indeno[1,2-b]pyridine hydrochloride as a colorless powder.

Example 34-1 and Example 34-2

To a solution of the compound of Preparative Example 59 (240 mg) in 1,2-dichloroethane (4 ml) was added tri-n-butyl phosphine (190 mg), followed by stirring at room temperature for 1 hour. Acetic acid (0.27 ml) and sodium triacetoxyborohydride (299 mg) were added thereto, followed by stirring at 50° C. for 3 hours. A saturated aqueous sodium hydrogen carbonate solution was added thereto, followed by extraction with chloroform, drying over anhydrous magnesium sulfate, and then concentrating under reduced pressure. The residue was purified by basic silica gel column chromatography (eluent; n-hexane:ethyl acetate=4:1-2:1) to obtain (3aRS,7aSR,11bRS)-2,3,4,5,6,7,7a,11b-octahydro-1H-fluoreno[9,8a-b]pyrrole (24 mg), and (3aRS,7aSR,11bRS)-1-ethyl-2,3,4,5,6,7,7a,11b-octahydro-1H-fluoreno[9,8a-b]pyrrole (52 mg). These were each made into a hydrochloride by a conventional method, washed with ethyl acetate, and collected by filtration to obtain (3aRS,7aSR,11bRS)-2,3,4,5,6,7,7a,11b-octahydro-1H-fluoreno[9,8a-b]pyrrole hydrochloride (8 mg) [Example 34-1] and (3aRS,7aSR,11bRS)-1-ethyl-2,3,4,5,6,7,7a,11b-octahydro-1H-fluoreno[9,8a-b]pyrrole hydrochloride (39 mg) [Example 34-2], respectively, as a colorless powder.

Example 36

To a solution of the compound of Preparative Example 60 (475 mg) in diethyl ether (5 ml) was added tri-n-butyl phosphine (0.545 ml) at room temperature, followed by stirring at the same temperature for 1 hour. A solution of a boron trifluoride diethyl ether complex (0.559 ml) and 1 M methyl lithium in diethyl ether (6.62 ml) were added thereto under ice-cooling, followed by stirring at the same temperature for 3 hours. To the reaction solution was added a saturated aqueous sodium hydrogen carbonate solution, followed by extraction with chloroform and drying over anhydrous magnesium sulfate, and the solvent was then evaporated under reduced pressure. The residue was purified by silica gel column chromatography (eluent; n-hexane:ethyl acetate=4:1-2:1) to obtain (3aRS,8bSR)-3a,8b-dimethyl-1,2,3,3a,4,8b-hexahydroindeno[1,2-b]pyrrole as a colorless oily substance. This was made into a hydrochloride by a conventional method, washed with n-hexane/ethyl acetate, and then collected by filtration to obtain (3aRS,8bSR)-3a,8b-dimethyl-1,2,3,3a,4,8b-hexahydroindeno[1,2-b]pyrrole hydrochloride (80 mg) as a colorless powder.

Example 37

A Raney nickel suspension (2 ml) was sufficiently washed with water, and a solution of the compound of Preparative Example 1 (1.99 g) in methanol (50 ml) was added thereto. The mixture was stirred at room temperature for 2 days under a hydrogen atmosphere and filtered through Celite, and the filtrate was concentrated under reduced pressure. The residue was dissolved in diethyl ether (50 ml), and a boron trifluoride diethyl ether complex (1.85 g) was added thereto under ice-cooling. A solution of 1 M methyl lithium in diethyl ether (30 ml) was further added at the same temperature, followed by stirring at room temperature for 3 hours. A 1 M aqueous sodium hydroxide solution was added thereto, followed by extraction with chloroform and drying over anhydrous magnesium sulfate, and the solvent was evaporated under reduced pressure. The residue was purified by silica gel column chromatography (eluent; chloroform:methanol:saturated aqueous ammonia=20:1:0.1) and then by basic silica gel column chromatography (eluent; n-hexane:ethyl acetate=10:1-2:1) to obtain (4aRS,9bSR)-4a,9b-dimethyl-2,3,4,4a,5,9b-hexahydro-1H-indeno[1,2-b]pyridine (746 mg) as a colorless oily substance. This was made into a hydrochloride by a conventional method, washed with ethyl acetate, and collected by filtration to obtain (4aRS,9bSR)-4a,9b-dimethyl-2,3,4,4a,5,9b-hexahydro-1H-indeno[1,2-b]pyridine hydrochloride as a colorless powder.

Example 38-1 and Example 38-2

The compound of Preparative Example 65 (404 mg) was dissolved in 1,2-dichloroethane (20 ml), and titaniumtetraisopropoxide (528 mg) was added thereto, followed by stirring at 60° C. for 3 hours. After cooling to room temperature, sodium triacetoxyborohydride (788 mg) was added thereto, followed by stirring at room temperature overnight. A 1 M aqueous sodium hydroxide solution was added thereto, followed by filtration through Celite, and the filtrate was extracted with chloroform, dried over anhydrous magnesium sulfate, and then concentrated under reduced pressure. The residue was purified by silica gel column chromatography (eluent; chloroform:methanol:saturated aqueous ammonia=10:1:0.1) to obtain (5aRS,10bRS)-5a-methyl-1,2,3,4,5,5a,6,10b-octahydroindeno[1,2-b]azepine (27 mg) and (5aRS,10bSR)-5a-methyl-1,2,3,4,5,5a,6,10b-octahydroindeno[1,2-b]azepine (185 mg). These were each made into a hydrochloride by a conventional method, washed with ethyl acetate, and collected by filtration to obtain (5aRS,10bRS)-5a-methyl-1,2,3,4,5,5a,6,10b-octahydroindeno[1,2-b]azepine hydrochloride [Example 38-1] and (5aRS,10bSR)-5a-methyl-1,2,3,4,5,5a,6,10b-octahydroindeno[1,2-b]azepine hydrochloride [Example 38-2], respectively, as a colorless powder.

Example 39

The compound of Preparative Example 71 (552 mg) was dissolved in acetic acid (10 ml), and concentrated hydrochloric acid (2.5 ml) was added thereto, followed by heating under reflux. The reaction mixture was neutralized by adding an excessive amount of a saturated aqueous sodium hydrogen carbonate solution, extracted with ethyl acetate. After washing with saturated brine and drying over anhydrous sodium sulfate, the solvent was evaporated under reduced pressure. The residue was dissolved in methanol, and sodium borohydride was added thereto under ice-cooling, followed by stirring at the same temperature for 30 minutes. A saturated aqueous ammonium chloride solution was added thereto to stop the reaction, and then a saturated aqueous sodium hydrogen carbonate solution was added thereto, followed by extraction with ethyl acetate. After drying over anhydrous sodium sulfate, the solvent was evaporated under reduced pressure, and the residue was purified by basic silica gel column chromatography (eluent; n-hexane:ethyl acetate=10:1-2:1) to obtain (4aRS,9bSR)-4a-methyl-2,3,4,4a,5,9b-hexahydro-1H-indene[1,2-b]pyridine (164 mg) as an oily substance. This was made into a hydrochloride by a conventional method, washed with ethyl acetate, and collected by filtration to obtain (4aRS,9bSR)-4a-methyl-2,3,4,4a,5,9b-hexahydro-1H-indene[1,2-b]pyridine hydrochloride as a colorless powder.

Example 40-1 and Example 40-2

To a solution of the compound of Preparative Example 57 (1.27 g) in methylene chloride (20 ml) was added a solution of 1 M boron tribromide in methylene chloride (12.4 ml) under ice-cooling, followed by stirring at room temperature for 3 hours. To the reaction solution was added water, followed by extraction with ethyl acetate, the organic layer was washed with saturated brine and then dried over anhydrous magnesium sulfate, and the solvent was evaporated under reduced pressure. The residue was dissolved in N,N-dimethyl formamide (20 ml), and sodium azide (809 mg) was added thereto at room temperature, followed by stirring for 3 days. To the reaction solution was added water, followed by extraction with ethyl acetate, the organic layer was washed with water and saturated brine, and then dried over anhydrous magnesium sulfate, and the solvent was evaporated under reduced pressure. Further, the residue was dissolved in methanol (20 ml), and tri-n-butyl phosphine (2.3 ml) was added thereto, followed by stirring overnight. The reaction solution was concentrated under reduced pressure, and the residue was dissolved in ethyl acetate and extracted twice with 1 M hydrochloric acid (20 ml). The aqueous layer was basified by the adding a 1 M aqueous sodium hydroxide solution, extracted with chloroform, and dried over anhydrous magnesium sulfate, and the solvent was evaporated under reduced pressure. Thereafter, the residue was dissolved in 1,2-dichloroethane (20 ml), acetic acid (1.78 ml) was added thereto, followed by stirring at room temperature for 30 minutes, and then sodium triacetoxyborohydride (2.64 g) was added thereto, followed by stirring at room temperature overnight. The reaction solution was concentrated under reduced pressure, and the residue was dissolved in ethyl acetate and extracted twice with 1 M hydrochloric acid (20 ml). The aqueous layer was basified by adding a 1 M aqueous sodium hydroxide solution, extracted with chloroform, and dried over anhydrous magnesium sulfate, and the solvent was evaporated under reduced pressure. The residue was purified by basic silica gel column chromatography (eluent; n-hexane:ethyl acetate=2:1-1:1) to obtain (3aRS,8bSR)-3a-methyl-1,2,3,3a,4,8b-hexahydroindeno[1, 2-b]pyrrole (172 mg) as a colorless oily substance and further a mixture of aminoketone products (242 mg) as an oily substance. Further, the aminoketone mixture was dissolved in 1,2-dichloroethane (10 ml), acetic acid (0.36 ml) was added thereto, followed by heating and stirring at 80° C. for 30 minutes, and sodium triacetoxyborohydride (2.64 g) was added thereto, followed by heating and stirring at the same temperature for 2 hours. The reaction solution was concentrated under reduced pressure, and the residue was dissolved in ethyl acetate and extracted twice with 1 M hydrochloric acid (20 ml). The aqueous layer was basified by adding a 1 M aqueous sodium hydroxide solution, extracted with chloroform, and dried over anhydrous magnesium sulfate, and the solvent was evaporated under reduced pressure. The residue was purified by basic silica gel column chromatography (eluent; n-hexane:ethyl acetate=2:1-1:1) to obtain (3aRS,8bSR)-1-ethyl-3a-methyl-1,2,3,3a,4,8b-hexahydroindeno[1,2-b]pyrrole (99 mg) as a colorless oily substance. The obtained product was each made into a hydrochloride by a conventional method, washed with ethyl acetate, and collected by filtration to obtain (3aRS,8bSR)-3a-methyl-1,2,3,3a,4,8b-hexahydroindeno[1,2-b]pyrrole hydrochloride [Example 40-2] and (3aRS,8bSR)-1-ethyl-3a-methyl-1,2,3,3a,4,8b-hexahydroindeno[1,2-b]pyrrole hydrochloride [Example 40-1], respectively, as a colorless powder.

Example 41

To a solution of the compound of Preparative Example 99 (229 mg) in tetrahydrofuran (2 ml) was added titanium tetrachloride (201 mg) at −20° C., followed by stirring at the same temperature for 30 minutes, and a solution of 1.4 M methyl magnesium bromide in tetrahydrofuran/toluene was added dropwise thereto. The reaction liquid was slowly warmed to room temperature over 2 hours, and then heated and stirred at 60° C. overnight. To the reaction mixture was added a 30% aqueous sodium hydroxide solution, the mixture was then filtered through Celite, and the filtrate was extracted with methylene chloride. The organic layer was dried over anhydrous magnesium sulfate, the solvent was then evaporated under reduced pressure, and the residue was purified by silica gel column chromatography (eluent; chloroform:methanol: saturated aqueous ammonia=10:1:0.1) to obtain (4aRS, 9bRS)-1,2,2,4a-tetramethyl-2,3,4,4a,5,9b-hexahydro-1H-indeno[1,2-b]pyridine (19 mg) as an oily substance. This was made into a salt using an equivalent amount of methanesulfonic acid by a conventional method, washed with ethyl acetate, and collected by filtration to obtain (4aRS,9bRS)-1, 2,2,4a-tetramethyl-2,3,4,4a,5,9b-hexahydro-1H-indeno[1,2-b]pyridine methanesulfonate (15 mg) as an off-white powder.

Example 42

To a solution of (4aRS,9bRS)-4a-methyl-2,3,4,4a,5,9b-hexahydro-1H-indeno[1,2-b]pyridine (140 mg) in tetrahydrofuran (3 ml) were added a 35% formalin solution (0.55 ml) and formic acid (0.3 ml), and the mixture was stirred at 80° C. for 1 hour. An excessive amount of a saturated aqueous sodium hydrogen carbonate solution was added thereto for neutralization, followed by extraction with chloroform, the organic layer was dried over anhydrous magnesium sulfate, and the solvent was evaporated under reduced pressure to obtain an oily substance (150 mg). This was made into a methanesulfonate using an equivalent amount of methanesulfonic acid by a conventional method, washed with ethyl acetate, and collected by filtration to obtain (4aRS,9bRS)-1, 4a-dimethyl-2,3,4,4a,5,9b-hexahydro-1H-indeno[1,2-b]pyridine methanesulfonate (193 mg) as a colorless powder.

Example 59

To a solution of (4aRS,9bRS)-4a-methyl-2,3,4,4a,5,9b-hexahydro-1H-indeno[1,2-b]pyridine (140 mg) and acetone (217 mg) in 1,2-dichloroethane was added sodium triacetoxyborohydride (792 mg), followed by stirring at room temperature for 3 days. A 1 M aqueous sodium hydroxide solution was added thereto, followed by extraction with chloroform, the organic layer was dried over anhydrous magnesium sulfate, and the solvent was then evaporated under reduced pressure to obtain (4aRS,9bRS)-1-isopropyl-4a-methyl-2,3,4,4a,5,9b-hexahydro-1H-indeno[1,2-b]pyridine (138 mg) as an oily substance. This was made into a salt using an equivalent amount of methanesulfonic acid by a conventional method, washed with ethyl acetate, and collected by filtration to obtain (4aRS,9bRS)-1-isopropyl-4a-methyl-2,3, 4,4a,5,9b-hexahydro-1H-indeno[1,2-b]pyridine methanesulfonate (95 mg) as a colorless powder.

Example 62

To a solution of (4aRS,9bRS)-4a-methyl-2,3,4,4a,5,9b-hexahydro-1H-indeno[1,2-b]pyridine (140 mg) in 1,2-dichloroethane (3 ml) were added acetic acid (0.214 ml) and sodium triacetoxyborohydride (1.1 g), followed by heating and stirring at 70° C. for 3 hours. The reaction solution was basified by adding a 1 M aqueous sodium hydroxide solution, extracted with chloroform, and dried over anhydrous magnesium sulfate, and the solvent was evaporated under reduced pressure to obtain (4aRS,9bRS)-1-ethyl-4a-methyl-2,3,4,4a,5,9b-hexahydro-1H-indeno[1,2-b]pyridine (105 mg) as an oily substance. This was made into a hydrochloride by a conventional method, washed with ethyl acetate, and collected by filtration to obtain (4aRS,9bRS)-1-ethyl-4a-methyl-2,3,4,4a,5,9b-hexahydro-1H-indeno[1,2-b]pyridine hydrochloride (108 mg) as a colorless powder.

Example 63

To a solution of the compound of Preparative Example 70-1 (1.97 g) in methanol (30 ml) was added 10% palladium-supported carbon (300 mg), followed by stirring at room temperature for 4 hours at normal pressure under a hydrogen atmosphere. After filtration through Celite, the filtrate was concentrated to obtain (4aRS,9bRS)-4a,9b-dimethyl-2,3,4,4a,5,9b-hexahydro-1H-indeno[1,2-b]pyridine (1.17 g) as an oily substance. This was made into a hydrochloride by a conventional method, washed with ethyl acetate, and collected by filtration to obtain (4aRS,9bRS)-4a,9b-dimethyl-2,3,4,4a,5,9b-hexahydro-1H-indeno[1,2-b]pyridine hydrochloride as a colorless powder.

Example 73

To a solution of the compound of Preparative Example 83 (40 mg) in ethyl acetate (3 ml) was added a solution of 4 M hydrogen chloride in ethyl acetate (1 ml), followed by stirring for 3 days. The reaction solution was extracted with water, basified by adding carbonate, and extracted with ethyl acetate. After washing with saturated brine and drying over anhydrous sodium sulfate, the solvent was evaporated under reduced pressure to obtain (4aRS,9bRS)-4a-ethyl-8-(methoxymethyl)-2,3,4,4a,5,9b-hexahydro-1H-indeno[1,2-b]pyridine (23 mg) as an oily substance. This was made into fumarate using an equivalent amount of fumaric acid by a conventional method, washed with acetonitrile, and collected by filtration to obtain (4aRS,9bRS)-4a-ethyl-8-(methoxymethyl)-2,3,4,4a,5,9b-hexahydro-1H-indeno[1,2-b]pyridine hydrochloride as a colorless powder.

Example 78-1 and Example 78-2

(4aRS,9bRS)-4a-Methyl-2,3,4,4a,5,9b-hexahydro-1H-indeno[1,2-b]pyridine was made into a salt using an equivalent amount of (+)-dibenzoyl-D-tartaric acid monohydrate, crystallization from acetone was repeated three times to carry out the optical resolution, and then the product was made into a free from by a conventional method to obtain (−)-(4aR,9bR)-4a-methyl-2,3,4,4a,5,9b-hexahydro-1H-indeno[1,2-b]pyridine [Example 78-1] as a colorless oily substance. (93% e.e.)

Similarly, the optical resolution was carried out using (−)-dibenzoyl-L-tartaric acid monohydrate to obtain an enantiomer of the compound of Example 78-1, (+)-(4aS,9bS)-4a-methyl-2,3,4,4a,5,9b-hexahydro-1H-indeno[1,2-b]pyridine [Example 78-2]. (97% e.e.)

The optical purity was measured by HPLC under the following condition.

[column: CHIRALCEL OD-RH (4.6×150 mm), eluent: acetonitrile/0.1 M aqueous $KPF_6$ solution=35/65, flow rate: 0.5 ml/min., UV wavelength: 210 nm, retention time: 7.6 min. ((+) form), 8.7 min. ((−) form)]

Example 79-1 and Example 79-2

(4aRS,9bRS)-4a-Ethyl-2,3,4,4a,5,9b-hexahydro-1H-indeno[1,2-b]pyridine was made into a salt using an equivalent amount of (+)-dibenzoyl-D-tartaric acid monohydrate, recrystallization from ethyl acetate was repeated three times to carry out the optical resolution, and then the product was made into a free from by a conventional method to obtain (−)-(4aR*,9bR*)-4a-ethyl-2,3,4,4a,5,9b-hexahydro-1H-indeno[1,2-b]pyridine [Example 79-1] as a colorless oily substance. (96% e.e.)

Similarly, the optical resolution was carried out using (−)-dibenzoyl-L-tartaric acid monohydrate to obtain an enantiomer of the compound of Example 79-1, (+)-(4aR*,9bR*)-4a-ethyl-2,3,4,4a,5,9b-hexahydro-1H-indeno[1,2-b]pyridine [Example 79-2]. (97% e.e.)

The optical purity was measured by HPLC under the following condition.

[column: CHIRALCEL OD-RH (4.6×150 mm), eluent: acetonitrile/0.1 M aqueous $KPF_6$ solution=35/65, flow rate: 0.5 ml/min., UV wavelength: 210 nm, retention time: 9.46 min. ((+) form), 12.29 min. ((−) form)]

Example 80-1 and Example 80-2

(4aRS,9bRS)-4a,9b-dimethyl-2,3,4,4a,5,9b-hexahydro-1H-indeno[1,2-b]pyridine was made into a salt using an equivalent amount of (−)-di-p-toluoyl-L-tartaric acid, recrystallization from ethyl acetate and then from methanol was conducted to carry out the optical resolution, and then the product was made into a free from by a conventional method to obtain (−)-(4aR*,9bR*)-4a,9b-dimethyl-2,3,4,4a,5,9b-hexahydro-1H-indeno[1,2-b]pyridine [Example 80-1] as a colorless oily substance (98% ee).

Similarly, the optical resolution was carried out using (+)-di-p-toluoyl-D-tartaric acid to obtain an enantiomer of the compound of Example 80-1, (+)-(4aR*,9bR*)-4a,9b-dimethyl-2,3,4,4a,5,9b-hexahydro-1H-indeno[1,2-b]pyridine [Example 80-2] (98% ee).

The optical purity was measured by HPLC under the following condition.

[column: CHIRALCEL OD-RH (4.6×150 mm), eluent: acetonitrile/0.1 M aqueous $KPF_6$ solution=35/65, flow rate: 0.5 ml/min., UV wavelength: 210 nm, retention time: 7.92 min. ((+) form), 9.72 min. ((−) form)]

Example 81

(−)-(4aR,9bR)-4a-Methyl-2,3,4,4a,5,9b-hexahydro-1H-indeno[1,2-b]pyridine was made into a hydrochloride by a conventional method, and then recrystallized from ethyl acetate/ethanol to obtain (4aR,9bR)-4a-methyl-2,3,4,4a,5,9b-hexahydro-1H-indeno[1,2-b]pyridine hydrochloride as a colorless crystal.

Example 82

(+)-(4aS,9bS)-4-a-Methyl-2,3,4,4a,5,9b-hexahydro-1H-indeno[1,2-b]pyridine was made into a hydrochloride by a conventional method and then recrystallized from ethyl acetate/ethanol to obtain (4aS,9bS)-4-a-methyl-2,3,4,4a,5,9b-hexahydro-1H-indeno[1,2-b]pyridine hydrochloride as a colorless crystal.

Example 83-1 and Example 83-2

(−)-(4aR*,9bR*)-4a-Ethyl-2,3,4,4a,5,9b-hexahydro-1H-indeno[1,2-b]pyridine and (+)-(4aR*,9bR*)-4a-ethyl-2,3,4,4a,5,9b-hexahydro-1H-indeno[1,2-b]pyridine were each made into a hydrochloride by a conventional method, washed with ethyl acetate, and then collected by filtration to obtain (4aR*,9bR*)-4a-ethyl-2,3,4,4a,5,9b-hexahydro-1H-indeno[1,2-b]pyridine hydrochloride and an enantiomer thereof, respectively, as a colorless powder.

Example 84-1 and Example 84-2

(−)-(4aR*,9bR*)-4a,9b-Dimethyl-2,3,4,4a,5,9b-hexahydro-1H-indeno[1,2-b]pyridine and (+)-(4aR*,9bR*)-4a,9b-dimethyl-2,3,4,4a,5,9b-hexahydro-1H-indeno[1,2-b]pyridine were each made into a hydrochloride by a conventional method, washed with ethyl acetate, and then collected by filtration to obtain (4aR*,9bR*)-4a,9b-dimethyl-2,3,4,4a,5,9b-hexahydro-1H-indeno[1,2-b]pyridine hydrochloride and an enantiomer thereof, respectively, as a colorless powder.

The chemical structural formulae of the Preparative Example compounds are shown in Table 4 to Table 12 below. Further, the chemical structural formulae of the Example compounds are shown in Table 13 to Table 25 below.

Further, the production processes and the physical data of the Preparative Example compounds are shown in Table 26 to Table 29 below. Further, the production processes and the physical data of the Example compounds are shown in Table 30 to Table 38 below.

TABLE 4-continued
| Px | STRUCTURE |
|---|---|
| 15 | 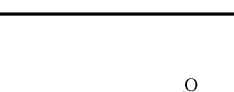 |
| 16 | 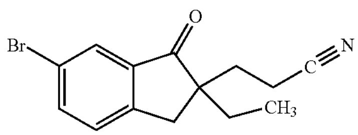 |
TABLE 5
| Px | STRUCTURE |
|---|---|
| 17 | 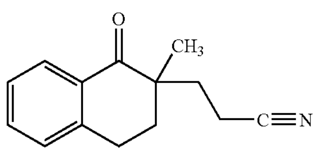 |
| 18 | 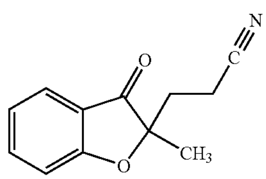 |
| 19 | 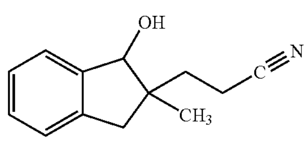 |
| 20 | 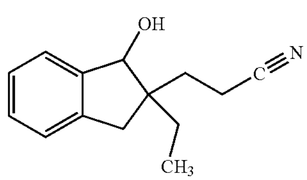 |
| 21 | 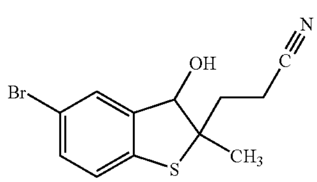 |
| 22 | 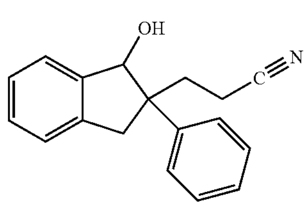 |
TABLE 5-continued
| Px | STRUCTURE |
|---|---|
| 23 | 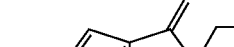 |
| 24 | 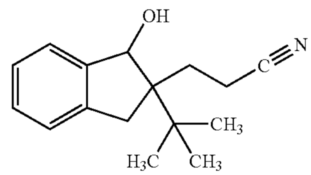 |
| 25 | 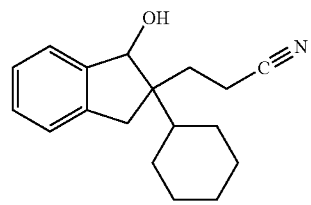 |
| 26 | 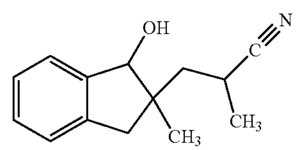 |
| 27 | 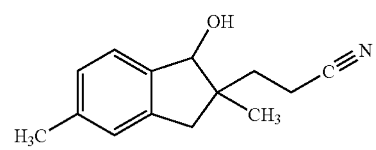 |
| 28 | 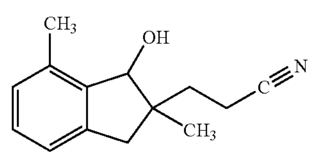 |
| 29 | 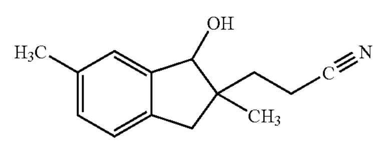 |
| 30 | 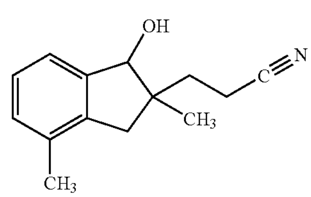 |
| 31 | 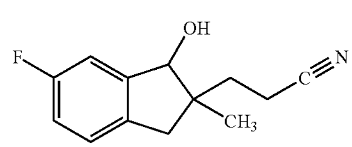 |

TABLE 5-continued

| Px | STRUCTURE |
|---|---|
| 32 | (6-methoxy-1-hydroxy-2-methyl-2,3-dihydro-1H-inden-2-yl)propanenitrile structure |

TABLE 6

| Px | STRUCTURE |
|---|---|
| 33 | 2-methyl-thieno-cyclopentane with OH and propanenitrile |
| 34 | 6-bromo-1-hydroxy-2-ethyl-indane with propanenitrile |
| 35 | 1-hydroxy-2-methyl-tetrahydronaphthalene with propanenitrile |
| 36 | 3-hydroxy-2-ethyl-benzofuran with propanenitrile |
| 37 | 3-hydroxy-2-methyl-benzofuran with propanenitrile |
| 38 | methyl-substituted indeno-piperidinone |
| 39 | ethyl-substituted indeno-piperidinone |

TABLE 6-continued

| Px | STRUCTURE |
|---|---|
| 40 | bromo thieno-fused piperidinone with methyl |
| 41 | phenyl-substituted indeno-piperidinone |
| 42 | isopropyl-substituted indeno-piperidinone |
| 43 | cyclohexyl-substituted indeno-piperidinone |
| 44 | tert-butyl-substituted indeno-piperidinone |
| 45 | dimethyl-substituted indeno-piperidinone |
| 46 | methyl-substituted indeno-piperidinone |

TABLE 7

| Px | STRUCTURE |
|---|---|
| 47 | 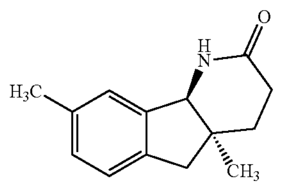 |
| 48 | 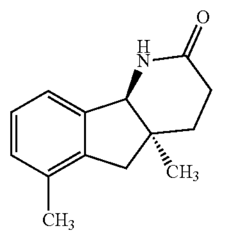 |
| 49 | 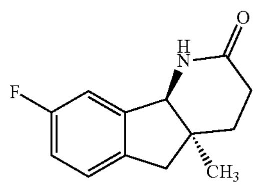 |
| 50 | 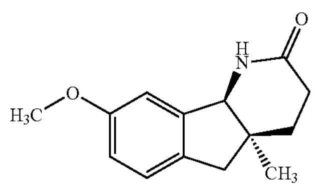 |
| 51-1 | 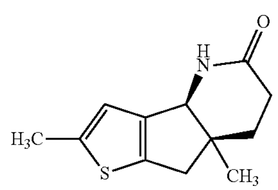 |
| 51-2 | 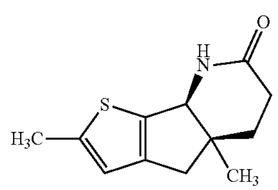 |
| 52 | 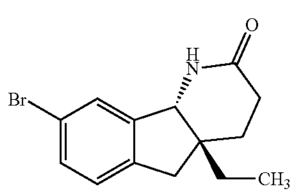 |
| 53 | 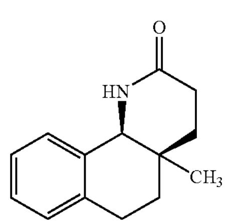 |

TABLE 7-continued

| Px | STRUCTURE |
|---|---|
| 54 | 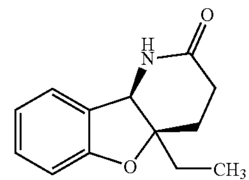 |
| 55 | 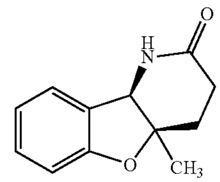 |
| 56 | 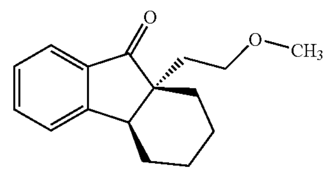 |
| 57 | 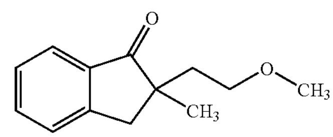 |
| 58 | 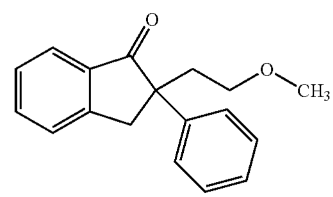 |
| 59 | 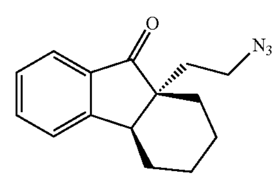 |

TABLE 8

| Px | STRUCTURE |
|---|---|
| 60 | 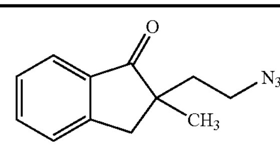 |
| 61 | 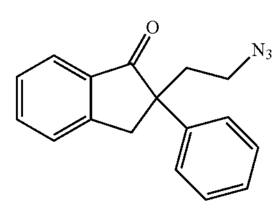 |

TABLE 8-continued
| Px | STRUCTURE |
|---|---|
| 62-1 | 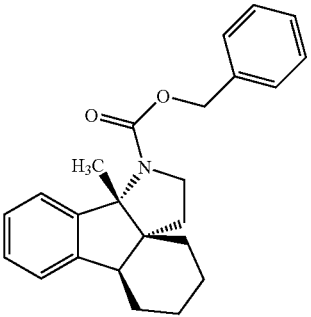 |
| 62-2 | 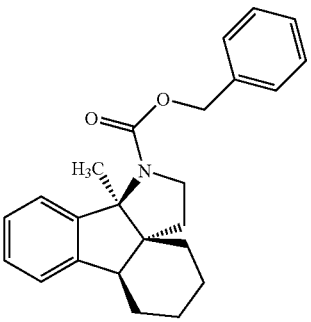 |
| 63-1 | 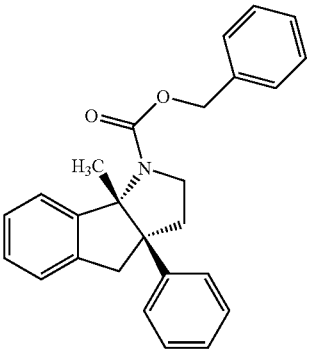 |
| 63-2 | 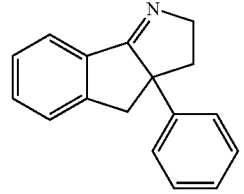 |
| 64 | 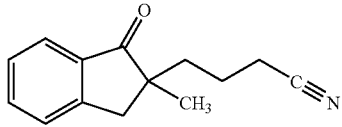 |
| 65 | 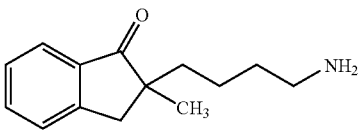 |
| 66 | 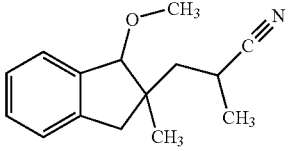 |
| 67 | 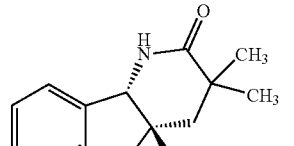 |
| 68 | 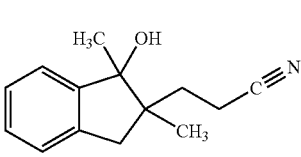 |
| 69 | 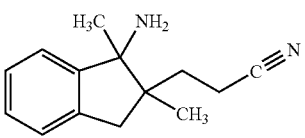 |
TABLE 9
| Px | STRUCTURE |
|---|---|
| 70-1 | 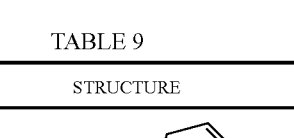 |
| 70-2 | 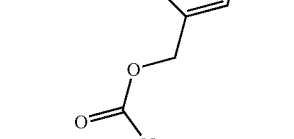 |

TABLE 9-continued

| Px | STRUCTURE |
|---|---|
| 71 | (structure) |
| 72-1 | (structure) |
| 72-2 | (structure) |
| 73 | (structure) |
| 74 | (structure) |
| 75 | (structure) |
| 76 | (structure) |
| 77 | (structure) |

TABLE 9-continued

| Px | STRUCTURE |
|---|---|
| 78 | (structure) |
| 79 | (structure) |

TABLE 10

| Px | STRUCTURE |
|---|---|
| 80 | (structure) |
| 81 | (structure) |
| 82 | (structure) |

TABLE 10-continued

| Px | STRUCTURE |
|---|---|
| 83 | (structure) |
| 84 | (structure) |
| 85 | (structure) |
| 86 | (structure) |
| 87 | (structure) |

TABLE 11

| Px | STRUCTURE |
|---|---|
| 88 | (structure) |
| 89 | (structure) |
| 90 | (structure) |

TABLE 11-continued

| Px | STRUCTURE |
|---|---|
| 91 | (structure) |
| 92 | (structure) |
| 93 | (structure) |
| 94 | (structure) |
| 95 | (structure) |

TABLE 12

| Px | STRUCTURE |
|---|---|
| 96 | (structure) |
| 97 | (structure) |
| 98 | (structure) |
| 99 | (structure) |
| 100 | (structure) |
| 101 | (structure) |
| 102 | (structure) |

TABLE 12-continued

| Px | STRUCTURE |
|----|-----------|
| 103 | (2-methoxyphenyl ketone with ethyl and propanenitrile substituents) |
| 104 | (2-hydroxyphenyl ketone with ethyl and propanenitrile substituents) |
| 105 | (2-triflyloxyphenyl ketone with ethyl and propanenitrile substituents) |
| 106 | (2-ethyl-2-(2-cyanoethyl)-benzofuran-3(2H)-one) |
| 107 | (ethyl 2-((4-bromophenyl)thio)propanoate) |
| 108 | (2-((4-bromophenyl)thio)propanoic acid) |
| 109 | (5-bromo-2-methylbenzo[b]thiophen-3(2H)-one) |

TABLE 13

| Ex | STRUCTURE | Sal |
|----|-----------|-----|
| 1 | 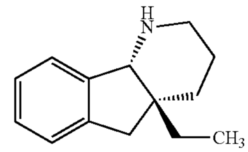 | CL |
| 2 | 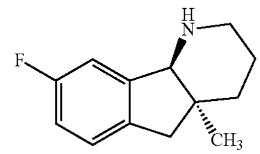 | CL |
| 3 | 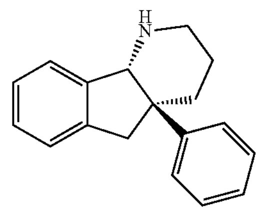 | CL |
| 4 | 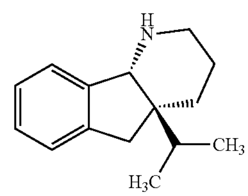 | CL |
| 5 | 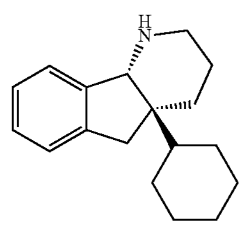 | CL |
| 6 | 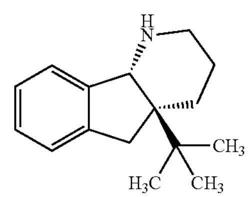 | CL |
| 7 | 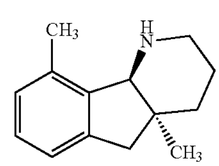 | CL |

TABLE 14

| Ex | STRUCTURE | Sal |
|---|---|---|
| 8 | (7-methyl indane-fused piperidine with 4a-CH₃) | CL |
| 9 | (8-methyl indane-fused piperidine with 4a-CH₃) | CL |
| 10 | (indane-fused piperidine with gem-dimethyl and 4a-CH₃) | CL |
| 11 | (methyl-substituted indane-fused piperidine with 4a-CH₃) | CL |
| 12 | (methoxy-substituted indane-fused piperidine with 4a-CH₃) | CL |
| 13 | (benzothiophene-fused piperidine with 4a-CH₃) | CL |
| 14 | (methylthiophene-fused cyclopenta-piperidine with 4a-CH₃) | CL |
| 15 | (methylthiophene-fused cyclopenta-piperidine with 4a-CH₃, alternate isomer) | CL |

TABLE 15

| Ex | STRUCTURE | Sal |
|---|---|---|
| 16 | (bromo-indane-fused piperidine with 4a-ethyl) | CL |
| 17 | (naphthalene-fused piperidine with 4a-CH₃) | CL |
| 18 | (benzofuran-fused piperidine with 4a-ethyl) | CL |
| 19 | (benzofuran-fused piperidine with 4a-CH₃) | CL |
| 20 | (benzo-fused morpholine/oxazine with CH₃) | CL |
| 21 | (benzo-fused oxazine indane with CH₃) | CL |
| 22 | (indane-fused piperidine with 4a-CH₃) | CL |
| 23 | (indane-fused piperidine with 4a-OH) | CL |

TABLE 16

| Ex | STRUCTURE | Sal |
|---|---|---|
| 24 | 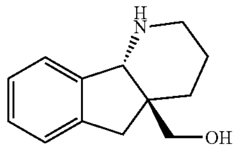 | CL |
| 25 | 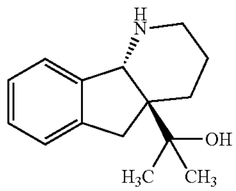 | CL |
| 26-1 | 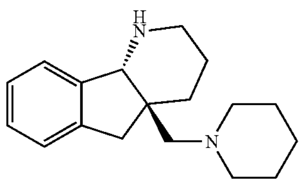 | CL |
| 26-2 | 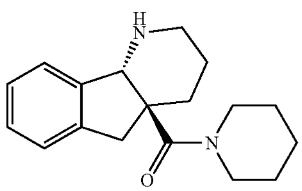 | CL |
| 27-1 | 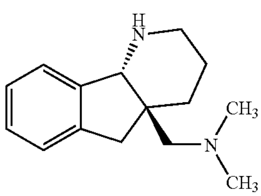 | CL |
| 27-2 | 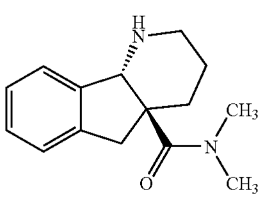 | CL |
| 28 | 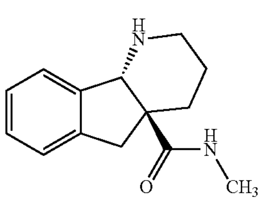 | CL |

TABLE 17

| Ex | STRUCTURE | Sal |
|---|---|---|
| 29-1 | 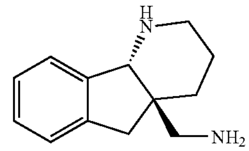 | CL |
| 29-2 | 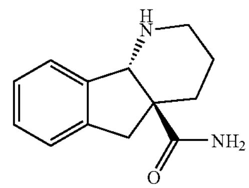 | CL |
| 30 | 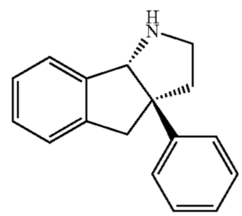 | CL |
| 31 | 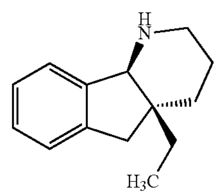 | CL |
| 32 | 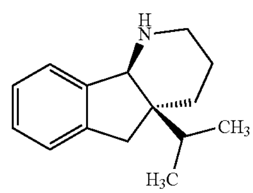 | CL |
| 33 | 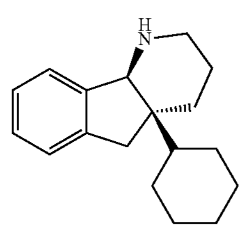 | CL |
| 34-1 | 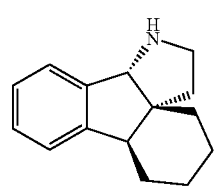 | CL |

TABLE 18

| Ex | STRUCTURE | Sal |
|---|---|---|
| 34-2 | 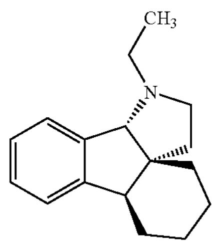 | CL |
| 35 | 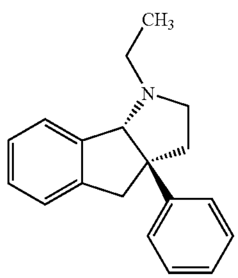 | CL |
| 36 | 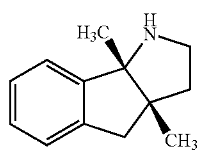 | CL |
| 37 | 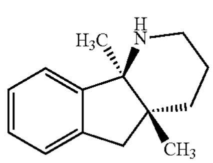 | CL |
| 38-1 | 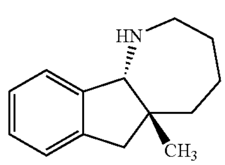 | CL |
| 38-2 | 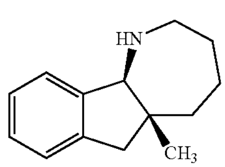 | CL |
| 39 | 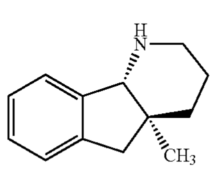 | CL |

TABLE 19

| Ex | STRUCTURE | Sal |
|---|---|---|
| 40-1 | 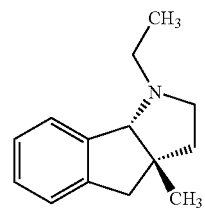 | CL |
| 40-2 | 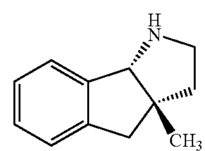 | MS |
| 41 | 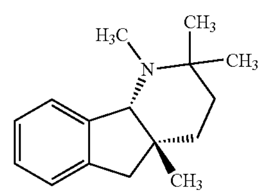 | MS |
| 42 | 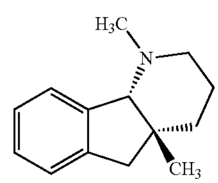 | MS |
| 43 | 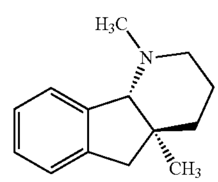 | BR |
| 44 | 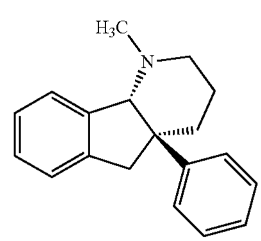 | MS |
| 45 | 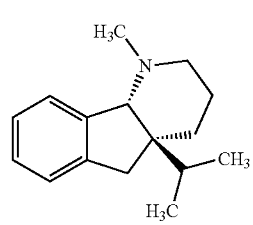 | MS |

TABLE 20

| Ex | STRUCTURE | Sal |
|---|---|---|
| 46 | (N-methyl hexahydroindeno-piperidine with cyclohexyl substituent) | MS |
| 47 | (N-methyl hexahydroindeno-piperidine with tert-butyl substituent) | MS |
| 48 | (N-methyl hexahydroindeno-piperidine with methyl on aromatic ring and CH3) | CL |
| 49 | (N-methyl hexahydroindeno-piperidine with methyl on aromatic ring and CH3) | CL |
| 50 | (N-methyl hexahydroindeno-piperidine with methyl on aromatic ring and CH3) | CL |
| 51 | (N-methyl hexahydroindeno-piperidine with CH3 substituent) | MS |
| 52 | (N-methyl hexahydroindeno-piperidine with three CH3 substituents) | MS |

TABLE 21

| Ex | STRUCTURE | Sal |
|---|---|---|
| 53 | (N-methyl hexahydroindeno-piperidine with cyclohexyl substituent) | MS |
| 54 | (N-methyl hexahydroindeno-piperidine with isopropyl substituent) | MS |
| 55 | (N-methyl hexahydroindeno-piperidine with methyl on aromatic ring and CH3) | CL |
| 56 | (N-methyl hexahydroindeno-piperidine with methoxy on aromatic ring and CH3) | BR |
| 57 | (N-methyl hexahydroindeno-piperidine with F on aromatic ring and CH3) | BR |
| 58 | (N-methyl hexahydroindeno-piperidine with CH3 substituent) | MS |

TABLE 22

| Ex | STRUCTURE | Sal |
|---|---|---|
| 59 | (N-isopropyl hexahydroindeno-piperidine with CH3 substituent) | MS |

TABLE 22-continued

| Ex | STRUCTURE | Sal |
|---|---|---|
| 60 | 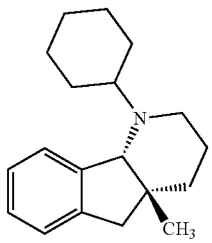 | MS |
| 61 | 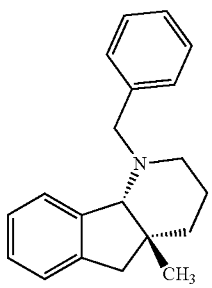 | MS |
| 62 | 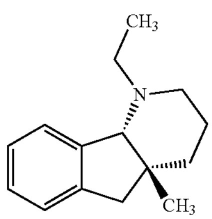 | CL |
| 63 | 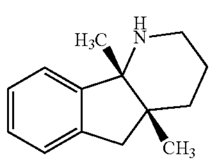 | CL |
| 64 | 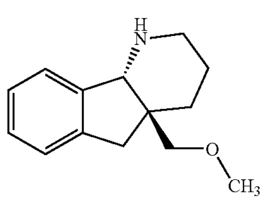 | CL |

TABLE 23

| Ex | STRUCTURE | Sal |
|---|---|---|
| 65 | 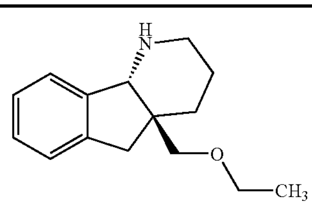 | CL |

TABLE 23-continued

| Ex | STRUCTURE | Sal |
|---|---|---|
| 66 | 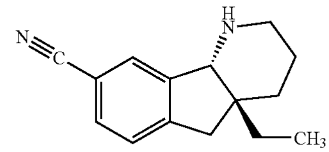 | CL |
| 67 | 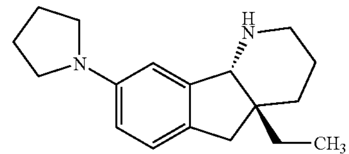 | OX |
| 68 | 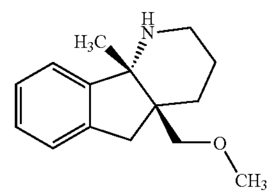 | CL |
| 69 | 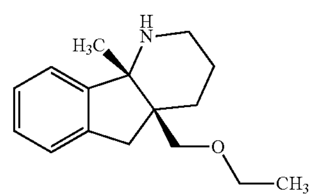 | CL |
| 70 | 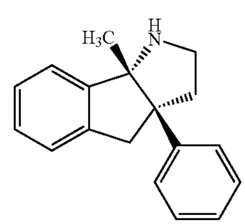 | CL |
| 71 | 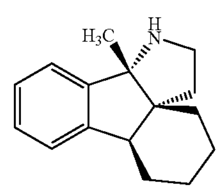 | CL |

TABLE 24

| Ex | STRUCTURE | Sal |
|---|---|---|
| 72 | 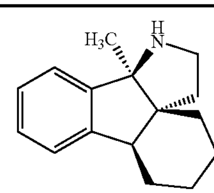 | CL |

TABLE 24-continued

| Ex | STRUCTURE | Sal |
|---|---|---|
| 73 | 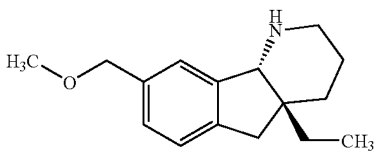 | FM |
| 74 | 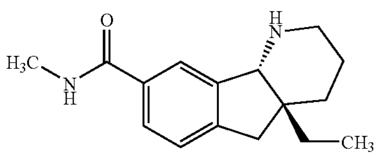 | FM |
| 75 | 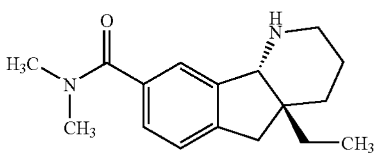 | FM |
| 76 | 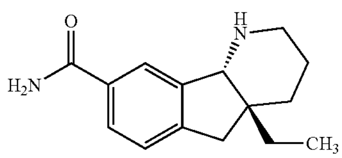 | FM |
| 77 | 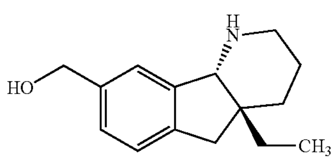 | FM |
| 78-1 | 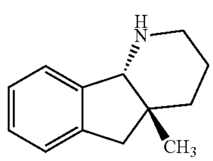 | Chiral |
| 78-2 | 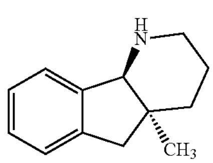 | Chiral |

TABLE 25

| Ex | STRUCTURE | Sal |
|---|---|---|
| 79-1 79-2 | chiral / or / chiral | |

TABLE 25-continued

| Ex | STRUCTURE | Sal |
|---|---|---|
| 80-1 80-2 | chiral / or / chiral | |
| 81 | | Chiral CL |
| 82 | | Chiral CL |
| 83-1 83-2 | chiral / or / chiral | CL |
| 84-1 84-2 | chiral / or / chiral | CL |

TABLE 26

| Px | Syn | Data |
|---|---|---|
| 1 | Px 1 | CI+: 200. |
| 2 | Px 2 | CI+: 214. |
| 3 | Px 3 | EI+: 295, 297. |
| 4 | Px 1 | EI+: 261. |
| 5 | Px 1 | CI+: 228. |
| 6 | Px 1 | FAB+: 242. |
| 7 | Px 1 | FAB+: 268. |
| 8 | Px 1 | CI+: 214. |
| 9 | Px 1 | EI+: 213. |
| 10 | Px 1 | CI+: 214. |
| 11 | Px 1 | EI+: 213. |
| 12 | Px 1 | EI+: 213. |
| 13 | Px 1 | EI+: 217. |
| 14 | Px 1 | CI+: 230. |
| 15 | Px 1 | ESI+: 220. |
| 16 | Px 1 | EI+: 292. |
| 17 | Px 1 | ESI+: 214. |
| 18 | Px 1 | ESI+: 202. |
| 19 | Px 19 | EI+: 201. |
| 20 | Px 20 | EI+: 215. |
| 21 | Px 21 | ESI+: 280, 282.(M − OH)+ |
| 22 | Px 19 | EI+: 263. |
| 23 | Px 19 | CI+: 230. |
| 24 | Px 19 | CI+: 244. |
| 25 | Px 19 | CI+: 270. |
| 26 | Px 19 | EI+: 215. |
| 27 | Px 19 | EI+: 215. |
| 28 | Px 19 | EI+: 215. |
| 29 | Px 19 | EI+: 215. |
| 30 | Px 19 | EI+: 215. |

TABLE 26-continued

| Px | Syn | Data |
|---|---|---|
| 31 | Px 19 | EI+: 219. |
| 32 | Px 19 | EI+: 231. |
| 33 | Px 19 | ESI+: 244.(M + Na)+ |

TABLE 27

| Px | Syn | Data |
|---|---|---|
| 34 | Px 19 | EI+: 294. |
| 35 | Px 19 | ESI+: 238.(M + Na)+ |
| 36 | Px 19 | ESI+: 200.(M − OH)+ |
| 37 | Px 19 | APCI+: 186.(M − OH)+ |
| 38 | Px 38 | EI+: 201. |
| 39 | Px 39 | EI+: 215. |
| 40 | Px 40 | ESI+: 298, 300. |
| 41 | Px 38 | EI+: 263. |
| 42 | Px 38 | CI+: 230. |
| 43 | Px 38 | CI+: 270. |
| 44 | Px 38 | EI+: 243. |
| 45 | Px 38 | FAB+: 216. |
| 46 | Px 38 | EI+: 215. |
| 47 | Px 38 | EI+: 215. |
| 48 | Px 38 | EI+: 215. |
| 49 | Px 38 | ESI+: 220. |
| 50 | Px 38 | EI+: 231. |
| 51-1 | Px 38 | ESI+: 222. |
| 51-2 | Px 38 | ESI+: 222. |
| 52 | Px 38 | ESI+: 295. |
| 53 | Px 38 | ESI+: 216. |
| 54 | Px 38 | ESI+: 218. |
| 55 | Px 38 | APCI+: 204. |
| 56 | Px 56 | EI+: 244. |
| 57 | Px 56 | EI+: 204. |
| 58 | Px 56 | EI+: 266. |
| 59 | Px 59 | CI+: 256. |
| 60 | Px 59 | FAB+: 216. |
| 61 | Px 59 | CI+: 278. |
| 62-1 | Px 62-1 | FAB+: 362. |
| 62-2 | Px 62-2 | FAB+: 362. |
| 63-1 | Px 63-1 | FAB+: 384. |
| 63-2 | Px 63-2 | CI+: 234. |
| 64 | Px 64 | CI+: 214. |

TABLE 28

| Px | Syn | Data |
|---|---|---|
| 65 | Px 65 | EI+: 217. |
| 66 | Px 66 | CI+: 230. |
| 67 | Px 67 | FAB+: 230. |
| 68 | Px 68 | CI+: 216. |
| 69 | Px 69 | CI+: 215. |

TABLE 28-continued

| Px | Syn | Data |
|---|---|---|
| 70-1 | Px 70-1 | EI+: 335. |
| 70-2 | Px 70-2 | EI+: 335. |
| 71 | Px 71 | EI+: 333. |
| 72-1 | Px 72-1 | ESI+: 262.(M + Na)+ |
| 72-2 | Px 72-2 | ESI+: 262.(M + Na)+ |
| 73 | Px 73 | ESI+: 204. |
| 74 | Px 73 | ESI+: 204. |
| 75 | Px 75 | EI+: 169. |
| 76 | Px 76 | EI+: 185. |
| 77 | Px 77 | CI+: 186.(M − OH)+ |
| 78 | Px 78 | EI+: 326. |
| 79 | Px 79 | NMR-DMSOd6: 1.46-1.56 (9H, m), 2.97-3.04 (3H, m), 3.90-4.15 (1H, m). |
| 80 | Px 79 | NMR-DMSOd6: 1.46-1.56 (9H, m), 2.92-3.16 (6H, m), 3.90-4.15 (1H, m). |
| 81 | Px 79 | NMR-DMSOd6: 1.46-1.56 (9H, m), 3.92-4.17 (1H, m), 6.00-6.48 (2H, m). |
| 82 | Px 82 | NMR-CDCl3: 1.47-1.55 (9H, m), 3.90-4.15 (1H, m), 4.63-4.69 (2H, m) |
| 83 | Px 83 | NMR-CDCl3: 1.47-1.55 (9H, m), 3.45-3.51 (3H, m), 3.90-4.15 (1H, m), 4.42 (2H, s) |
| 84 | Px 84 | CI+: 415. |
| 85 | Px 84 | CI+: 338. |
| 86 | Px 86 | CI+: 352. |
| 87 | Px 86 | CI+: 366. |
| 88 | Px 88 | ESI+: 361. |
| 89 | Px 89 | ESI+: 406. |
| 90 | Px 90 | EI+: 351. |
| 91 | Px 91 | CI+: 366. |
| 92 | Px 91 | CI+: 380. |

TABLE 29

| Px | Syn | Data |
|---|---|---|
| 93 | Px 93 | ESI+: 246. |
| 94 | Px 94 | ESI+: 232. |
| 95 | Px 95 | EI+: 298. |
| 96 | Px 95 | CI+: 231. |
| 97 | Px 95 | EI+: 244. |
| 98 | Px 95 | EI+: 258. |
| 99 | Px 99 | EI+: 215. |
| 100 | Px 100 | NMR-CDCl3: 1.64 (3H, s), 4.56 (1H, s). |
| 101 | Px 101 | ESI+: 237. |
| 102 | Px 102 | ESI+: 312.(M + Na)+ |
| 103 | Px 103 | ESI+: 232. |
| 104 | Px 104 | ESI−: 216. |
| 105 | Px 105 | ESI+: 350. |
| 106 | Px 106 | ESI+: 216. |
| 107 | Px 107 | ESI+: 289. |
| 108 | Px 108 | ESI−: 261. |
| 109 | Px 109 | ESI+: 241. |

TABLE 30

| Ex | Syn | Data |
|---|---|---|
| 1 | Ex 1 | EI+: 201.<br>NMR-DMSOd6: 0.84 (3H, t, J = 7.4 Hz), 1.38-1.80 (6H, m), 2.71 (1H, d, J = 15.7 Hz), 2.82 (1H, d, J = 15.7 Hz), 2.80-2.98 (2H, m), 4.30 (1H, s), 7.24-7.37 (3H, m), 7.68 (1H, d, J = 7.3 Hz), 8.97 (1H, brs), 10.04 (1H, brs). |
| 2 | Ex 1 | EI+: 205. |
| 3 | Ex 1 | EI+: 249. |
| 4 | Ex 1 | FAB+: 216. |
| 5 | Ex 1 | EI+: 255. |
| 6 | Ex 1 | FAB+: 230. |
| 7 | Ex 1 | EI+: 201. |
| 8 | Ex 1 | FAB+: 202. |
| 9 | Ex 1 | FAB+: 202. |
| 10 | Ex 1 | EI+: 215. |
| 11 | Ex 1 | EI+: 201. |

TABLE 30-continued

| Ex | Syn | Data |
|---|---|---|
| 12 | Ex 1 | EI+: 217.<br>NMR-DMSOd6: 1.15 (3H, s), 1.48-1.81 (4H, m), 2.53 (1H, d, J = 15.1 Hz),<br>2.76-2.97 (3H, m), 3.74 (3H, s), 4.23 (1H, brs),<br>6.89 (1H, dd, J = 8.1 Hz, 2.4 Hz), 7.23 (1H, d, J = 8.1 Hz), 7.39 (1H, d, J = 2.4 Hz),<br>9.03 (1H, br), 10.23 (1H, br). |
| 13 | Ex 13 | ESI+: 206.<br>NMR-DMSOd6: 1.44 (3H, s), 1.76-1.95 (3H, m), 2.03-2.13 (1H,<br>m), 2.90 (1H, brs), 3.05 (1H, m), 4.48 (1H, s), 7.21 (1H, t, J = 7.3 Hz),<br>7.37 (1H, t, J = 7.3 Hz), 7.43 (1H, d, J = 7.3 Hz), 7.65 (1H, d,<br>J = 7.3 Hz), 8.32 (1H, brs), 10.47 (1H, brs). |
| 14 | Ex 13 | ESI+: 208.0.<br>NMR-DMSOd6: 1.15 (3H, s), 1.4-2.0 (4H, m), 2.45 (3H, s),<br>2.2-3.0 (4H, m), 4.12 (1H, m), 6.69 (1H, s), 8.57 (1H, br-s),<br>10.12 (1H, br-s). |
| 15 | Ex 13 | ESI+: 208.1.<br>NMR-DMSOd6: 1.18 (3H, s), 1.4-2.0 (4H, m), 2.43 (3H, s),<br>2.2-3.0 (4H, m), 4.02 (1H, m), 6.85 (1H, s), 8.69 (1H, br-s),<br>10.08 (1H, br-s). |
| 16 | Ex 13 | FAB+: 281. |

TABLE 31

| Ex | Syn | Data |
|---|---|---|
| 17 | Ex 13 | ESI+: 202.<br>NMR-DMSO6: 0.89 (3H, s), 1.29 (1H, m), 1.58-1.84 (4H, m),<br>2.3-2.4 (1H, m), 2.8-3.02 (3H, m), 2.90-3.02 (1H, m), 3.15 (1H,<br>m), 3.98 (1H, d, J = 9.7 Hz), 7.2-7.3 (2H, m), 7.33 (1H, t, J = 7.2 Hz),<br>7.52 (1H, d, J = 7.2 Hz), 8.64 (1H, brs), 9.37 (1H, brs). |
| 18 | Ex 13 | EI+: 203.<br>NMR-DMSO6: 0.86 (3H, t, J = 7.4 Hz), 1.55-1.82 (4H, m),<br>1.87-1.97 (1H, m), 2.03-2.12 (1H, m), 2.81-2.90 (1H, m),<br>2.90-3.02 (1H, m), 4.62 (1H, s), 6.94 (1H, d, J = 8.0 Hz), 6.99 (1H, t, J = 7.2 Hz),<br>7.34 (1H, t, J = 7.2 Hz), 7.61 (1H, d, J = 7.2 Hz), 8.89 (1H, brs),<br>10.38 (1H, brs). |
| 19 | Ex 13 | ESI+: 190. |
| 20 | Ex 13 | ESI+: 190.<br>NMR-DMSO6: 1.53 (3H, s), 2.7-3.2 (4H, m), 3.7 (1H, m),<br>3.9 (1H, m), 4.56 (1H, s), 7.3 (1H, m), 7.76 (1H, d, J = 7.2 Hz), 9.94 (1H,<br>brs), 10.62 (1H, brs). |
| 21 | Ex 13 | ESI+: 190.<br>NMR-DMSO6: 1.22 (3H, s), 2.6-3.6 (4H, m), 3.8-4.2 (2H,<br>m), 4.48 (1H, d, J = 10.5 Hz), 7.2-7.4 (3H, m), 7.5 (1H, m), 9.65 (1H,<br>brs), 11.40 (1H, brs). |
| 22 | Ex 22 | CI+: 188.<br>NMR-DMSOd6: 1.12 (3H, s), 1.52-1.81 (4H, m), 2.59 (1H, d, J = 15.6 Hz),<br>2.80-2.94 (2H, m), 2.98 (1H, d, J = 15.6 Hz), 4.24 (1H,<br>s), 7.25-7.37 (3H, m), 7.69 (1H, d, J = 7.3 Hz), 8.85 (1H, brs),<br>10.22 (1H, brs). |
| 23 | Ex 22 | ESI+: 190.<br>NMR-DMSO6: 1.55-1.89 (4H, m), 2.70-2.80 (4H, m), 4.63 (1H,<br>s), 7.12-7.22 (3H, m), 7.25-7.31 (1H, m). |
| 24 | Ex 22 | ESI+: 204. |
| 25 | Ex 22 | ESI+: 232.<br>NMR-DMSO6: 0.96 (3H, s), 1.19 (3H, s), 1.43-1.56 (2H, m),<br>1.82-1.94 (1H, m), 1.96-2.07 (1H, m), 2.64-2.74 (1H, m),<br>2.73 (1H, d, J = 16.9 Hz), 2.80-2.92 (1H, m), 3.01 (1H, d, J = 16.9 Hz),<br>4.84-4.98 (2H, br), 7.25-7.35 (3H, m), 7.70-7.78 (1H, m),<br>9.23 (2H, brs). |

TABLE 32

| Ex | Syn | Data |
|---|---|---|
| 26-1 | Ex 26-1 | EI+: 270.<br>NMR-DMSOd6: 1.37-1.81 (6H, m), 1.82-2.16 (3H, m),<br>2.63-2.78 (1H, m), 2.92-3.13 (1H, m), 3.05 (1H, d, J = 15.7 Hz),<br>3.12 (1H, d, J = 15.7 Hz), 3.15-3.27 (1H, m), 3.27-3.40 (1H, m),<br>3.40-3.56 (1H, m), 3.69-3.80 (1H, m), 4.87 (1H, s), 7.29-7.41 (3H,<br>m), 7.75 (1H, d, J = 7.0 Hz), 9.50-9.72 (1H, br), 10.35 (1H, brs),<br>10.4-10.6 (1H, br). |
| 26-2 | Ex 26-2 | CI+: 285.<br>NMR-DMSOd6: 1.32-1.73 (9H, m), 1.92-2.07 (1H, m), |

TABLE 32-continued

| Ex | Syn | Data |
|---|---|---|
| | | 2.62-2.78 (1H, m), 3.25 (1H, d, J = 15.5 Hz), 3.30 (1H, d, J = 15.5 Hz), 5.21 (1H, s), 7.25-7.38 (3H, m), 7.91 (1H, d, J = 6.7 Hz), 8.75 (1H, brs), 10.21 (1H, brs). |
| 27-1 | Ex 26 | FAB+: 231. |
| 27-2 | Ex 26 | FAB+: 245. |
| 28 | Ex 26 | ESI+: 231. |
| 29-1 | Ex 26 | FAB+: 203. |
| 29-2 | Ex 26 | FAB+: 217. |
| 30 | Ex 30 | FAB+: 236. NMR-DMSOd6: 2.38-2.44 (2H, m), 3.15-3.25 (2H, m), 3.29-3.28 (1H, m), 3.54 (1H, d, J = 17.1 Hz), 5.32 (1H, s), 7.22-7.44 (8H, m), 7.62 (1H, d, J = 7.2 Hz), 9.25 (1H, brs), 10.4 (1H, brs). |
| 31 | Ex 31 | CI+: 202. NMR-DMSOd6: 0.65-0.78 (4H, m), 1.56-1.80 (4H, m), 1.90-2.01 (1H, m), 2.46 (1H, d, J = 14.8 Hz), 2.86 (1H, d, J = 14.8 Hz), 2.98-3.15 (1H, m), 3.35-3.43 (1H, m), 4.29-4.37 (1H, m), 7.20-7.32 (3H, m), 7.53-7.58 (1H, m), 8.83 (1H, brs), 11.02 (1H, brs). |
| 32 | Ex 31 | FAB+: 216. |
| 33 | Ex 31 | FAB+: 256. |
| 34-1 | Ex 34-1 | FAB+: 214. NMR-DMSOd6: 1.20-1.34 (1H, m), 1.35-1.52 (3H, m), 1.52-1.70 (3H, m), 1.83-1.95 (2H, m), 1.95-2.06 (1H, m), 3.10-3.25 (2H, m), 3.31-3.44 (1H, m), 4.63 (1H, s), 7.27-7.34 (2H, m), 7.35-7.42 (1H, m), 7.53-7.59 (1H, m), 9.16 (1H, brs), 9.97 (1H, br s). |

TABLE 33

| Ex | Syn | Data |
|---|---|---|
| 34-2 | Ex 34-2 | FAB+: 242. NMR-CD3OD: 1.13-1.27 (1H, m), 1.32-1.65 (8H, m), 1.71-1.83 (1H, m), 1.85-1.93 (1H, m), 2.05-2.14 (1H, m), 2.15-2.24 (1H, m), 2.24-2.35 (1H, m), 3.24-3.36 (1H, m), 3.44-3.54 (1H, m), 3.55-3.66 (1H, m), 3.83-3.92 (1H, m), 4.38 (1H, s), 7.32-7.40 (2H, m), 7.46-7.57 (1H, m), 7.58 (1H, d, J = 7.5 Hz). |
| 35 | Ex 34 | FAB+: 264. |
| 36 | Ex 36 | FAB+: 188. |
| 37 | Ex 37 | ESI+: 202. NMR-DMSOd6: 0.94 (3H, s), 1.44 (3H, s), 1.59 (1H, dd, J = 4.5, 12.7 Hz), 1.74-1.84 (1H, m), 1.86-2.02 (1H, m), 2.07 (1H, dt, J = 5.2, 12.7 Hz), 7.20-7.27 (2H, m), 7.27-7.33 (1H, m), 7.54-7.60 (1H, m), 8.50-8.90 (1H, br-m), 10.7-11.0 (1H, br-m). |
| 38-1 | Ex 38-1 | ESI+: 202. NMR-DMSOd6: 1.10 (3H, s), 1.52-1.80 (3H, m), 1.80-2.02 (3H, m), 2.69 (1H, d, J = 16.4 Hz), 3.06-3.20 (1H, m), 3.16 (1H, d, J = 16.4 Hz), 3.23-3.35 (1H, m), 7.26-7.33 (2H, m), 7.33-7.40 (1H, m), 7.68 (1H, d, J = 7.3 Hz), 9.23 (2H, brs). |
| 38-2 | Ex 38-2 | ESI+: 202. NMR-DMSOd6: 0.96 (3H, s), 1.52-1.66 (1H, m), 1.79-2.00 (5H, m), 2.68 (1H, d, J = 15.4 Hz), 2.83 (1H, d, J = 15.4 Hz), 3.05-3.19 (1H, m), 3.46-3.57 (1H, m), 4.66-4.76 (1H, m), 7.22-7.32 (3H, m), 7.68-7.76 (1H, m), 8.86-9.00 (1H, br), 10.85-11.15 (1H, br). |
| 39 | Ex 39 | FAB+: 188. NMR-DMSOd6: 0.86 (3H, s), 1.73-1.95 (4H, m), 2.65 (2H, s), 3.07 (1H, brs), 3.39 (1H, d, J = 12.2 Hz), 4.24 (1H, d, J = 11.5 Hz), 7.21-7.27 (2H, m), 7.28-7.33 (1H, m), 7.52-7.58 (1H, m), 8.75 (1H, brs), 10.89 (1H, brs). |
| 40-1 | Ex 40-1 | FAB+: 174. |
| 40-2 | Ex 40-2 | FAB+: 202. |
| 41 | Ex 41 | CI+: 230. NMR-CD3OD: 1.04 (3H, s), 1.44 (3H, s), 1.45 (3H, s), 1.81-2.06 (4H, m), 2.55 (1H, d, J = 16.1 Hz), 2.67 (3H, s), 2.88 (3H, s), 3.38 (1H, d, J = 16.1 Hz), 4.21 (1H, s), 7.30-7.38 (1H, m), 7.41-7.48 (2H, m), 7.60 (1H, d, J = 7.6 Hz). |

TABLE 34

| Ex | Syn | Data |
|---|---|---|
| 42 | Ex 42 | FAB+: 202.<br>NMR-CD3OD: 1.02 (3H, s), 1.70-1.84 (1H, m), 1.88-2.05 (3H, m), 2.56 (1H, d, J = 16.1 Hz), 2.65 (3H, s), 2.94 (3H, s), 3.02-3.14 (1H, m), 3.31 (1H, d, J = 16.1 Hz), 3.35-3.42 (1H, m), 4.00 (1H, s), 7.32-7.39 (1H, m), 7.40-7.49 (2H, m), 7.62 (1H, d, J = 7.4 Hz). |
| 43 | Ex 42 | EI+: 201. |
| 44 | Ex 42 | EI+: 263. |
| 45 | Ex 42 | FAB+: 230. |
| 46 | Ex 42 | FAB+: 270. |
| 47 | Ex 42 | EI+: 243. |
| 48 | Ex 42 | FAB+: 216. |
| 49 | Ex 42 | FAB+: 216. |
| 50 | Ex 42 | EI+: 215. |
| 51 | Ex 42 | FAB+: 216. |
| 52 | Ex 42 | FAB+: 230. |
| 53 | Ex 42 | FAB+: 270. |
| 54 | Ex 42 | FAB+: 230. |
| 55 | Ex 42 | FAB-MS (M + 1)+: 216. |
| 56 | Ex 42 | EI+: 231.<br>NMR-DMSOd6: 0.92 (3H, s), 1.56-1.71 (1H, m), 1.76-1.98 (3H, m), 2.32 (1H, d, J = 15.8 Hz), 2.84 (3H, d, J = 5.0 Hz), 2.98-3.40 (3H, m), 3.80 (3H, s), 4.02 (1H, d, J = 8.9 Hz), 7.00 (1H, dd, J = 8.4 Hz, 2.1 Hz), 7.22 (1H, d, J = 2.1 Hz), 7.33 (1H, d, J = 8.4 Hz), 8.93 (1H, br). |
| 57 | Ex 42 | EI+: 219. |
| 58 | Ex 42 | EI+: 215.<br>NMR-CD3OD: 0.84 (3H, t, J = 7.5 Hz), 1.30 (2H, J = 7.5 Hz), 1.67-1.78 (1H, m), 1.86-2.06 (3H, m), 2.66 (3H, s), 2.74 (1H, d, J = 16.5 Hz), 2.94 (3H, s), 2.99-3.10 (1H, m), 3.18 (1H, d, J = 16.5 Hz), 3.34-3.42 (1H, m), 4.01 (1H, s), 7.30-7.38 (1H, m), 7.40-7.48 (2H, m), 7.61 (1H, d, J = 7.4 Hz). |

TABLE 35

| Ex | Syn | Data |
|---|---|---|
| 59 | Ex 59 | EI+: 229.<br>NMR-CD3OD: 1.03 (3H, s), 1.29 (3H, d, J = 6.6 Hz), 1.49 (3H, d, J = 6.6 Hz), 1.71-1.81 (1H, m), 1.85-2.06 (3H, m), 2.54 (1H, d, J = 16.2 Hz), 2.67 (3H, s), 2.83-2.96 (1H, m), 3.35-3.44 (1H, m), 3.44 (1H, 16.2 Hz), 3.94-4.08 (1H, m), 4.23 (1H, s), 7.30-7.38 (1H, m), 7.41-7.49 (2H, m), 7.57 (1H, d, J = 7.6 Hz). |
| 60 | Ex 59 | EI+: 269. |
| 61 | Ex 59 | FAB+: 278. |
| 62 | Ex 62 | EI+: 215. |
| 63 | Ex 63 | CI+: 202.<br>NMR-DMSOd6: 1.08 (3H, s), 1.40-1.80 (4H, m), 1.51 (3H, s), 2.62-2.78 (1H, m), 2.68 (1H, d, J = 15.7 Hz), 2.91 (1H, d, J = 15.7 Hz), 2.95-3.07 (1H, m), 7.26-7.37 (3H, m), 7.60-7.67 (1H, m), 9.22 (1H, brs), 9.78 (1H, brs). |
| 64 | Ex 63 | ESI+: 218. |
| 65 | Ex 63 | ESI+: 232. |
| 66 | Ex 63 | ESI+: 227.<br>NMR-DMSOd6: 0.84 (3H, t, J = 7.5 Hz), 1.34-1.52 (2H, m), 1.56-1.80 (4H, m), 2.74-3.00 (4H, m), 4.45 (1H, s), 7.56 (1H, d, J = 7.8 Hz), 7.82 (1H, dd, J = 7.8, 1.4 Hz), 8.22 (1H, s), 9.52 (1H, brs), 10.31 (1H, brs). |
| 67 | Ex 63 | ESI+: 271.<br>NMR-DMSOd6: 0.84 (3H, t, J = 7.5 Hz), 1.37-1.78 (6H, m), 1.89-2.00 (4H, m), 2.54-2.70 (2H, m), 2.80-2.99 (2H, m), 3.11-3.25 (4H, m), 4.23 (1H, s), 6.49 (1H, dd, J = 8.2, 1.9 Hz), 6.76 (1H, s), 7.11 (1H, d, J = 8.2 Hz). |
| 68 | Ex 63 | ESI+: 232.<br>NMR-DMSOd6: 1.35-1.46 (1H, m), 1.53 (3H, s), 1.54-1.67 (1H, m), 1.72-1.90 (2H, m), 2.64-2.75 (1H, m), 2.80 (1H, d, J = 16.0 Hz), 2.92 (1H, d, J = 16.0 Hz), 2.96-3.07 (1H, m), 3.26 (3H, s), 3.27 (1H, d, J = 9.3 Hz), 3.51 (1H, d, J = 9.3 Hz), 7.27-7.37 (3H, m), 7.68 (1H, d, J = 6.3 Hz), 9.39 (1H, brs), 9.75 (1H, brs). |

TABLE 36

| Ex | Syn | Data |
|---|---|---|
| 69 | Ex 63 | ESI+: 246.<br>NMR-DMSOd6: 1.10 (3H, t, J = 7.0 Hz), 1.36-1.48 (1H, m), 1.53 (3H, s), 1.56-1.68 (1H, m), 1.72-1.90 (2H, m), 2.66-2.77 (1H, m), 2.82 (1H, d, J = 16 Hz), 2.92 (1H, d, J = 16 Hz), 2.96-3.08 (1H, m), 3.28 (1H, d, J = 9.4 Hz), 3.42 (2H, q, J = 7.0 Hz), 3.53 (1H, d, J = 9.4 Hz), 7.26-7.38 (3H, m), 7.61-7.70 (1H, m), 9.28 (1H, brs), 9.66 (1H, brs). |
| 70 | Ex 63 | EI+: 249. |
| 71 | Ex 63 | FAB+: 228.<br>NMR-DMSOd6: 1.05-1.37 (3H, m), 1.42-1.55 (3H, m), 1.59 (3H, s), 1.74-1.88 (1H, m), 1.89-2.03 (2H, m), 2.20-2.30 (1H, m), 3.15-3.29 (2H, m), 3.35-3.48 (1H, m), 7.29 (1H, d, J = 7.4 Hz), 7.32 (1H, t, J = 7.4 Hz), 7.41 (1H, t, J = 7.4 Hz), 7.51 (1H, d, J = 7.4 Hz), 9.18 (1H, brs), 9.89 (1H, brs). |
| 72 | Ex 63 | FAB+: 228.<br>NMR-DMSOd6: 0.79-0.90 (1H, m), 0.93-1.09 (1H, m), 1.14-1.33 (2H, m), 1.38 (3H, s), 1.39-1.52 (2H, m), 1.61-1.74 (1H, m), 1.89-1.98 (1H, m), 2.01-2.13 (1H, m), 2.22-2.32 (1H, m), 3.14-3.20 (1H, m), 3.82-4.00 (2H, m), 7.20-7.34 (4H, m), 9.12 (1H, brs), 9.97 (1H, brs). |
| 73 | Ex 73 | ESI+: 246.<br>NMR-DMSOd6: 0.85 (3H, t, J = 7.6 Hz), 1.30-1.70 (6H, m), 2.61-2.71 (1H, m), 2.65 (2H, s), 2.78-2.86 (1H, m), 3.28 (3H, s), 4.14 (1H, s), 4.38 (2H, s), 6.50 (2H, s), 7.15-7.27 (2H, m), 7.43 (1H, s). |
| 74 | Ex 73 | ESI+: 259.<br>NMR-DMSOd6: 0.86 (3H, t, J = 7.5 Hz), 1.24-1.74 (6H, m), 2.59-2.70 (1H, m), 2.69 (2H, s), 2.77 (3H, d, J = 4.5 Hz), 2.79-2.87 (1H, m), 4.17 (1H, s), 6.52 (2H, s), 7.33 (1H, d, J = 7.8 Hz), 7.72 (1H, dd, J = 7.8, 1.4 Hz), 7.99 (1H, s), 8.40-8.47 (1H, m). |
| 75 | Ex 73 | FAB+: 273. |
| 76 | Ex 73 | FAB+: 245. |
| 77 | Ex 73 | ESI+: 232.<br>NMR-DMSOd6: 0.86 (3H, t, J = 7.5 Hz), 1.22-1.74 (6H, m), 2.54-2.64 (1H, m), 2.59 (2H, s), 2.72-2.80 (1H, m), 4.04 (1H, s), 4.47 (2H, s), 6.46 (1H, s), 7.14-7.22 (2H, m), 7.37 (1H, m). |

TABLE 37

| Ex | Syn | Data |
|---|---|---|
| 78-1 | Ex 78-1 | $[\alpha]^{25}_D = -26.51$ (c = 1.467, l = 1, MeOH), 93% ee<br>NMR-CDCl3: 1.21 (3H, s), 1.33-1.64 (4H, m), 1.78 (1H, br), 2.57 (1H, d, J = 15.3 Hz), 2.63-2.78 (2H, m), 2.74 (1H, d, J = 15.3 Hz), 3.87 (1H, s), 7.14-7.24 (3H, m), 7.28-7.34 (1H, m). |
| 78-2 | Ex 78-2 | $[\alpha]^{25}_D = +28.26$ (c = 1.04, l = 1, MeOH), 97% ee |
| 79-1 | Ex 79-1 | $[\alpha]^{25}_D = -17.11$ (c = 2.413, l = 1, MeOH), 96% ee<br>NMR-CDCl3: 0.93 (3H, t, J = 7.4 Hz), 1.25-1.41 (2H, m), 1.48-1.60 (3H, m), 1.73-2.05 (2H, m), 2.57 (1H, d, J = 15.1 Hz), 2.66 (1H, d, J = 15.1 Hz), 2.62-2.70 (1H, m), 2.72-2.79 (1H, m), 3.97 (1H, s), 7.15-7.25 (3H, m), 7.31-7.37 (1H, m). |
| 79-2 | Ex 79-2 | $[\alpha]^{25}_D = +19.95$ (c = 2.040, l = 1, MeOH), 97% ee |
| 80-1 | Ex 80-1 | $[\alpha]^{25}_D = -41.45$ (c = 1.563, l = 1, MeOH), 98% ee<br>NMR-CDCl3: 1.13 (3H, s), 1.15 (3H, s), 1.28-1.62 (5H, m), 2.51-2.59 (1H, m), 2.58 (1H, d, J = 15.1 Hz), 2.70 (1H, d, J = 15.1 Hz), 2.77-2.83 (1H, m), 7.14-7.23 (4H, m). |
| 80-2 | Ex 80-2 | $[\alpha]^{25}_D = +41.65$ (c = 1.527, l = 1, MeOH), 98% ee |
| 81 | Ex 81 | ESI+: 188.<br>NMR-DMSOd6: 1.11 (3H, s), 1.51-1.81 (4H, m), 2.59 (1H, d, J = 15.6 Hz), 2.82-2.94 (2H, m), 2.99 (1H, d, J = 15.6 Hz), 4.24 (1H, s), 7.24-7.38 (3H, m), 7.65 (1H, d, J = 7.4 Hz), 8.75 (1H, brs), 10.04 (1H, brs). |
| 82 | Ex 82 | EI+: 187.<br>NMR-DMSOd6: 1.10 (3H, s), 1.52-1.81 (4H, m), 2.59 (1H, d, J = 15.6 Hz), 2.84-2.94 (2H, m), 2.99 (1H, d, J = 15.6 Hz), 4.24 (1H, s), 7.26-7.39 (3H, m), 7.63 (1H, d, J = 7.3 Hz), 8.71 (1H, brs), 9.92 (1H, brs). |

TABLE 38

| Ex | Syn | Data |
|---|---|---|
| 83-1 | Ex 83-1 | EI+: 201.<br>NMR-DMSOd6: 0.84 (3H, t, J = 7.4 Hz), 1.34-1.80 (6H, m), 2.71 (1H, d, J = 15.7 Hz), 2.83 (1H, d, J = 15.7 Hz), 2.80-2.98 (2H, m), 4.30 (1H, s), 7.25-7.38 (3H, m), 7.63 (1H, d, J = 7.4 Hz), 8.82 (1H, brs), 9.81 (1H, brs). |
| 83-2 | Ex 83-2 | EI+: 201.<br>NMR-DMSOd6: 0.84 (3H, t, J = 7.4 Hz), 1.34-1.81 (6H, m), 2.71 (1H, d, J = 15.7 Hz), 2.83 (1H, d, J = 15.7 Hz), 2.78-2.98 (2H, m), 4.30 (1H, s), 7.24-7.39 (3H, m), 7.65 (1H, d, J = 7.4 Hz), 8.89 (1H, brs), 9.87 (1H, brs). |
| 84-1 | Ex 84-1 | ESI+: 202.<br>NMR-DMSOd6: 1.07 (3H, s), 1.38-1.81 (4H, m), 1.51 (3H, s), 2.62-2.78 (1H, m), 2.68 (1H, d, J = 15.8 Hz), 2.93 (1H, d, J = 15.8 Hz), 2.87-3.07 (1H, m), 7.27-7.36 (3H, m), 7.58-7.64 (1H, m), 9.13 (1H, brs), 9.68 (1H, brs). |
| 84-2 | Ex 84-2 | ESI+: 202.<br>NMR-DMSOd6: 1.10 (3H, s), 1.39-1.81 (4H, m), 1.52 (3H, s), 2.62-2.74 (1H, m), 2.69 (1H, d, J = 15.7 Hz), 2.90 (1H, d, J = 15.7 Hz), 2.95-3.06 (1H, m), 7.25-7.35 (3H, m), 7.63-7.70 (1H, m), 9.33 (1H, brs), 9.91 (1H, brs). |

Further, the structures of the other compounds of the formula (I) are shown in Table 39 to Table 40. These can be easily prepared by using the production processes as described above, the methods described in the Examples, the methods that are apparent to a person skilled in the art, or modified methods thereof.

Further, in Tables, No represents the compound number.

TABLE 39

| No | STRUCTURE |
|---|---|
| 1 | [structure] |
| 2 | [structure] |
| 3 | [structure] |
| 4 | [structure] |
| 5 | [structure] |
| 6 | [structure] |
| 7 | [structure] |
| 8 | [structure] |
| 9 | [structure] |
| 10 | [structure] |

TABLE 40

| No | STRUCTURE |
|---|---|
| 11 | 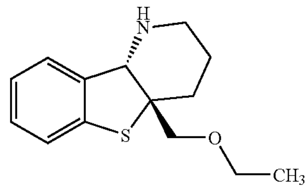 |
| 12 | 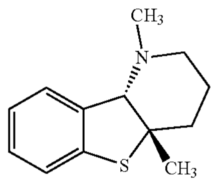 |
| 13 | 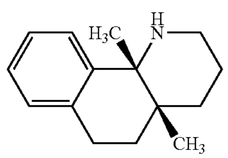 |
| 14 | 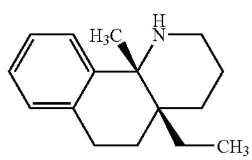 |
| 15 | 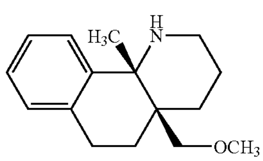 |
| 16 | 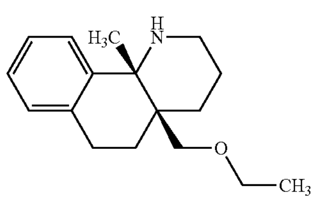 |
| 17 | 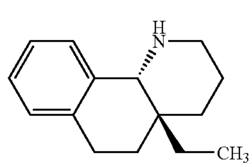 |
| 18 | 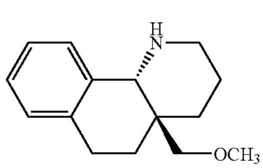 |

TABLE 40-continued

| No | STRUCTURE |
|---|---|
| 19 | 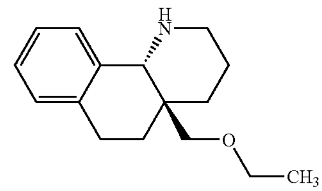 |
| 20 | 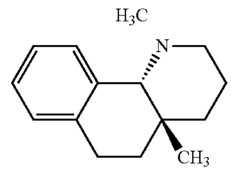 |

INDUSTRIAL APPLICABILITY

The compound according to the present invention has an NMDA receptor inhibitory action and can be used as a prophylactic and/or therapeutic agent for Alzheimer's disease, cerebrovascular dementia, Parkinson's disease, ischemic apoplexy, pain, intractable depression, attention deficit hyperactivity disorder, migraines, schizophrenia, generalized anxiety disorder, obsessive-compulsive disorder, autism, bulimia, drug addiction, or the like.

The invention claimed is:

1. A compound of the formula (I) or a pharmaceutically acceptable salt thereof:

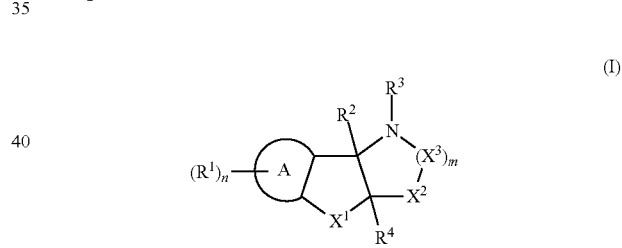

(I)

wherein Ring A represents a benzene ring, $R^1$ represents $C_{1-6}$ alkyl which may be substituted with one or more groups selected from the group consisting of —OH, —O—$C_{1-6}$ alkyl, amino which may be substituted with one or two $C_{1-6}$ alkyl, and oxo; —O—$C_{1-6}$ alkyl; halogen; cyano; or cyclic amino, n represents an integer of 0 to 4, $R^2$ represents —H or $C_{1-6}$ alkyl, $R^3$ represents $C_{1-6}$ alkyl which may be substituted with phenyl, cycloalkyl, or —H, $R^4$ represents $C_{1-6}$ alkyl which may be substituted with one or more groups selected from the group consisting of —OH, —O—$C_{1-6}$ alkyl, amino which may be substituted with one or two $C_{1-6}$ alkyl, oxo, and cyclic amino, $X^1$ represents —$CH_2$— or —$CH(R^0)$—, $X^2$ represents —$C(R^A)(R^B)$—, $X^3$ represents —$C(R^C)(R^D)$—, m represents an integer of 1 to 3, $R^0$ represents —H, or $R^0$ is combined with $R^4$ to represent $C_{3-5}$ alkylene, and, $R^A$, $R^B$, $R^C$, and $R^D$ independently represent —H or $C_{1-6}$ alkyl, wherein, in the case where m represents 2 or 3, each of $R^C$ and $R^D$ may be the same as or different from each other, and provided that 2-(1,2,3,4,5,9b-hexahydro-4aH-indeno[1,2-b]pyridin-4a-yl)-N,N-dimethylethaneamine is excluded.

2. The compound or a pharmaceutically acceptable salt thereof of claim 1, wherein $X^1$ is —CH$_2$—, $X^2$ is —CH$_2$—, $X^3$ is —CH$_2$—, and m is 2.

3. The compound or a pharmaceutically acceptable salt thereof of claim 2, wherein $R^4$ is methyl, ethyl, isopropyl, methoxymethyl, or ethoxymethyl.

4. The compound or a pharmaceutically acceptable salt thereof of claim 3, wherein $R^3$ is —H, methyl, or ethyl.

5. The compound or a pharmaceutically acceptable salt thereof of claim 4, wherein $R^2$ is —H or methyl.

6. The compound or a pharmaceutically acceptable salt thereof of claim 5, wherein n is 0.

7. The compound or a pharmaceutically acceptable salt thereof of claim 1, which is (4aRS,9bRS)-4-a-methyl-2,3,4,4a,5,9b-hexahydro-1H-indeno[1,2-b]pyridine, (4aRS,9bRS)-1,4-a-dimethyl-2,3,4,4a,5,9b-hexahydro-1H-indeno[1,2-b]pyridine, (4aRS,9bRS)-4-a-ethyl-2,3,4,4a,5,9b-hexahydro-1H-indeno[1,2-b]pyridine, (4aR,9bR)-4-a-methyl-2,3,4,4a,5,9b-hexahydro-1H-indeno[1,2-b]pyridine, (4aS,9bS)-4-a-methyl-2,3,4,4a,5,9b-hexahydro-1H-indeno[1,2-b]pyridine, (4aRS,9bSR)-4-a-isopropyl-2,3,4,4a,5,9b-hexahydro-1H-indeno[1,2-b]pyridine, (4aR,9bR)-4-a-ethyl-2,3,4,4a,5,9b-hexahydro-1H-indeno[1,2-b]pyridine, (4aS,9bS)-4-a-ethyl-2,3,4,4a,5,9b-hexahydro-1H-indeno[1,2-b]pyridine, (4aRS,9bRS)-8-methoxy-1,4-a-dimethyl-2,3,4,4a,5,9b-hexahydro-1H-indeno[1,2-b]pyridine, (4aRS,9bRS)-4-a,9b-dimethyl-2,3,4,4a,5,9b-hexahydro-1H-indeno[1,2-b]pyridine, (4aRS,9bRS)-4-a-(ethoxymethyl)-2,3,4,4a,5,9b-hexahydro-1H-indeno[1,2-b]pyridine, (4aRS,9bRS)-4-a-(methoxymethyl)-9b-methyl-2,3,4,4a,5,9b-hexahydro-1H-indeno[1,2-b]pyridine, (5aRS,10bSR)-5a-methyl-1,2,3,4,5,5a,6,10b-octahydroindeno[1,2-b]azepine, [(4aRS,9bRS)-4-a-ethyl-2,3,4,4a,5,9b-hexahydro-1H-indeno[1,2-b]pyridin-8-yl]methanol, (4aR,9bR)-4-a,9b-dimethyl-2,3,4,4a,5,9b-hexahydro-1H-indeno[1,2-b]pyridine, or (4aS,9bS)-4-a,9b-dimethyl-2,3,4,4a,5,9b-hexahydro-1H-indeno[1,2-b]pyridine, or a pharmaceutically acceptable salt thereof.

8. The compound or a pharmaceutically acceptable salt thereof of claim 1, which is (4aRS,9bRS)-4-a-methyl-2,3,4,4a,5,9b-hexahydro-1H-indeno[1,2-b]pyridine, (4aR,9bR)-4-a-methyl-2,3,4,4a,5,9b-hexahydro-1H-indeno[1,2-b]pyridine, (4aS,9bS)-4-a-methyl-2,3,4,4a,5,9b-hexahydro-1H-indeno[1,2-b]pyridine, (4aRS,9bRS)-4-a-ethyl-2,3,4,4a,5,9b-hexahydro-1H-indeno[1,2-b]pyridine, (4aR,9bR)-4-a-ethyl-2,3,4,4a,5,9b-hexahydro-1H-indeno[1,2-b]pyridine, (4aS,9bS)-4-a-ethyl-2,3,4,4a,5,9b-hexahydro-1H-indeno[1,2-b]pyridine, (4aRS,9bRS)-4-a,9b-dimethyl-2,3,4,4a,5,9b-hexahydro-1H-indeno[1,2-b]pyridine, (4aR,9bR)-4-a,9b-dimethyl-2,3,4,4a,5,9b-hexahydro-1H-indeno[1,2-b]pyridine, or (4aS,9bS)-4-a,9b-dimethyl-2,3,4,4a,5,9b-hexahydro-1H-indeno[1,2-b]pyridine, or a pharmaceutically acceptable salt thereof.

9. A pharmaceutical composition comprising the compound or a pharmaceutically acceptable salt thereof of claim 1, and a pharmaceutically acceptable excipient.

10. A method for treating Alzheimer's disease, cerebrovascular dementia, Parkinson's disease, ischemic apoplexy, pain, intractable depression, attention deficit hyperactivity disorder, migraines, schizophrenia, generalized anxiety disorder, obsessive-compulsive disorder, autism, bulimia, or drug addiction, comprising administering to a patient an effective amount of the compound of claim 1 or a pharmaceutically acceptable salt thereof.

11. The method for treating of claim 10, which is a method for treating Alzheimer's disease, cerebrovascular dementia, Parkinson's disease, intractable depression, attention deficit hyperactivity disorder, or migraines.

12. (4aR,9bR)-4a-methyl-2,3,4,4a,5,9b-hexahydro-1H-indeno[1,2-b]pyridine or a pharmaceutically acceptable salt thereof as a single optical isomer.

13. (4aS,9bS)-4a-methyl-2,3,4,4a,5,9b-hexahydro-1H-indeno[1,2-b]pyridine or a pharmaceutically acceptable salt thereof as a single optical isomer.

14. (4aR,9bR)-4a-ethyl-2,3,4,4a,5,9b-hexahydro-1H-indeno[1,2-b]pyridine or a pharmaceutically acceptable salt thereof as a single optical isomer.

15. (4aS,9bS)-4-a-ethyl-2,3,4,4a,5,9b-hexahydro-1H-indeno[1,2-b]pyridine or a pharmaceutically acceptable salt thereof as a single optical isomer.

16. (4aR,9bR)-4a,9b-dimethyl-2,3,4,4a,5,9b-hexahydro-1H-indeno[1,2-b]pyridine or a pharmaceutically acceptable salt thereof as a single optical isomer.

17. (4aS,9bS)-4a,9b-dimethyl-2,3,4,4a,5,9b-hexahydro-1H-indeno[1,2-b]pyridine or a pharmaceutically acceptable salt thereof as a single optical isomer.

* * * * *

UNITED STATES PATENT AND TRADEMARK OFFICE
CERTIFICATE OF CORRECTION

| | | |
|---|---|---|
| PATENT NO. | : 8,211,907 B2 | Page 1 of 4 |
| APPLICATION NO. | : 12/741307 | |
| DATED | : July 3, 2012 | |
| INVENTOR(S) | : Satoshi Hayashibe et al. | |

It is certified that error appears in the above-identified patent and that said Letters Patent is hereby corrected as shown below:

<u>TITLE PAGE AT ABSTRACT ITEM (57):</u>

Line 6, "completed" should read --completing--.

<u>IN THE SPECIFICATIONS:</u>

<u>COLUMN 1:</u>

Line 4, "JH2008/071370" should read --JP2008/071370--.

<u>COLUMN 4:</u>

Line 20, "completed" should read --completing--.

<u>COLUMN 8:</u>

Line 61, "an" should read --a--.

<u>COLUMN 21:</u>

Line 3, "resent" should read --resents--.

<u>COLUMN 25:</u>

Line 54, "NMR-CDCl3:" should read --NMR-CDCl$_3$:--; and
    Line 55, "NMR-CD3OD:" should read --NMR-CD$_3$OD:--.

<u>COLUMN 26:</u>

Line 58, "amorphous." should read --amorphous substance.--.

Signed and Sealed this
Sixteenth Day of April, 2013

Teresa Stanek Rea
*Acting Director of the United States Patent and Trademark Office*

CERTIFICATE OF CORRECTION (continued)
U.S. Pat. No. 8,211,907 B2

COLUMN 27:

Line 67, "amorphous." should read --amorphous substance.--.

COLUMN 29:

Line 66, "acetate," should read --acetate;--.

COLUMN 30:

Line 30, "amorphous." should read --amorphous substance.--.

COLUMN 33:

Line 9, "amorphous." should read --amorphous substance.--.

COLUMN 34:

Line 24, "from" should read --form--.

COLUMN 35:

Line 12, "separation," should read --separation;--; and
    Line 24, "-4-aH-" should read -- -4aH- --.

COLUMN 36:

Line 7, "amorphous." should read --amorphous substance.--; and
    Line 42, "form," should read --form;--.

COLUMN 41:

Line 36, "were" should read --was--.

COLUMN 45:

Line 49, "from" should read --form--.

COLUMN 46:

Line 4, "from" should read --form--;
    Line 27, "from" should read --form--;
    Line 54, "(+)-(4aS,9bS)-4-a-" should read --(+)-(4aS,9bS)-4a- --; and
    Line 57, "(4aS,9bS)-4-a-" should read --(4aS,9bS)-4a- --.

COLUMN 74:

Table 23, Ex 68, " 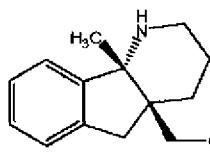 " should read -- 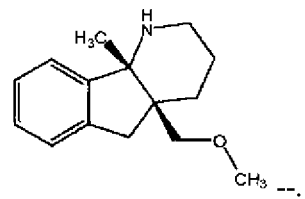 --.

COLUMN 78:

Px 82, "NMR-CDCl3:" should read --NMR-CDCl$_3$:--;
Px 83, "NMR-CDCl3:" should read --NMR-CDCl$_3$:--; and
Px 100, "NMR-CDCl3:" should read --NMR-CDCl$_3$:--.

COLUMN 81:

Ex 34-2, "NMR-CD3OD:" should read --NMR-CD$_3$OD:--; and
Ex 41, "NMR-CD3OD:" should read --NMR-CD$_3$OD:--.

COLUMN 83:

Ex 42, "NMR-CD3OD:" should read --NMR-CD$_3$OD:--;
Ex 58, "NMR-CD3OD:" should read --NMR-CD$_3$OD:--; and
Ex 59, "NMR-CD3OD:" should read --NMR-CD$_3$OD:--.

COLUMN 85:

Ex 78-1, "NMR-CDCl3:" should read --NMR-CDCl$_3$:--;
Ex 79-1, "NMR-CDCl3:" should read --NMR-CDCl$_3$:--; and
Ex 80-1, "NMR-CDCl3:" should read --NMR-CDCl$_3$:--.

IN THE CLAIMS:

COLUMN 91:

Claim 7, Line 34, "(4aRS,9bRS)-4-a-" should read --(4aRS,9bRS)-4a- --;
Claim 7, Line 40, "(4aS,9bS)-4-a,9b-" should read --(4aS,9bS)-4a,9b- --;
Claim 8, Line 44, "(4aRS,9bRS)-4-a-" should read --(4aRS,9bRS)-4a- --; and
Claim 8, Lines 45-46, "(4aR,9bR)-4-a-" should read --(4aR,9bR)-4a- --.

COLUMN 92:

Claim 8, Line 1, "(4aS,9bS)-4-a-" should read --(4aS,9bS)-4a- --;
Claim 8, Line 2, "(4aRS,9bRS)-4-a-" should read --(4aRS,9bRS)-4a- --;
Claim 8, Line 3, "(4aR,9bR)-4-a-" should read --(4aR,9bR)-4a- --;

CERTIFICATE OF CORRECTION (continued)
U.S. Pat. No. 8,211,907 B2

Claim 8, Line 5, "(4aS,9bS)-4-a-" should read --(4aS,9bS)-4a- --;
Claim 8, Line 6, "(4aRS,9bRS)-4-a," should read --(4aRS,9bRS)-4a,--;
Claim 8, Line 7, "(4aR,9bR)-4-a," should read --(4aR,9bR)-4a,--;
Claim 8, Line 9, "(4aS,9bS)-4-a," should read --(4aS,9bS)-4a,--; and
Claim 15, Line 36, "(4aS,9bS)-4-a-" should read --(4aS,9bS)-4a- --.